United States Patent
Brubaker et al.

(10) Patent No.: US 10,035,789 B2
(45) Date of Patent: Jul. 31, 2018

(54) COMPOUNDS USEFUL FOR TREATING DISORDERS RELATED TO RET

(71) Applicant: BLUEPRINT MEDICINES CORPORATION, Cambridge, MA (US)

(72) Inventors: Jason D. Brubaker, Cambridge, MA (US); Lucian V. Dipietro, Gloucester, MA (US)

(73) Assignee: BLUEPRINT MEDICINES CORPORATION, Cambridge, MA (US)

( * ) Notice: Subject to any disclaimer, the term of this patent is extended or adjusted under 35 U.S.C. 154(b) by 0 days.

(21) Appl. No.: 15/660,840

(22) Filed: Jul. 26, 2017

(65) Prior Publication Data

US 2018/0030032 A1    Feb. 1, 2018

Related U.S. Application Data

(60) Provisional application No. 62/367,493, filed on Jul. 27, 2016.

(51) Int. Cl.
*A61K 31/506* (2006.01)
*C07D 401/14* (2006.01)
*C07D 401/12* (2006.01)

(52) U.S. Cl.
CPC ......... *C07D 401/14* (2013.01); *C07D 401/12* (2013.01)

(58) Field of Classification Search
CPC .............................. C07D 401/14; C07D 401/12
See application file for complete search history.

(56) References Cited

U.S. PATENT DOCUMENTS

| | | | |
|---|---|---|---|
| 8,802,697 B2 | 8/2014 | Bifulco, Jr. et al. | |
| 9,126,951 B2 | 9/2015 | Bifulco, Jr. et al. | |
| 9,200,002 B2 * | 12/2015 | Hodous ................... | A61K 31/53 |
| 9,334,263 B2 | 5/2016 | Hodous et al. | |
| 9,340,514 B2 | 5/2016 | Bifulco, Jr. et al. | |
| 9,434,700 B2 | 9/2016 | Bifulco, Jr. et al. | |
| 9,499,522 B2 | 11/2016 | DiPietro et al. | |
| 9,688,680 B2 * | 6/2017 | Hodous ................ | C07D 487/04 |
| 9,695,165 B2 | 7/2017 | Bifulco, Jr. et al. | |
| 2013/0115313 A1 | 5/2013 | Charrier et al. | |
| 2014/0187559 A1 | 7/2014 | Miduturu | |
| 2016/0102097 A1 | 4/2016 | Hodous et al. | |
| 2017/0022206 A1 | 1/2017 | Hodous et al. | |
| 2017/0029409 A1 | 2/2017 | DiPietro et al. | |
| 2017/0057953 A1 | 3/2017 | Hodous et al. | |
| 2017/0066773 A1 | 3/2017 | Wenglowsky et al. | |
| 2017/0066812 A1 | 3/2017 | Bifulco, Jr. et al. | |
| 2017/0121312 A1 * | 5/2017 | Brubaker ............. | C07D 401/14 |
| 2017/0145018 A1 | 5/2017 | Wenglowsky et al. | |
| 2017/0174652 A1 | 6/2017 | Bifulco, Jr. et al. | |
| 2017/0204104 A1 | 7/2017 | Hodous et al. | |
| 2017/0253593 A1 | 9/2017 | Bifulco, Jr. et al. | |
| 2017/0267661 A1 | 9/2017 | Kim et al. | |
| 2017/0298069 A1 | 10/2017 | Brooijmans et al. | |

FOREIGN PATENT DOCUMENTS

| | | |
|---|---|---|
| WO | WO 2001/060816 A1 | 8/2001 |
| WO | WO 2004/009087 A1 | 1/2004 |
| WO | WO 2007/023382 A2 | 3/2007 |
| WO | WO 2009/003136 A1 | 12/2008 |
| WO | WO 2009/014637 A2 | 1/2009 |
| WO | WO 2011/060295 A1 | 5/2011 |
| WO | WO 2014/039971 A1 | 3/2014 |
| WO | WO 2014/072220 A1 | 5/2014 |
| WO | WO 2014/130810 A1 | 8/2014 |
| WO | WO 2016/127074 A1 | 8/2016 |
| WO | WO 2017/079140 A1 | 5/2017 |

OTHER PUBLICATIONS

Kinase Inhibitors, Methods in Molecular Biology 795 (B. Kuster ed., 2012).*
W. Brandt et al., 45 European Journal of Medicinal Chemistry, 2919-2927 (2010).*
L. Mologni et al., 18 Bioorganic & Medicinal Chemistry, 1482-1496 (2010).*
R. Graham et al., 17 Bioorganic & Medicinal Chemistry, 5886-5893 (2007).*
E. Arighi et al., 16 Cytokine & Growth Factor Reviews, 441-467 (2005).*
L. Mologni et al., 377 Molecular and Cellular Endocrinology, 1-6 (2013).*
I. Plaza-Menacho et al., 26 Cellular Signalling, 1743-1752 (2014).*
Abdel-Rahman, O. and M. Fouad (2014) "Risk of cardiovascular toxicities in patients with solid tumors treated with sunitinib, axitinib, cediranib or regorafenib, an updated systematic review and comparative meta-analysis" *Crit Rev Oncol Hematol*, 92:194-207.
Bentzien, F. et al. (2013) "In Vitro and In Vivo Activity of Cabozantinib (XL184), an Inhibitor of RET, MET, and VEGFR2, in a Model of Medullary Thyroid Cancer" *Thyroid*, 23(12):1569-1577.
Carlomagno, F. et al. (Feb. 1995) "Point Mutation of the *Ret* Proto-oncogene in the TT Human Medullary Thyroid Carcinoma Cell Line" *Biochem Biophys Res Commun*, 207(3):1022-1028.
Hayashi, H. et al. (2000) "Characterization of intracellular signals via tyrosine 1062 in RET activated by glial cell line-derived neurotrophic factor" *Oncogene*, 19:4469-4475.
International Search Report and Written Opinion dated Apr. 29, 2016, in International Patent Application No. PCT/US2016/016808, filed Feb. 5, 2016, by Blueprint Medicines Corp. (8 pages).

(Continued)

*Primary Examiner* — Alexander R Pagano

(74) *Attorney, Agent, or Firm* — Finnegan, Henderson, Farabow, Garrett & Dunner, LLP

(57) ABSTRACT

Described herein are compounds that inhibit wild-type RET and its resistant mutants, pharmaceutical compositions including such compounds, and methods of using such compounds and compositions.

21 Claims, No Drawings

(56) References Cited

OTHER PUBLICATIONS

International Search Report and Written Opinion dated Jan. 18, 2017, in International Patent Application No. PCT/US2016/059879, filed Nov. 1, 2016, by Blueprint Medicines Corp. (12 pages).
International Search Report and Written Opinion dated Jun. 12, 2017, in International Patent Application No. PCT/US2017/022969, filed Mar. 17, 2017, by Blueprint Medicines Corp. (12 pages).
International Search Report and Written Opinion dated Oct. 12, 2017, in International Patent Application No. PCT/US2017/043964, filed Jul. 26, 2017, by Blueprint Medicines Corp. (13 pages).
International Search Report and Written Opinion dated Oct. 25, 2017, in International Patent Application No. PCT/US2017/043340, filed Jul. 21, 2017, by Blueprint Medicines Corp. (14 pages).
Mologni, L et al. (2017) "RET kinase inhibitors: a review of recent patents (2012-2015)" *Exp Opin Ther Patents*, 27(1):91-99.
Notice of Allowance dated Sep. 26, 2017, in U.S. Appl. No. 15/093,354, filed Apr. 7, 2016, by Blueprint Medicines Corp.
Notice of Allowance dated Sep. 5, 2017, in U.S. Appl. No. 15/217,503, filed Jul. 22, 2016, by Blueprint Medicines Corp.
Notice of Allowance dated Oct. 25, 2017, in U.S. Appl. No. 15/340,428, filed Nov. 1, 2016, by Blueprint Medicines Corp.
Suzuki, M. et al. (Jul. 2013) "Identification of a lung adenocarcinoma cell line with CCDC6-RET fusion gene and the effect of RET inhibitors in vitro and in vivo" *Cancer Sci*, 104(7):896-903.
Touat, M. et al. (2015) "Targeting FGFR Signaling in Cancer" *Clin Cancer Res*, 21(12):2684-2694.
U.S. Appl. No. 15/548,925, filed Aug. 4, 2017, by Blueprint Medicines Corp.
U.S. Appl. No. 15/657,057, filed Jul. 21, 2017, by Blueprint Medicines Corp.

* cited by examiner

COMPOUNDS USEFUL FOR TREATING DISORDERS RELATED TO RET

CLAIM OF PRIORITY

This application claims priority from U.S. Provisional Application No. 62/367,493, filed Jul. 27, 2016, which is incorporated herein in its entirety.

This disclosure relates to inhibitors of RET that are active against wild-type RET and its resistant mutants.

SEQUENCE LISTING

The instant application contains a Sequence Listing which has been filed electronically in ASCII format and is hereby incorporated by reference in its entirety. Said ASCII copy, created on Jul. 21, 2017, is named 14320_0020-00000_SL.txt and is 32,334 bytes in size.

BACKGROUND

RET is a receptor tyrosine kinase that activates multiple downstream pathways involved in cell proliferation and survival. RET fusions are implicated in several cancers including papillary thyroid carcinoma and non-small cell lung cancer. A genomics analysis on the landscape of kinase fusions identified RET fusions in breast and colon cancer patient samples, providing therapeutic rationale for the use of RET inhibitors in multiple patient subpopulations.

The identification of RET fusions as drivers in some cancers prompted the use of approved multi-kinase inhibitors with RET inhibitory activity to treat patients whose tumors express a RET fusion protein. However, these drugs cannot always be dosed at the levels required to sufficiently inhibit RET due to toxicities that result from inhibition of targets other than RET. Further, one of the greatest challenges in treating cancer is the ability of tumor cells to become resistant to therapy. Kinase reactivation via mutation is a common mechanism of resistance. When resistance occurs, the patient's treatment options are often very limited, and the cancer progresses, unchecked, in most instances. There is thus a need for compounds that inhibit RET, as well as its resistant mutants.

SUMMARY

In one aspect, the disclosure features a compound having the structural formula (I):

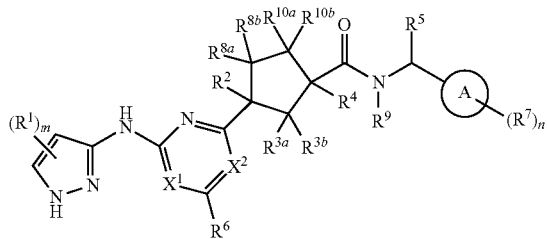

(I)

or a stereoisomer thereof, of a pharmaceutically acceptable salt of either of the foregoing, wherein: ring A is an aryl or heteroaryl ring; each of $X^1$ and $X^2$ is independently selected from N and $C(R^{6'})$; each $R^1$ and each $R^7$ is independently selected from $C_1$-$C_6$ alkyl, $C_2$-$C_6$ alkenyl, $C_2$-$C_6$ alkynyl, $C_1$-$C_6$ alkoxy, halo, $C_1$-$C_6$ heteroalkyl, cycloalkyl, aryl, heteroaryl, aryloxy, aralkyl, heterocyclyl, heterocyclylalkyl, nitro, cyano, —C(O)$R^c$, —OC(O)$R^c$, —C(O)O$R^d$, —($C_1$-$C_6$ alkylene)-C(O)$R^c$, —S$R^d$, —S(O)$_2$$R^c$, —S(O)$_2$—N($R^d$)($R^d$), —($C_1$-$C_6$ alkylene)-S(O)$_2$$R^c$, —($C_1$-$C_6$ alkylene)-S(O)$_2$—N($R^d$)($R^d$), —N($R^d$)($R^d$), —C(O)—N($R^d$)($R^d$), —N($R^d$)—C(O)$R^c$, —N($R^d$)—C(O)O$R^c$, —($C_1$-$C_6$ alkylene)-N($R^d$)—C(O)$R^c$, —N($R^d$)S(O)$_2$$R^c$, and —P(O)($R^c$)($R^c$); wherein each of alkyl, alkenyl, alkynyl, alkoxy, heteroalkyl, cycloalkyl, aryl, heteroaryl, aryloxy, aralkyl, heterocyclyl, and heterocyclylalkyl is independently substituted with 0-5 occurrences of $R^a$; or two $R^1$ or two $R^7$ are taken together with the carbon atoms to which they are attached form a cycloalkyl or heterocyclyl ring independently substituted with 0-5 occurrences of $R^b$; each of $R^2$, $R^{3a}$, $R^{3b}$, $R^4$, $R^{8a}$, $R^{8b}$, $R^{10a}$ and $R^{10b}$ is independently selected from hydrogen, $C_1$-$C_6$ alkyl, $C_1$-$C_6$ alkoxy, halo, hydroxyl, cyano, $C_1$-$C_6$ heteroalkyl, and —N($R^d$)($R^d$); wherein each of alkyl, alkoxy, and heteroalkyl is optionally and independently substituted with 0-5 occurrences of $R^a$; each of $R^5$ and $R^9$ is independently selected from hydrogen, $C_1$-$C_6$ alkyl, and $C_1$-$C_6$ heteroalkyl; wherein each alkyl and heteroalkyl is optionally and independently substituted with 0-5 occurrences of $R^a$; $R^6$ and each $R^{6'}$ is independently selected from hydrogen, $C_1$-$C_6$ alkyl, $C_1$-$C_6$ alkoxy, halo, cyano, $C_1$-$C_6$ heteroalkyl, and —N($R^d$)($R^d$); wherein each alkyl, alkoxy, and heteroalkyl is optionally and independently substituted with 0-5 occurrences of $R^a$; each $R^a$ and each $R^b$ is independently selected from $C_1$-$C_6$ alkyl, halo, hydroxyl, $C_1$-$C_6$ heteroalkyl, $C_1$-$C_6$ alkoxy, cycloalkyl, heterocyclyl, or cyano, wherein each of alkyl, heteroalkyl, alkoxy, cycloalkyl and heterocyclyl is independently substituted with 0-5 occurrences of R'; each R' is independently selected from $C_1$-$C_6$ alkyl, $C_1$-$C_6$ heteroalkyl, halo, hydroxyl, cycloalkyl or cyano; or two R' together with the atom(s) to which they are attached form a cycloalkyl or heterocyclyl ring; each $R^c$ is independently selected from hydrogen, hydroxyl, halo, thiol, $C_1$-$C_6$ alkyl, $C_1$-$C_6$ thioalkyl, $C_1$-$C_6$ alkoxy, $C_1$-$C_6$ heteroalkyl, cycloalkyl, cycloalkylalkyl, heteroarylalkyl, heterocyclyl, and heterocyclylalkyl, wherein each of alkyl, thioalkyl, alkoxy, heteroalkyl, cycloalkyl, cycloalkylalkyl, heteroarylalkyl, heterocyclyl, and heterocyclylalkyl is independently substituted with 0-5 occurrences of $R^a$, or two $R^c$ together with the atom(s) to which they are attached form a cycloalkyl or heterocyclyl ring independently substituted with 0-5 occurrences of $R^b$; each $R^d$ is independently selected from hydrogen, $C_1$-$C_6$ alkyl, $C_1$-$C_6$ heteroalkyl, cycloalkyl, cycloalkylalkyl, heteroarylalkyl, heterocyclyl, and heterocyclylalkyl, wherein each of alkyl, heteroalkyl, cycloalkyl, cycloalkylalkyl, heteroarylalkyl, heterocyclyl, and heterocyclylalkyl is independently substituted with 0-5 occurrences of $R^a$, or two $R^d$ together with the atom(s) to which they are attached form a cycloalkyl or heterocyclyl ring independently substituted with 0-5 occurrences of $R^b$; m is 0, 1, or 2; and n is 0, 1, 2, or 3.

In some embodiments, the compound has the structural formula (Ia):

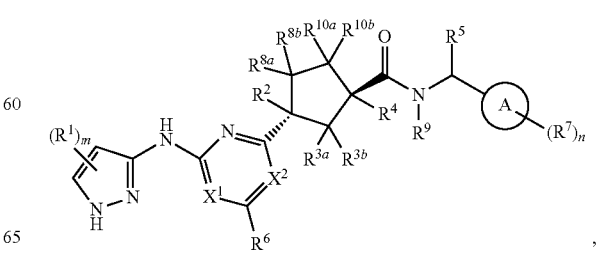

(Ia)

or a pharmaceutically acceptable salt thereof, wherein ring A, $X^1$, $X^2$, $R^1$, $R^2$, $R^{3a}$, $R^{3b}$, $R^4$, $R^5$, $R^6$, $R^7$, $R^{8a}$, $R^{8b}$, $R^9$, $R^{10a}$, $R^{10b}$, m and n are as defined herein.

In some embodiments, the compound has the structural formula (Ib):

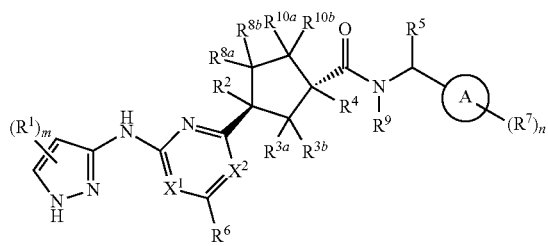

(Ib)

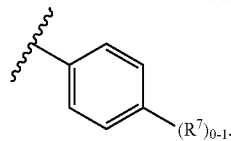

$(R^7)_{0-1}$.

In some embodiments, n is 0 or 1; and $R^7$, if present, is selected from pyrazol-1-yl substituted with 0-3 occurrences of $R^b$, and —O—$C_1$-$C_4$ alkyl substituted with 0-3 occurrences of $R^a$.

In some embodiments, $R^7$ is selected from 4-fluoropyrazol-1-yl, 4-chloropyrazol-1-yl, 3,5-dimethylpyrazol-1-yl, pyrazol-1-yl and —OCH$_2$CH$_3$, or $R^7$ is absent.

In some embodiments, $R^9$ is hydrogen.

In some embodiments, $X^1$ is $C(R^{6'})$ and $X^2$ is N. In some embodiments, $X^1$ is $C(R^{6'})$ and $X^2$ is $C(R^{6'})$.

In one aspect, the disclosure features a compound having the structural formula (II):

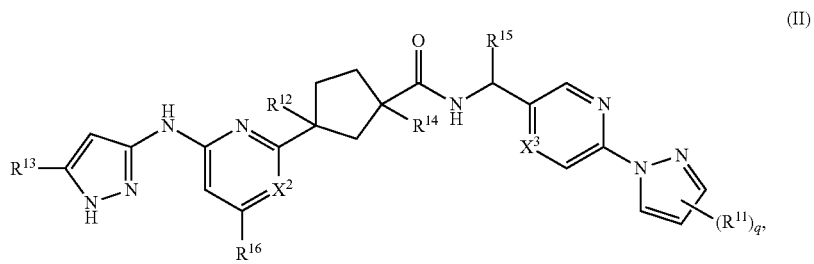

(II)

or a pharmaceutically acceptable salt thereof, wherein ring A, $X^1$, $X^2$, $R^1$, $R^2$, $R^{3a}$, $R^{3b}$, $R^4$, $R^5$, $R^6$, $R^7$, $R^{8a}$, $R^{8b}$, $R^9$, m and n are as defined herein.

In some embodiments, m is 1; $R^1$ is located at the 5-position; and $R^1$ is selected $C_1$-$C_4$ alkyl or $C_3$-$C_6$ cycloalkyl, wherein $R^1$ is substituted with 0-3 occurrences of $R^a$.

In some embodiments, $R^1$ is —CH$_3$ or cyclopropyl.

In some embodiments, $R^2$ is hydrogen or hydroxyl.

In some embodiments, each of $R^{3a}$, $R^{3b}$, $R^{8a}$, $R^{8b}$, $R^{10a}$ and $R^{10b}$ is hydrogen.

In some embodiments, $R^4$ is hydrogen or $C_1$-$C_4$ alkyl, substituted with 0-3 occurrences of $R^a$. In some embodiments, $R^4$ is hydrogen or —CH$_3$.

In some embodiments, $R^5$ is hydrogen or $C_1$-$C_4$ alkyl substituted with 0-3 occurrences of $R^a$. In some embodiments, $R^5$ is hydrogen or —CH$_3$.

In some embodiments, $R^6$ is $C_1$-$C_4$ alkyl substituted with 0-3 occurrences of $R^a$. In some embodiments, each $R^6$ is —CH$_3$.

In some embodiments, each $R^{6'}$ is hydrogen.

In some embodiments, ring A is a 6-membered monocyclic heteroaryl comprising at least one nitrogen ring atom or phenyl. In some embodiments, ring A is selected from:

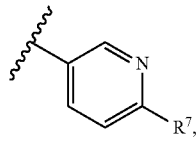 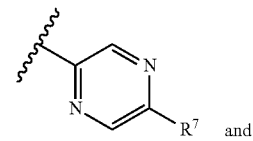

$R^7$,          $R^7$ and or a stereoisomer thereof, or a pharmaceutically acceptable salt of either of the foregoing, wherein: $X^2$ is selected from N and CH; $X^3$ is selected from N and CH; each $R^{11}$, if present, is independently selected from halo and —$C_1$-$C_4$ alkyl substituted with 0-3 occurrences of $R^a$; $R^{12}$ is hydrogen or hydroxyl; $R^{13}$ is selected from $C_1$-$C_4$ alkyl or $C_3$-$C_6$ cycloalkyl, wherein $R^{13}$ is substituted with 0-3 occurrences of $R^a$; $R^{14}$ is selected from hydrogen and —$C_1$-$C_4$ alkyl substituted with 0-3 occurrences of $R^a$; $R^{15}$ is selected from hydrogen and —$C_1$-$C_4$ alkyl substituted with 0-3 occurrences of $R^a$; $R^{16}$ is selected from hydrogen and —$C_1$-$C_4$ alkyl substituted with 0-3 occurrences of $R^a$; q is 0, 1 or 2; each $R^a$ is independently selected from $C_1$-$C_6$ alkyl, halo, hydroxyl, $C_1$-$C_6$ heteroalkyl, $C_1$-$C_6$ alkoxy, cycloalkyl, heterocyclyl, or cyano, wherein each of alkyl, heteroalkyl, alkoxy, cycloalkyl and heterocyclyl is independently substituted with 0-5 occurrences of R'; and each R' is independently selected from $C_1$-$C_6$ alkyl, $C_1$-$C_6$ heteroalkyl, halo, hydroxyl, cycloalkyl or cyano; or two R' together with the atom(s) to which they are attached form a cycloalkyl or heterocyclyl ring.

In some embodiments, each $R^{11}$, if present, is independently selected from fluoro and —CH$_3$; $R^{13}$ is selected from —CH$_3$ and cyclopropyl; $R^{14}$ is selected from hydrogen and —CH$_3$; $R^{15}$ is selected from hydrogen and —CH$_3$; and $R^{16}$ is —CH$_3$.

In one aspect, the disclosure features a compound having the structural formula (III):

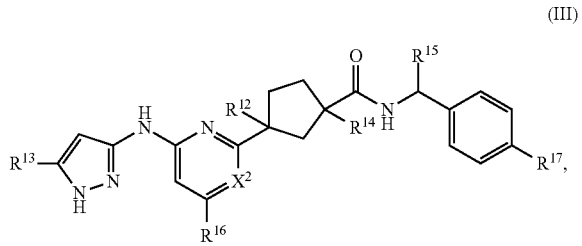

(III)

or a stereoisomer thereof, or a pharmaceutically acceptable salt of either of the foregoing, wherein: $X^2$ is selected from N and CH; $R^{12}$ is hydrogen or hydroxyl; $R^{13}$ is selected from $C_1$-$C_4$ alkyl or $C_3$-$C_6$ cycloalkyl, wherein $R^{13}$ is substituted with 0-3 occurrences of $R^a$; $R^{14}$ is selected from hydrogen and —$C_1$-$C_4$ alkyl substituted with 0-3 occurrences of $R^a$; $R^{15}$ is selected from hydrogen and —$C_1$-$C_4$ alkyl substituted with 0-3 occurrences of $R^a$; $R^{16}$ is selected from hydrogen and —$C_1$-$C_4$ alkyl substituted with 0-3 occurrences of $R^a$; $R^{17}$ is selected from hydrogen, —$C_1$-$C_4$ alkyl substituted with 0-3 occurrences of $R^a$, or O—$C_1$-$C_4$ alkyl substituted with 0-3 occurrences of $R^a$; each $R^a$ is independently selected from $C_1$-$C_6$ alkyl, halo, hydroxyl, $C_1$-$C_6$ heteroalkyl, $C_1$-$C_6$ alkoxy, cycloalkyl, heterocyclyl, or cyano, wherein each of alkyl, heteroalkyl, alkoxy, cycloalkyl and heterocyclyl is independently substituted with 0-5 occurrences of R'; and each R' is independently selected from $C_1$-$C_6$ alkyl, $C_1$-$C_6$ heteroalkyl, halo, hydroxyl, cycloalkyl or cyano; or two R' together with the atom(s) to which they are attached form a cycloalkyl or heterocyclyl ring.

In some embodiments, $R^{13}$ is selected from —$CH_3$ and cyclopropyl; $R^{14}$ is selected from hydrogen and —$CH_3$; $R^{15}$ is selected from hydrogen and —$CH_3$; $R^{16}$ is —$CH_3$; and $R^{17}$ is selected from hydrogen and —$OCH_3$.

In one aspect, the disclosure features a pharmaceutical composition comprising a compound as described herein; and a pharmaceutically acceptable carrier.

In one aspect, the disclosure features a method for inhibiting RET activity in a cell or in a subject, comprising the step of contacting the cell or administering to the patient a compound as described herein or a pharmaceutical composition thereof. In some embodiments, the cell or patient has, or has been identified as having, a RET alteration, e.g., a RET mutation, e.g., a fusion or point mutation. In some embodiments, the patient comprises a RET-altered cell, cancer, gene, or gene product.

In one aspect, the disclosure features a method for treating a subject suffering from a condition mediated by aberrant RET activity, comprising administering to the subject a therapeutically effective amount of a compound as described herein or a pharmaceutical composition thereof. In some embodiments, the subject has or has been identified as having (e.g., wherein a cancer cell in the subject has or has been identified as having) a RET alteration, e.g., a RET mutation, e.g., a fusion or point mutation. In some embodiments, a cell, cancer, gene, or gene product from the subject is or has been identified as being RET-altered. In some embodiments, the subject has or has been identified as having (e.g., a cancer cell in the subject has or has been identified as having) a RET alteration, e.g., a RET mutation, e.g., a fusion or point mutation.

In some embodiments, the condition mediated by aberrant RET activity is a condition mediated by any RET activity that is not normal e.g., any activity due to a RET-altered gene or gene product, which affects the amount or activity of the gene or gene product as compared to the normal or wild-type gene. In some embodiments, the condition mediated by aberrant RET activity is a familial or sporadic cancer, e.g., a solid tumor such as thyroid, lung, breast, or pancreatic. In some embodiments, the condition mediated by aberrant RET activity is irritable bowel syndrome (IBS). In some embodiments, the aberrant RET activity promotes the condition, such that inhibition of RET ameliorates at least one symptom of the condition. In some embodiments, the aberrant RET activity comprises increased RET activity or expression level, gain of function mutation, and/or constitutive activation of RET. In some embodiments, the aberrant RET activity corresponds to aberrant amounts of RET, e.g., aberrant nucleic acid or protein amounts.

In one aspect, the disclosure features a method for treating a subject who has developed resistance to a cancer treatment comprising a wild-type RET inhibitor, comprising administering to the subject a therapeutically effective amount of a compound as described herein or a pharmaceutical composition thereof. In some embodiments, the subject is suffering from papillary thyroid carcinoma or non-small cell lung cancer.

In one aspect, the disclosure features a method for treating a subject who has developed resistance to a treatment for a condition mediated by aberrant RET activity, comprising administering to the subject a therapeutically effective amount of a compound as described herein or a pharmaceutical composition thereof. In some embodiments, the subject has developed resistance to a wild-type RET inhibitor. In some embodiments, the cancer treatment to which the subject is resistant is a wild-type RET inhibitor that is active against the wild-type RET, but less active, e.g., much less active, against one or more mutated forms of RET. In some embodiments, the wild-type RET inhibitor is selected from ponatinib, cabozanitib, and vandetanib.

In another aspect, the present disclosure provides a use of a compound or pharmaceutical composition described herein, e.g., a compound of structural Formula (I), (Ia), (Ib), (II), or (III) described herein (e.g., a compound in Table 1) or a pharmaceutically acceptable salt or composition thereof, in the manufacture of a medicament for inhibiting RET activity in a cell or in a subject. In some embodiments, the cell or subject has, or has been identified as having, a RET alteration, e.g., a RET mutation, e.g., a fusion or point mutation. In some embodiments, a cell, cancer, gene, or gene product from the subject is or has been identified as being RET-altered.

In another aspect, the present disclosure provides a use of a compound or pharmaceutical composition described herein, e.g., a compound of structural Formula (I), (Ia), (Ib), (II), or (III) described herein (e.g., a compound in Table 1) or a pharmaceutically acceptable salt or composition thereof, in the manufacture of a medicament for treating a subject suffering from a condition mediated by aberrant RET activity. In some embodiments, the subject has, or has been identified as having (e.g., wherein a cancer cell in the subject has, or has been identified as having) a RET alteration, e.g., a RET mutation, e.g., a fusion or point mutation. In some embodiments, a cell, cancer, gene, or gene product from the subject is or has been identified as being RET-altered.

In another aspect, the present disclosure provides a use of a compound or pharmaceutical composition described herein, e.g., a compound of structural Formula (I), (Ia), (Ib), (II), or (III) described herein (e.g., a compound in Table 1) or a pharmaceutically acceptable salt or composition thereof, in the manufacture of a medicament for treating a subject who has developed resistance to a cancer treatment.

In another aspect, the present disclosure provides a method of preventing development of one or more RET-altered cell, cancer, gene, or gene product, in a cell or in a patient, comprising the step of contacting the cell or administering to the patient a compound according to structural Formula (I), (Ia), (Ib), (II), or (III).

In another aspect, the present disclosure provides a method of treating a subject suffering from cancer comprising administering to the subject a compound described herein (e.g., a compound having a lower $IC_{50}$ for RET than for KDR, a compound having a similar $IC_{50}$ for wild-type RET compared to mutant RET, and/or a compound of structural Formula (I), (Ia), (Ib), (II), or (III) described herein (e.g., a compound in Table 1)), or a pharmaceutical composition comprising the compound, wherein the subject has a RET-altered cell, cancer, gene, or gene product that is responsive to the compound. In some embodiments, the disclosure provides a method of treating cancer in a patient, said method comprising administering an effective amount of a compound described herein to a patient having a RET-altered cell, cancer, gene, or gene product that is responsive to the compound.

In another aspect, the present disclosure provides a method of treating a subject suffering from cancer comprising the steps of:
a. receiving information related to a RET sequence, e.g., information related to a RET-altered gene or gene product, e.g., having a RET fusion or point mutation; and
b. administering to the subject a compound described herein (e.g., a compound having a lower $IC_{50}$ for RET than for KDR, a compound having a similar $IC_{50}$ for wild-type RET compared to mutant RET, and/or a compound of structural Formula (I), (Ia), (Ib), (II), or (III) described herein (e.g., a compound in Table 1)), or a pharmaceutical composition comprising the compound, if the information indicates a RET-altered cell, cancer, gene, or gene product.

In some embodiments, the subject is administered a cancer treatment other than a compound of structural Formula (I), (Ia), (Ib), (II), or (III) if the information indicates that the subject has a wild-type RET sequence. In some embodiments, the cancer treatment is a wild-type RET inhibitor.

In another aspect, the present disclosure provides a method of treating cancer in a subject, said method comprising:
a. obtaining a biological sample (e.g., a tumor biopsy) from a human subject;
b. detecting whether a RET-altered cell, cancer, gene, or gene product, e.g., having a fusion or point mutation, is present in the biological sample;
c. identifying the subject as responsive to a compound described herein (e.g., a compound having a lower $IC_{50}$ for RET than for KDR, a compound having a similar $IC_{50}$ for wild-type RET compared to mutant RET, and/or a compound of structural Formula (I), (Ia), (Ib), (II), or (III) described herein (e.g., a compound in Table 1)) when the presence of the RET-altered cell, cancer, gene, or gene product in the biological sample is detected; and
d. administering an effective amount of the compound to the subject.

In another aspect, the present disclosure provides a method of treating cancer in a subject, said method comprising:
a. determining if, having determined if, or receiving information that the subject has a RET-altered cell, cancer, gene, or gene product, e.g., having a fusion or point mutation;
b. identifying the subject as responsive to a compound described herein (e.g., a compound having a lower $IC_{50}$ for RET than for KDR, a compound having a similar $IC_{50}$ for wild-type RET compared to mutant RET, and/or a compound of structural Formula (I), (Ia), (Ib), (II), or (III) described herein (e.g., a compound in Table 1)) when the subject has a RET-altered cell, cancer, gene, or gene product; and
c. administering an effective amount of the compound to the subject.

In another aspect, the present disclosure provides a method of diagnosing cancer in a subject, said method comprising:
a. obtaining a biological sample (e.g., a tumor biopsy) from a human subject;
b. detecting whether a RET-altered cell, cancer, gene, or gene product, e.g., having a fusion or point mutation, is present in the biological sample;
c. diagnosing the subject with cancer when the presence of the RET-altered cell, cancer, gene, or gene product in the biological sample is detected.

In another aspect, the present disclosure provides a method of predicting the efficacy of a compound described herein (a compound having a lower $IC_{50}$ for RET than for KDR, a compound having a similar $IC_{50}$ for wild-type RET compared to mutant RET, and/or a compound of structural Formula (I), (Ia), (Ib), (II), or (III) described herein (e.g., a compound in Table 1)) in a treatment of cancer in a subject comprising the step of:
determining if, having determined if, or receiving information that the subject has a RET-altered cell, cancer, gene, or gene product, e.g., having a mutation, e.g., a fusion or point mutation, e.g., by a method selected from hybridization-based methods, amplification-based methods, microarray analysis, flow cytometry analysis, DNA sequencing, next-generation sequencing (NGS), primer extension, PCR, in situ hybridization, dot blot, and Southern blot;
wherein said determining if, having determined if, or receiving information is predictive of efficacy of the compound in the treatment.

In some embodiments of any of the methods and uses herein, the method further comprises administering to the subject a compound described herein (e.g., a compound having a lower $IC_{50}$ for RET than for KDR, a compound having a similar $IC_{50}$ for wild-type RET compared to mutant RET, and/or a compound of structural Formula (I), (Ia), (Ib), (II), or (III) described herein (e.g., a compound in Table 1)), e.g., responsive to a determination or diagnosis made by a method described herein.

In some embodiments of any of the methods and uses herein, the RET-altered cell, cancer, gene, or gene product comprises a fusion mutation, e.g., CCDC6-RET or KIF5B-RET or a fusion of Table 3. In some embodiments, the RET-altered cell, cancer, gene, or gene product comprises a point mutation of amino acid position 634, 918, or 804 of RET, or a point mutation at a position listed in Table 4, e.g., a point mutation specified in Table 4. In some embodiments, the RET-altered cell, cancer, gene, or gene product comprises a point mutation at amino acid 634, 918, or 804, 806, 810, 865, 870, 891, e.g., is selected from RET C634W, M918T, V804L, V804E, V804M, V804L, V806C, Y806C, Y806S, Y806N, Y806H, G810R, G810S, L865V, L870F, and S891A. In some embodiments, the RET alteration is located at least partially within, or is located wholly within one or more of: the N-terminal extracellular domain (e.g., within one or more cadherin-like repeats and/or the cysteine-rich region), the transmembrane domain, or the tyrosine kinase domain (e.g., within one or more of the ATP binding site or proton acceptor site). In some embodiments, the RET fusion further comprises a point mutation, e.g., KIF5B-RET (V804L) or KIF5B-RET (V804M).

In some embodiments of any of the methods and uses herein, the subject suffers from a cancer selected from colorectal cancer, lung cancer (e.g., a lung adenocarcinoma, e.g., NSCLC), thyroid cancer (e.g., medullary thyroid cancer), or leukemia. In some embodiments, the subject suffers from a cancer listed herein, e.g., in Table 3.

In some embodiments, the cancer is wild-type RET.

In some embodiments, the cancer is lung cancer, e.g., a lung adenocarcinoma, and the RET-altered cell, cancer, gene, or gene product comprises a CCDC6-RET fusion. In some embodiments, the cancer is lung adenocarcinoma and the RET-altered cell, cancer, gene, or gene product comprises a KIF5B-RET fusion. In some embodiments, the cancer is lung adenocarcinoma and the RET-altered cell, cancer, gene, or gene product comprises KIF5B-RET (V804L). In some embodiments, the lung adenocarcinoma is NSCLC.

In some embodiments, the cancer is thyroid cancer, e.g., medullary thyroid cancer, and the RET-altered cell, cancer, gene, or gene product comprises a C634W mutation.

In some embodiments, the cancer is leukemia and the RET-altered cell, cancer, gene, or gene product comprises a KIF5B-RET fusion.

In some embodiments, the cancer is thyroid cancer and the RET-altered cell, cancer, gene, or gene product comprises a M918T mutation. In some embodiments, the cancer is medullary thyroid cancer and the RET-altered cell, cancer, gene, or gene product comprises a M918T mutation.

In some embodiments, the cancer is leukemia and the RET-altered cell, cancer, gene, or gene product comprises KIF5B-RET (V804L) or KIF5B-RET (V804M) fusion.

In some embodiments, the cancer is thyroid cancer and the RET-altered cell, cancer, gene, or gene product comprises a CCDC6-RET fusion. In some embodiments, the cancer is colorectal cancer and the RET-altered cell, cancer, gene, or gene product comprises CCDC6-RET fusion. In some embodiments, the cancer is colorectal cancer and the RET-altered cell, cancer, gene, or gene product comprises CCDC6-RET (V804M) fusion.

In some embodiments of any of the methods and uses herein, the compound or pharmaceutical composition has a lower $IC_{50}$ for RET than for KDR, e.g., has a KDR/RET $IC_{50}$ ratio of at least 3×, 4×, 5×, 10×, 20×, 50×, or 100×, and optionally up to 50× or 100×. In some embodiments, the compound or pharmaceutical composition has a KDR/RET $IC_{50}$ ratio of between 3×-4×, 4×-5×, 5×-10×, 10×-20×, 20×-50×, or 50×-100×. In some embodiments, the compound or pharmaceutical composition has a similar $IC_{50}$ for wild-type RET compared to mutant RET (e.g., for V804L RET or V804E RET), e.g., has a wild-type/mutant $IC_{50}$ ratio of no more than 3×, 2×, 1.5×, 1×, or 0.5×, e.g., of between 3× and 0.5×.

In some embodiments of any of the methods and uses herein, the subject does not develop a RET-altered cell, cancer, gene, or gene product for at least 1, 2, 3, 6, 9, 12, 24, or 36 months after initiation of administration of the compound. In some embodiments, the compound is administered as a first line therapy. In some embodiments, the compound is administered to a treatment-naïve subject. In some embodiments, the compound is not administered in combination with another kinase inhibitor. In some embodiments, the compound is not administered in combination with another RET inhibitor. For example, the compound can be administered as a monotherapy or in combination with one or other agents which are not kinase inhibitors, e.g., not RET inhibitors.

In some embodiments of any of the methods and uses herein, the compound is administered at an amount sufficient to reach at least 70%, 80%, 90%, or 95% inhibition of RET in vivo.

EMBODIMENTS OF THE DISCLOSURE

Definitions

As used herein, the terms a "patient," "subject," "individual," and "host" refer to either a human or a non-human animal suffering from or suspected of suffering from a disease or disorder associated with aberrant RET expression (i.e., increased RET activity caused by signaling through RET) or biological activity.

"Treat" and "treating" such a disease or disorder refers to ameliorating at least one symptom of the disease or disorder. These terms, when used in connection with a condition such as a cancer, refer to one or more of: impeding growth of the cancer, causing the cancer to shrink by weight or volume, extending the expected survival time of the patient, inhibiting tumor growth, reducing tumor mass, reducing size or number of metastatic lesions, inhibiting the development of new metastatic lesions, prolonging survival, prolonging progression-free survival, prolonging time to progression, and/or enhancing quality of life.

The term "preventing" when used in relation to a condition or disease such as cancer, refers to a reduction in the frequency of, or delay in the onset of, symptoms of the condition or disease. Thus, prevention of cancer includes, for example, reducing the number of detectable cancerous growths in a population of patients receiving a prophylactic treatment relative to an untreated control population, and/or delaying the appearance of detectable cancerous growths in a treated population versus an untreated control population, e.g., by a statistically and/or clinically significant amount.

The term "therapeutic effect" refers to a beneficial local or systemic effect in animals, particularly mammals, and more particularly humans, caused by administration of a compound or composition of the disclosure. The phrase "therapeutically-effective amount" means that amount of a compound or composition of the disclosure that is effective to treat a disease or condition caused by over expression of RET or aberrant RET biological activity at a reasonable benefit/risk ratio. The therapeutically effective amount of such substance will vary depending upon the subject and disease or condition being treated, the weight and age of the subject, the severity of the disease condition, the manner of administration and the like, which can readily be determined by one of skill in the art.

As used herein, "developing resistance" means that when a drug is first administered to the patient, the patient's symptoms improve, whether measured by decrease in tumor volume, a decrease in the number of new lesions, or some other means that a physician uses to judge disease progression; however, those symptoms stop improving, or even worsen at some point. At that time, the patient is said to have developed resistance to the drug.

"Alteration" as used herein, of a gene or gene product (e.g., the RET gene or gene product) refers to the presence of a mutation or mutations within the gene or gene product, e.g., a mutation, which of the gene or gene product, as compared to the normal or wild-type gene. The alteration can be in amount, structure, and/or activity in a cancer tissue or cancer cell, as compared to its amount, structure, and/or activity, in a normal or healthy tissue or cell (e.g., a control), and is associated with a disease or condition, such as cancer. For example, an alteration which is associated with cancer, or predictive of responsiveness to an anti-cancer therapeutic, can have an altered nucleotide sequence (e.g., a mutation), amino acid sequence, chromosomal translocation, intra-chromosomal inversion, copy number, expression level, protein level, protein activity, or methylation status, in a cancer tissue or cancer cell, as compared to a normal, healthy tissue or cell. Exemplary mutations include, but are not limited to, point mutations (e.g., silent, missense, or nonsense), deletions, insertions, inversions, linking mutations, duplications, translocations, inter- and intra-chromosomal rearrangements. Mutations can be present in the coding or non-coding region of the gene, e.g., a 3' UTR or 5' UTR.

A subject having "altered RET" refers to a subject comprising a RET alteration, e.g., in one or more of their cancer cells.

A "RET-altered" cell, cancer, gene, or gene product refers to a cell, cancer, gene, or gene product comprising a RET alteration as described herein.

"Aliphatic group" means a straight-chain, branched-chain, or cyclic hydrocarbon group and includes saturated and unsaturated groups, such as an alkyl group, an alkenyl group, and an alkynyl group.

"Alkylene" refers to a divalent radical of an alkyl group, e.g., —CH$_2$—, —CH$_2$CH$_2$—, and —CH$_2$CH$_2$CH$_2$—.

"Alkenyl" means an aliphatic group containing at least one double bond.

"Alkoxyl" or "alkoxy" means an alkyl group having an oxygen radical attached thereto. Representative alkoxyl groups include methoxy, ethoxy, propyloxy, tert-butoxy and the like. The term "haloalkoxy" refers to an alkoxy in which one or more hydrogen atoms are replaced by halo, and includes alkoxy moieties in which all hydrogens have been replaced by halo (e.g., perfluoroalkoxy).

"Alkyl" refers to a monovalent radical of a saturated straight or branched hydrocarbon, such as a straight or branched group of 1-12, 1-10, or 1-6 carbon atoms, referred to herein as $C_1$-$C_{12}$ alkyl, $C_1$-$C_{10}$ alkyl, and $C_1$-$C_6$ alkyl, respectively. Exemplary alkyl groups include, but are not limited to, methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, heptyl, octyl, etc.

"Alkenylene" refers to an alkenyl group having two connecting points. For example, "ethenylene" represents the group —CH=CH—. Alkenylene groups can also be in an unsubstituted form or substituted form with one or more substituents.

"Alkynyl" refers to a straight or branched hydrocarbon chain containing 2-12 carbon atoms and characterized in having one or more triple bonds. Examples of alkynyl groups include, but are not limited to, ethynyl, propargyl, and 3-hexynyl. One of the triple bond carbons may optionally be the point of attachment of the alkynyl substituent.

"Alkynylene" refers to an alkynyl having two connecting points. For example, "ethynylene" represents the group —C≡C—. Alkynylene groups can also be in an unsubstituted form or substituted form with one or more substituents.

"Hydroxyalkylene" or "hydroxyalkyl" refers to an alkylene or alkyl moiety in which an alkylene or alkyl hydrogen atom is replaced by a hydroxyl group. Hydroxyalkylene or hydroxyalkyl includes groups in which more than one hydrogen atom has been replaced by a hydroxyl group.

"Aromatic ring system" is art-recognized and refers to a monocyclic, bicyclic or polycyclic hydrocarbon ring system, wherein at least one ring is aromatic.

"Aryl" refers to a monovalent radical of an aromatic ring system. Representative aryl groups include fully aromatic ring systems, such as phenyl, naphthyl, and anthracenyl, and ring systems where an aromatic carbon ring is fused to one or more non-aromatic carbon rings, such as indanyl, phthalimidyl, naphthimidyl, or tetrahydronaphthyl, and the like.

"Arylalkyl" or "aralkyl" refers to an alkyl moiety in which an alkyl hydrogen atom is replaced by an aryl group. Aralkyl includes groups in which more than one hydrogen atom has been replaced by an aryl group. Examples of "arylalkyl" or "aralkyl" include benzyl, 2-phenylethyl, 3-phenylpropyl, 9-fluorenyl, benzhydryl, and trityl groups.

"Aryloxy" refers to —O-(aryl), wherein the aryl moiety is as defined herein.

"Halo" refers to a radical of any halogen, e.g., —F, —Cl, —Br, or —I.

"Haloalkyl" and "haloalkoxy" refers to alkyl and alkoxy structures that are substituted with one or more halo groups or with combinations thereof. For example, the terms "fluoroalkyl" and "fluoroalkoxy" include haloalkyl and haloalkoxy groups, respectively, in which the halo is fluorine. "Haloalkylene" refers to a divalent alkyl, e.g., —CH$_2$—, —CH$_2$CH$_2$—, and —CH$_2$CH$_2$CH$_2$—, in which one or more hydrogen atoms are replaced by halo, and includes alkyl moieties in which all hydrogens have been replaced by halo.

"Heteroalkyl" refers to an optionally substituted alkyl, which has one or more skeletal chain atoms selected from an atom other than carbon, e.g., oxygen, nitrogen, sulfur, phosphorus or combinations thereof. A numerical range may be given, e.g. $C_1$-$C_6$ heteroalkyl which refers to the number of carbons in the chain, which in this example includes 1 to 6 carbon atoms. For example, a —CH$_2$OCH$_2$CH$_3$ radical is referred to as a "$C_3$" heteroalkyl. Connection to the rest of the molecule may be through either a heteroatom or a carbon in the heteroalkyl chain. "Heteroalkylene" refers to a divalent optionally substituted alkyl, which has one or more skeletal chain atoms selected from an atom other than carbon, e.g., oxygen, nitrogen, sulfur, phosphorus or combinations thereof.

"Carbocyclic ring system" refers to a monocyclic, bicyclic or polycyclic hydrocarbon ring system, wherein each ring is either completely saturated or contains one or more units of unsaturation, but where no ring is aromatic.

"Carbocyclyl" refers to a monovalent radical of a carbocyclic ring system. Representative carbocyclyl groups include cycloalkyl groups (e.g., cyclobutyl, cyclopentyl, cyclohexyl and the like), and cycloalkenyl groups (e.g., cyclopentenyl, cyclohexenyl, cyclopentadienyl, and the like).

"Cycloalkyl" refers to a cyclic, bicyclic, tricyclic, or polycyclic non-aromatic hydrocarbon groups having 3 to 12 carbons. Any substitutable ring atom can be substituted (e.g., by one or more substituents). The cycloalkyl groups can contain fused or spiro rings. Fused rings are rings that share a common carbon atom. Examples of cycloalkyl moieties include, but are not limited to, cyclopropyl, cyclohexyl, methylcyclohexyl, adamantyl, and norbornyl.

"Cycloalkylalkyl" refers to a -(cycloalkyl)-alkyl radical where cycloalkyl and alkyl are as disclosed herein. The "cycloalkylalkyl" is bonded to the parent molecular structure through the alkyl group.

"Heteroaromatic ring system" is art-recognized and refers to monocyclic, bicyclic or polycyclic ring system wherein at least one ring is both aromatic and comprises at least one heteroatom (e.g., N, O or S); and wherein no other rings are heterocyclyl (as defined below). In certain instances, a ring which is aromatic and comprises a heteroatom contains 1, 2, 3, or 4 ring heteroatoms in such ring.

"Heteroaryl" refers to a monovalent radical of a heteroaromatic ring system. Representative heteroaryl groups include ring systems where (i) each ring comprises a heteroatom and is aromatic, e.g., imidazolyl, oxazolyl, thiazolyl, triazolyl, pyrrolyl, furanyl, thiophenyl pyrazolyl, pyridinyl, pyrazinyl, pyridazinyl, pyrimidinyl, indolizinyl, purinyl, naphthyridinyl, and pteridinyl; (ii) each ring is aromatic or carbocyclyl, at least one aromatic ring comprises a heteroatom and at least one other ring is a hydrocarbon ring or e.g., indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, carbazolyl, acridinyl, phenazinyl, phenothiazinyl, phenoxazinyl, pyrido[2,3-b]-1,4-oxazin-3-(4H)-one, 5,6,7,8-tetrahydroquinolinyl and 5,6,7,8-tetrahydroisoquinolinyl; and (iii) each ring is aromatic or carbocyclyl, and at least one aromatic ring shares a bridgehead heteroatom with another aromatic ring, e.g., 4H-quinolizinyl.

"Heterocyclic ring system" refers to monocyclic, bicyclic and polycyclic ring systems where at least one ring is saturated or partially unsaturated (but not aromatic) and comprises at least one heteroatom. A heterocyclic ring system can be attached to its pendant group at any heteroatom or carbon atom that results in a stable structure and any of the ring atoms can be optionally substituted.

"Heterocyclyl" refers to a monovalent radical of a heterocyclic ring system. Representative heterocyclyls include ring systems in which (i) every ring is non-aromatic and at least one ring comprises a heteroatom, e.g., tetrahydrofuranyl, tetrahydropyranyl, tetrahydrothienyl, pyrrolidinyl, pyrrolidonyl, piperidinyl, pyrrolinyl, decahydroquinolinyl, oxazolidinyl, piperazinyl, dioxanyl, dioxolanyl, diazepinyl, oxazepinyl, thiazepinyl, morpholinyl, and quinuclidinyl; (ii) at least one ring is non-aromatic and comprises a heteroatom and at least one other ring is an aromatic carbon ring, e.g., 1,2,3,4-tetrahydroquinolinyl, 1,2,3,4-tetrahydroisoquinolinyl; and (iii) at least one ring is non-aromatic and comprises a heteroatom and at least one other ring is aromatic and comprises a heteroatom, e.g., 3,4-dihydro-1H-pyrano[4,3-c]pyridine, and 1,2,3,4-tetrahydro-2,6-naphthyridine. In some embodiments, heterocyclyl can include:

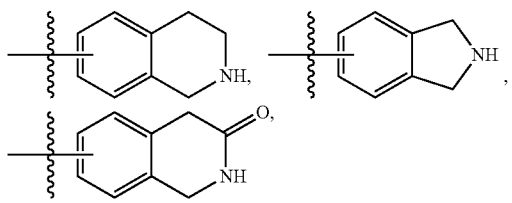

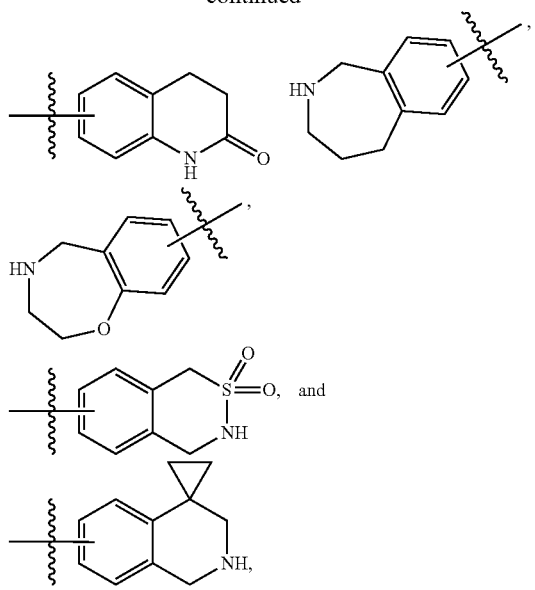

wherein the point of attachment to the base structure can be through any of the atoms on the heterocyclyl, e.g., through a carbon atom or a nitrogen atom of the heterocyclyl.

"Heterocyclylalkyl" refers to an alkyl group substituted with a heterocyclyl group. The "heterocyclylalkyl" is bonded to the parent molecular structure through the alkyl group.

"Cyano" refers to a —CN radical.

"Nitro" refers to —NO$_2$.

"Hydroxy" or "hydroxyl" refers to —OH.

"Hydroxyalkylene" refers to a divalent alkyl, e.g., —CH$_2$—, —CH$_2$CH$_2$—, and —CH$_2$CH$_2$CH$_2$—, in which one or more hydrogen atoms are replaced by a hydroxy, and includes alkyl moieties in which all hydrogens have been replaced by hydroxy.

"Substituted", whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at each position. Combinations of substituents envisioned under this disclosure are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

As used herein, the definition of each expression, e.g., alkyl, m, n, etc., when it occurs more than once in any structure, is intended to be independent of its definition elsewhere in the same structure.

Certain compounds of the present disclosure may exist in particular geometric or stereoisomeric forms. The present disclosure contemplates all such compounds, including cis- and trans-isomers, R- and S-enantiomers, diastereomers, (D)-isomers, (L)-isomers, the racemic mixtures thereof, and other mixtures thereof, as falling within the scope of the disclosure. Additional asymmetric carbon atoms may be present in a substituent such as an alkyl group. All such isomers, as well as mixtures thereof, are intended to be included in this disclosure.

If, for instance, a particular enantiomer of compound of the present disclosure is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

Unless otherwise indicated when a disclosed compound is named or depicted by a structure without specifying the stereochemistry and has one or more chiral centers, it is understood to represent all possible stereoisomers of the compound, as well as enantiomeric mixtures thereof.

The "enantiomeric excess" or "% enantiomeric excess" of a composition can be calculated using the equation shown below. In the example shown below a composition contains 90% of one enantiomer, e.g., the S enantiomer, and 10% of the other enantiomer, i.e., the R enantiomer.

$$ee=(90-10)/100=80\%.$$

Thus, a composition containing 90% of one enantiomer and 10% of the other enantiomer is said to have an enantiomeric excess of 80%.

The compounds or compositions described herein may contain an enantiomeric excess of at least 50%, 75%, 90%, 95%, or 99% of one form of the compound, e.g., the S-enantiomer. In other words such compounds or compositions contain an enantiomeric excess of the S enantiomer over the R enantiomer.

The compounds described herein may also contain unnatural proportions of atomic isotopes at one or more of the atoms that constitute such compounds. For example, the compounds may be radiolabeled with radioactive isotopes, such as for example deuterium ($^2H$), tritium ($^3H$), carbon-13 ($^{13}C$), or carbon-14 ($^{14}C$). All isotopic variations of the compounds disclosed herein, whether radioactive or not, are intended to be encompassed within the scope of the present disclosure. In addition, all tautomeric forms of the compounds described herein are intended to be within the scope of the disclosure.

The compound can be useful as the free base or as a salt. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge et al. (1977) "Pharmaceutical Salts", *J. Pharm. Sci.* 66:1-19.)

Compounds

In one aspect, the disclosure features a compound having the structural formula (I):

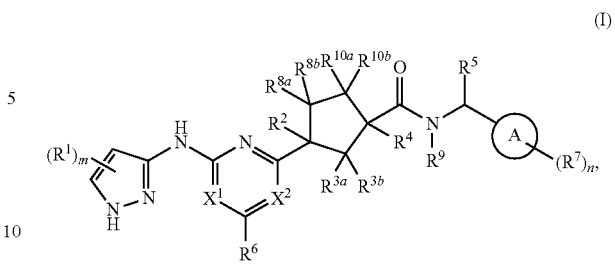

or a stereoisomer thereof, of a pharmaceutically acceptable salt of either of the foregoing, wherein: ring A is an aryl or heteroaryl ring; each of $X^1$ and $X^2$ is independently selected from N and $C(R^{6'})$; each $R^1$ and each $R^7$ is independently selected from $C_1$-$C_6$ alkyl, $C_2$-$C_6$ alkenyl, $C_2$-$C_6$ alkynyl, $C_1$-$C_6$ alkoxy, halo, $C_1$-$C_6$ heteroalkyl, cycloalkyl, aryl, heteroaryl, aryloxy, aralkyl, heterocyclyl, heterocyclylalkyl, nitro, cyano, —C(O)$R^c$, —OC(O)$R^c$, —C(O)O$R^d$, —($C_1$-$C_6$ alkylene)-C(O)$R^c$, —S$R^d$, —S(O)$_2R^c$, —S(O)$_2$—N($R^d$)($R^d$), —($C_1$-$C_6$ alkylene)-S(O)$_2R^c$, —($C_1$-$C_6$ alkylene)-S(O)$_2$—N($R^d$)($R^d$), —N($R^d$)($R^d$), —C(O)—N($R^d$)($R^d$), —N($R^d$)—C(O)$R^c$, —N($R^d$)—C(O)O$R^c$, —($C_1$-$C_6$ alkylene)-N($R^d$)—C(O)$R^c$, —N($R^d$)S(O)$_2R^c$, and —P(O)($R^c$)($R^c$); wherein each of alkyl, alkenyl, alkynyl, alkoxy, heteroalkyl, cycloalkyl, aryl, heteroaryl, aryloxy, aralkyl, heterocyclyl, and heterocyclylalkyl is independently substituted with 0-5 occurrences of $R^a$; or two $R^1$ or two $R^7$ are taken together with the carbon atoms to which they are attached form a cycloalkyl or heterocyclyl ring independently substituted with 0-5 occurrences of $R^b$; each of $R^2$, $R^{3a}$, $R^{3b}$, $R^4$, $R^{8a}$, $R^{8b}$, $R^{10a}$ and $R^{10b}$ is independently selected from hydrogen, $C_1$-$C_6$ alkyl, $C_1$-$C_6$ alkoxy, halo, hydroxyl, cyano, $C_1$-$C_6$ heteroalkyl, and —N($R^d$)($R^d$); wherein each of alkyl, alkoxy, and heteroalkyl is optionally and independently substituted with 0-5 occurrences of $R^a$; each of $R^5$ and $R^9$ is independently selected from hydrogen, $C_1$-$C_6$ alkyl, and $C_1$-$C_6$ heteroalkyl; wherein each alkyl and heteroalkyl is optionally and independently substituted with 0-5 occurrences of $R^a$; $R^6$ and each $R^{6'}$ is independently selected from hydrogen, $C_1$-$C_6$ alkyl, $C_1$-$C_6$ alkoxy, halo, cyano, $C_1$-$C_6$ heteroalkyl, and —N($R^d$)($R^d$); wherein each alkyl, alkoxy, and heteroalkyl is optionally and independently substituted with 0-5 occurrences of $R^a$; each $R^a$ and each $R^b$ is independently selected from $C_1$-$C_6$ alkyl, halo, hydroxyl, $C_1$-$C_6$ heteroalkyl, $C_1$-$C_6$ alkoxy, cycloalkyl, heterocyclyl, or cyano, wherein each of alkyl, heteroalkyl, alkoxy, cycloalkyl and heterocyclyl is independently substituted with 0-5 occurrences of R'; each R' is independently selected from $C_1$-$C_6$ alkyl, $C_1$-$C_6$ heteroalkyl, halo, hydroxyl, cycloalkyl or cyano; or two R' together with the atom(s) to which they are attached form a cycloalkyl or heterocyclyl ring; each $R^c$ is independently selected from hydrogen, hydroxyl, halo, thiol, $C_1$-$C_6$ alkyl, $C_1$-$C_6$ thioalkyl, $C_1$-$C_6$ alkoxy, $C_1$-$C_6$ heteroalkyl, cycloalkyl, cycloalkylalkyl, heteroarylalkyl, heterocyclyl, and heterocyclylalkyl, wherein each of alkyl, thioalkyl, alkoxy, heteroalkyl, cycloalkyl, cycloalkylalkyl, heteroarylalkyl, heterocyclyl, and heterocyclylalkyl is independently substituted with 0-5 occurrences of $R^a$, or two $R^c$ together with the atom(s) to which they are attached form a cycloalkyl or heterocyclyl ring independently substituted with 0-5 occurrences of $R^b$; each $R^d$ is independently selected from hydrogen, $C_1$-$C_6$ alkyl, $C_1$-$C_6$ heteroalkyl, cycloalkyl, cycloalkylalkyl, heteroarylalkyl, heterocyclyl, and heterocyclylalkyl, wherein each of alkyl, heteroalkyl, cycloalkyl, cycloalkylalkyl, heteroarylalkyl, heterocyclyl, and heterocyclylalkyl is independently substituted with 0-5 occurrences of $R^a$, or two $R^d$ together with the atom(s) to which they are attached form a cycloalkyl or heterocyclyl ring independently substituted with 0-5 occurrences of $R^b$; m is 0, 1, or 2; and n is 0, 1, 2, or 3.

In some embodiments, the compound has the structural formula (Ia):

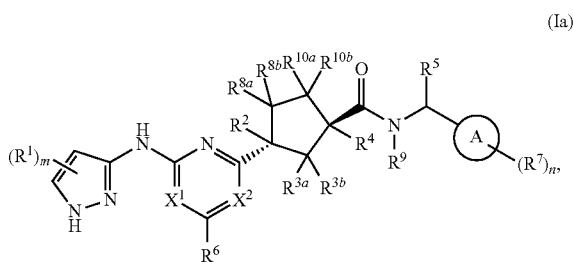

(Ia)

or a pharmaceutically acceptable salt thereof, wherein ring A, $X^1$, $X^2$, $R^1$, $R^2$, $R^{3a}$, $R^{3b}$, $R^4$, $R^5$, $R^6$, $R^7$, $R^{8a}$, $R^{8b}$, $R^9$, $R^{10a}$, $R^{10b}$, m and n are as defined herein.

In some embodiments, the compound has the structural formula (Ib):

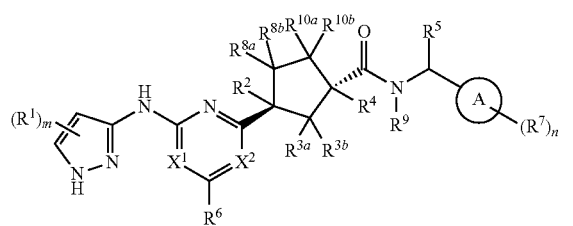

(Ib)

or a pharmaceutically acceptable salt thereof, wherein ring A, $X^1$, $X^2$, $R^1$, $R^2$, $R^{3a}$, $R^{3b}$, $R^4$, $R^5$, $R^6$, $R^7$, $R^{8a}$, $R^{8b}$, $R^9$, m and n are as defined herein.

In some embodiments, m is 1; $R^1$ is located at the 5-position; and $R^1$ is selected $C_1$-$C_4$ alkyl or $C_3$-$C_6$ cycloalkyl, wherein $R^1$ is substituted with 0-3 occurrences of $R^a$.

In some embodiments, $R^1$ is —$CH_3$ or cyclopropyl.

In some embodiments, $R^2$ is hydrogen or hydroxyl.

In some embodiments, each of $R^{3a}$, $R^{3b}$, $R^{8a}$, $R^{8b}$, $R^{10a}$ and $R^{10b}$ is hydrogen.

In some embodiments, $R^4$ is hydrogen or $C_1$-$C_4$ alkyl, substituted with 0-3 occurrences of $R^a$. In some embodiments, $R^4$ is hydrogen or —$CH_3$.

In some embodiments, $R^5$ is hydrogen or $C_1$-$C_4$ alkyl substituted with 0-3 occurrences of $R^a$. In some embodiments, $R^5$ is hydrogen or —$CH_3$.

In some embodiments, $R^6$ is $C_1$-$C_4$ alkyl substituted with 0-3 occurrences of $R^a$. In some embodiments, each $R^6$ is —$CH_3$.

In some embodiments, each $R^{6'}$ is hydrogen.

In some embodiments, ring A is a 6-membered monocyclic heteroaryl comprising at least one nitrogen ring atom or phenyl. In some embodiments, ring A is selected from:

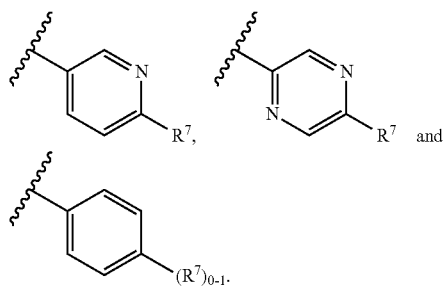

In some embodiments, n is 0 or 1; and $R^7$, if present, is selected from pyrazol-1-yl substituted with 0-3 occurrences of $R^b$, and —O—$C_1$-$C_4$ alkyl substituted with 0-3 occurrences of $R^a$.

In some embodiments, $R^7$ is selected from 4-fluoropyrazol-1-yl, 4-chloropyrazol-1-yl, 3,5-dimethylpyrazol-1-yl, pyrazol-1-yl and —$OCH_2CH_3$, or $R^7$ is absent.

In some embodiments, $R^9$ is hydrogen.

In some embodiments, $X^1$ is $C(R^{6'})$ and $X^2$ is N. In some embodiments, $X^1$ is $C(R^{6'})$ and $X^2$ is $C(R^{6'})$.

In one aspect, the disclosure features a compound having the structural formula (II):

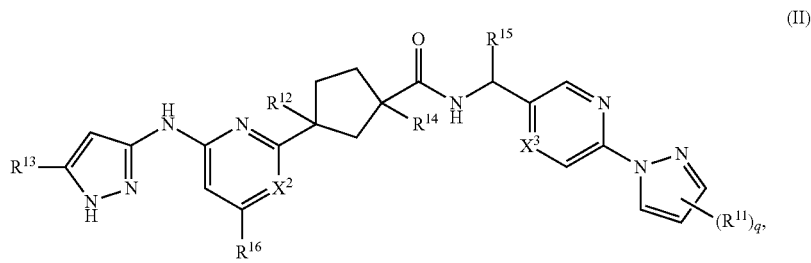

(II)

or a stereoisomer thereof, or a pharmaceutically acceptable salt of either of the foregoing, wherein: $X^2$ is selected from N and CH; $X^3$ is selected from N and CH; each $R^{11}$, if present, is independently selected from halo and —$C_1$-$C_4$ alkyl substituted with 0-3 occurrences of $R^a$; $R^{12}$ is hydrogen or hydroxyl; $R^{13}$ is selected from $C_1$-$C_4$ alkyl or $C_3$-$C_6$ cycloalkyl, wherein $R^{13}$ is substituted with 0-3 occurrences of $R^a$; $R^{14}$ is selected from hydrogen and —$C_1$-$C_4$ alkyl substituted with 0-3 occurrences of $R^a$; $R^{15}$ is selected from hydrogen and —$C_1$-$C_4$ alkyl substituted with 0-3 occurrences of $R^a$; $R^{16}$ is selected from hydrogen and —$C_1$-$C_4$ alkyl substituted with 0-3 occurrences of $R^a$; q is 0, 1 or 2; each $R^a$ is independently selected from $C_1$-$C_6$ alkyl, halo, hydroxyl, $C_1$-$C_6$ heteroalkyl, $C_1$-$C_6$ alkoxy, cycloalkyl, heterocyclyl, or cyano, wherein each of alkyl, heteroalkyl, alkoxy, cycloalkyl and heterocyclyl is independently substituted with 0-5 occurrences of R'; and each R' is independently selected from $C_1$-$C_6$ alkyl, $C_1$-$C_6$ heteroalkyl, halo, hydroxyl, cycloalkyl or cyano; or two R' together with the atom(s) to which they are attached form a cycloalkyl or heterocyclyl ring.

In some embodiments, each $R^{11}$, if present, is independently selected from fluoro and —$CH_3$; $R^{13}$ is selected from —$CH_3$ and cyclopropyl; $R^{14}$ is selected from hydrogen and —$CH_3$; $R^{15}$ is selected from hydrogen and —$CH_3$; and $R^{16}$ is —$CH_3$.

In one aspect, the disclosure features a compound having the structural formula (III):

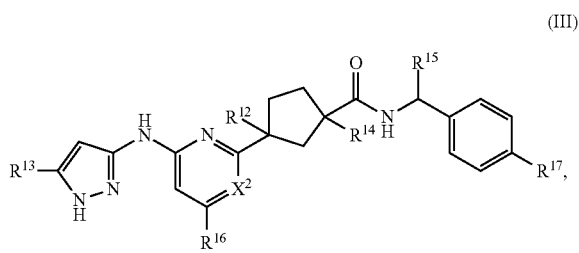

(III)

or a stereoisomer thereof, or a pharmaceutically acceptable salt of either of the foregoing, wherein: $X^2$ is selected from N and CH; $R^{12}$ is hydrogen or hydroxyl; $R^{13}$ is selected from $C_1$-$C_4$ alkyl or $C_3$-$C_6$ cycloalkyl, wherein $R^{13}$ is substituted with 0-3 occurrences of $R^a$; $R^{14}$ is selected from hydrogen and —$C_1$-$C_4$ alkyl substituted with 0-3 occurrences of $R^a$; $R^{15}$ is selected from hydrogen and —$C_1$-$C_4$ alkyl substituted with 0-3 occurrences of $R^a$; $R^{16}$ is selected from hydrogen and —$C_1$-$C_4$ alkyl substituted with 0-3 occurrences of $R^a$; $R^{17}$ is selected from hydrogen, —$C_1$-$C_4$ alkyl substituted with 0-3 occurrences of $R^a$, or O—$C_1$-$C_4$ alkyl substituted with 0-3 occurrences of $R^a$; each $R^a$ is independently selected from $C_1$-$C_6$ alkyl, halo, hydroxyl, $C_1$-$C_6$ heteroalkyl, $C_1$-$C_6$ alkoxy, cycloalkyl, heterocyclyl, or cyano, wherein each of alkyl, heteroalkyl, alkoxy, cycloalkyl and heterocyclyl is independently substituted with 0-5 occurrences of R'; and each R' is independently selected from $C_1$-$C_6$ alkyl, $C_1$-$C_6$ heteroalkyl, halo, hydroxyl, cycloalkyl or cyano; or two R' together with the atom(s) to which they are attached form a cycloalkyl or heterocyclyl ring.

In some embodiments, $R^{13}$ is selected from —$CH_3$ and cyclopropyl; $R^{14}$ is selected from hydrogen and —$CH_3$; $R^{15}$ is selected from hydrogen and —$CH_3$; $R^{16}$ is —$CH_3$; and $R^{17}$ is selected from hydrogen and —$OCH_3$.

Table 1 below shows the structures of exemplary compounds of the disclosure.

TABLE 1

Exemplary Compounds

| Compound # | Structure |
|---|---|
| 100 | 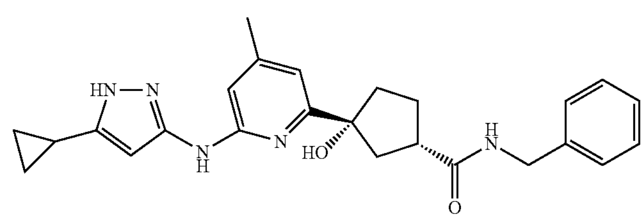 [SMILES: Cc1cc(Nc2cc(C3CC3)[nH]n2)nc([C@@]2(O)CC[C@H](C(=O)NCc3ccccc3)C2)c1] |
| 101 | 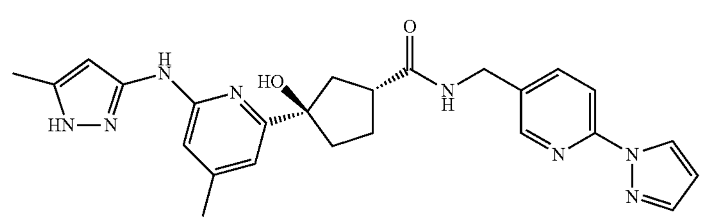 [SMILES: Cc1cc(Nc2cc(C)[nH]n2)nc([C@@]2(O)CC[C@@H](C(=O)NCc3ccc(-n4cccn4)nc3)C2)c1] |
| 102 | 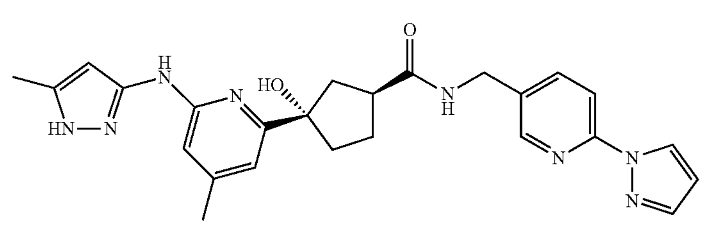 [SMILES: Cc1cc(Nc2cc(C)[nH]n2)nc([C@]2(O)CC[C@H](C(=O)NCc3ccc(-n4cccn4)nc3)C2)c1] |

TABLE 1-continued

Exemplary Compounds

| Compound # | Structure |
|---|---|
| 103 | 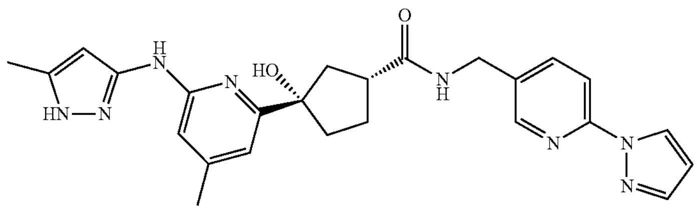 [SMILES: Cc1cc(Nc2cc(C)[nH]n2)nc([C@]2(O)CC[C@@H](C(=O)NCc3ccc(-n4cccn4)nc3)C2)c1] |
| 104 | 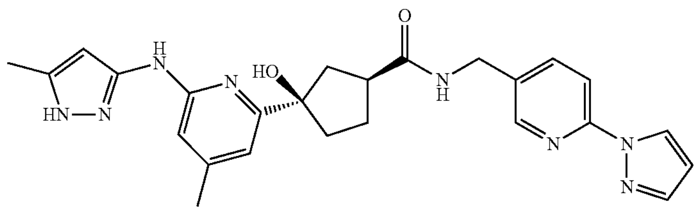 [SMILES: Cc1cc(Nc2cc(C)[nH]n2)nc([C@@]2(O)CC[C@H](C(=O)NCc3ccc(-n4cccn4)nc3)C2)c1] |
| 105 | 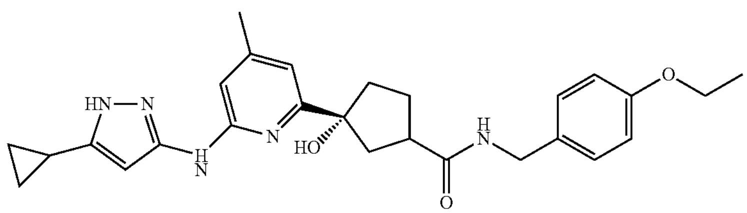 [SMILES: CCOc1ccc(CNC(=O)C2CC[C@](O)(c3cc(C)cc(Nc4cc(C5CC5)[nH]n4)n3)C2)cc1] |
| 106 | 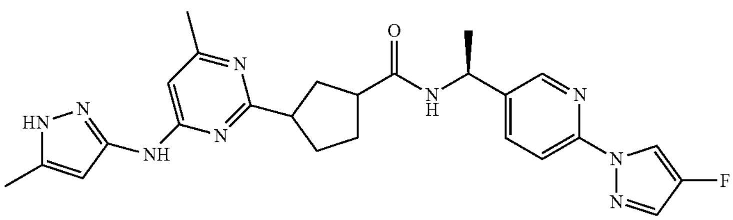 [SMILES: Cc1cc(Nc2cc(C)[nH]n2)nc(C2CCC(C(=O)N[C@@H](C)c3ccc(-n4cc(F)cn4)nc3)C2)n1] |
| 107 | 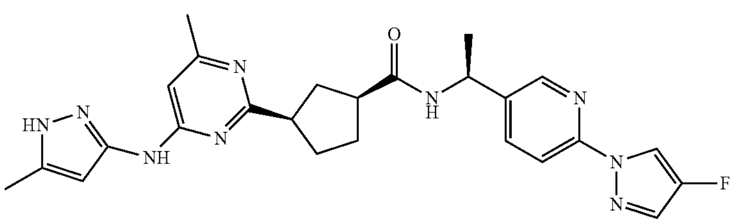 [SMILES: Cc1cc(Nc2cc(C)[nH]n2)nc([C@@H]2CC[C@H](C(=O)N[C@@H](C)c3ccc(-n4cc(F)cn4)nc3)C2)n1] |
| 108 | 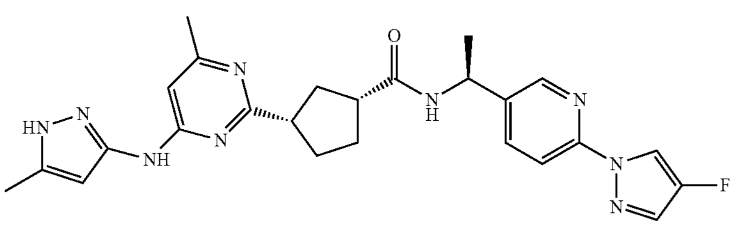 |
| 109 | 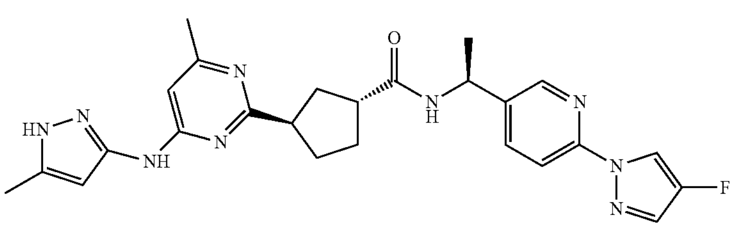 [SMILES: Cc1cc(Nc2cc(C)[nH]n2)nc([C@@H]2CC[C@@H](C(=O)N[C@@H](C)c3ccc(-n4cc(F)cn4)nc3)C2)n1] |

TABLE 1-continued
Exemplary Compounds
| Compound # | Structure |
|---|---|
| 110 | 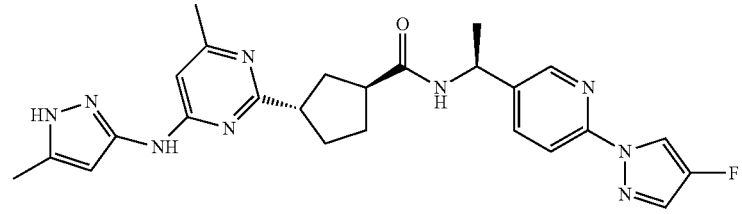 [SMILES: Cc1cc(Nc2cc(C)[nH]n2)nc([C@H]2CC[C@H](C(=O)N[C@@H](C)c3ccc(-n4cc(F)cn4)nc3)C2)n1] |
| 111 | 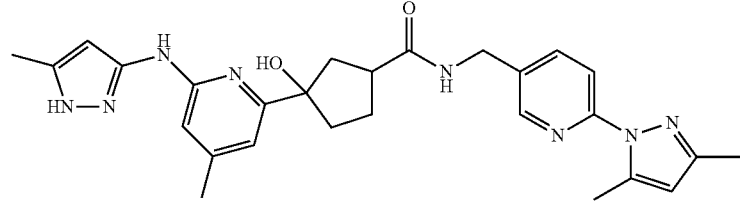 |
| 112 | 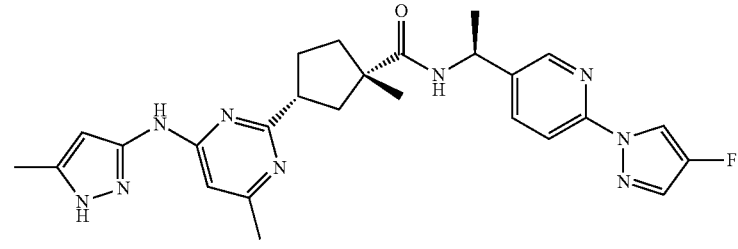 [SMILES: Cc1cc(Nc2cc(C)[nH]n2)nc([C@@H]2CC[C@](C)(C(=O)N[C@@H](C)c3ccc(-n4cc(F)cn4)nc3)C2)n1] |
| 113 | 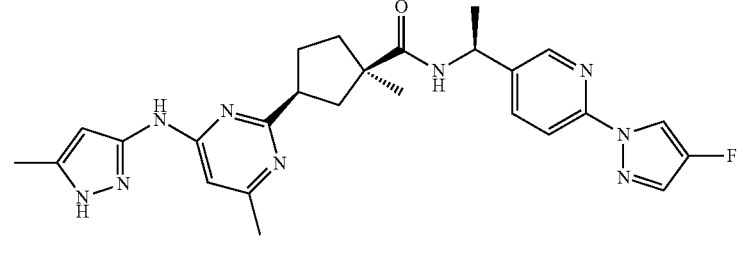 [SMILES: Cc1cc(Nc2cc(C)[nH]n2)nc([C@H]2CC[C@@](C)(C(=O)N[C@@H](C)c3ccc(-n4cc(F)cn4)nc3)C2)n1] |
| 114 | 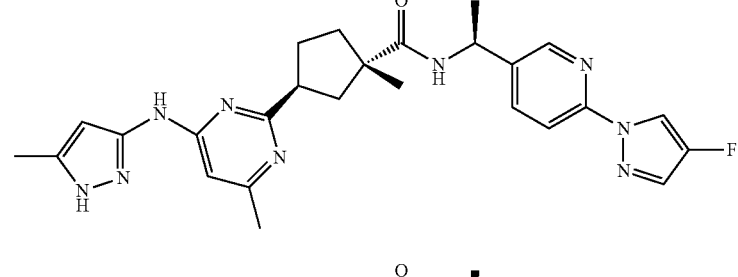 |
| 115 | 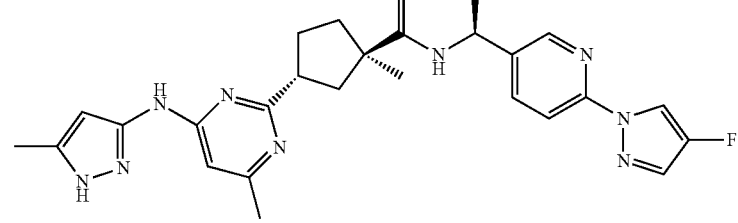 |

TABLE 1-continued

Exemplary Compounds

| Compound # | Structure |
|---|---|
| 116 | 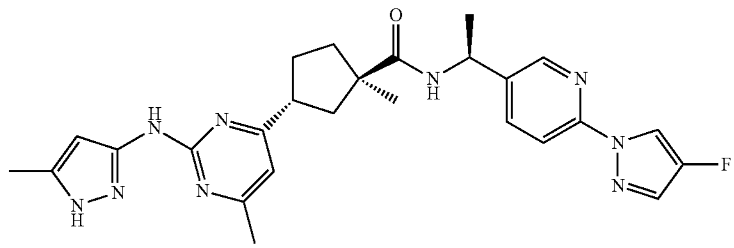 [SMILES: Cc1cc(Nc2cc(C)[nH]n2)nc([C@@H]2CC[C@@](C)(C(=O)N[C@@H](C)c3ccc(-n4cc(F)cn4)nc3)C2)n1] |
| 117 | 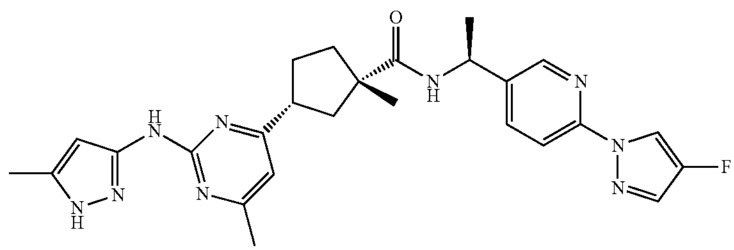 [SMILES: Cc1cc([C@@H]2CC[C@](C)(C(=O)N[C@@H](C)c3ccc(-n4cc(F)cn4)nc3)C2)nc(Nc2cc(C)[nH]n2)n1] |
| 118 | 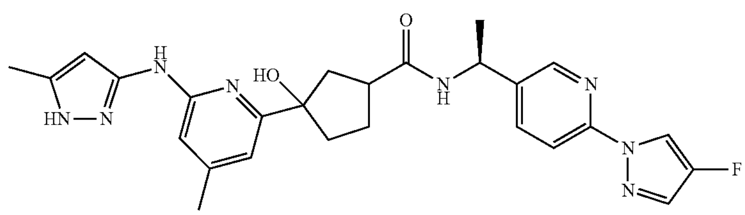 |
| 119 | 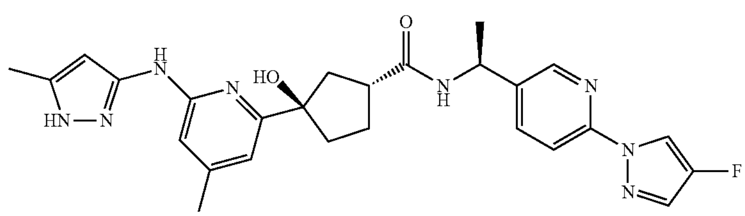 [SMILES: Cc1cc(Nc2cc(C)[nH]n2)nc([C@@]2(O)CC[C@@H](C(=O)N[C@@H](C)c3ccc(-n4cc(F)cn4)nc3)C2)c1] |
| 120 | 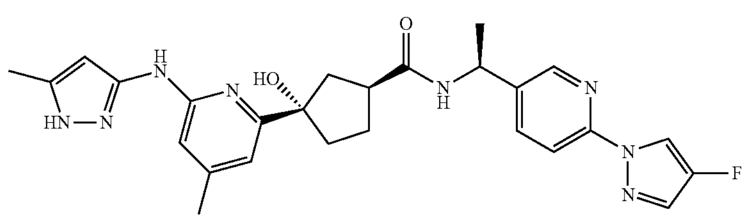 [SMILES: Cc1cc(Nc2cc(C)[nH]n2)nc([C@]2(O)CC[C@H](C(=O)N[C@@H](C)c3ccc(-n4cc(F)cn4)nc3)C2)c1] |
| 121 | 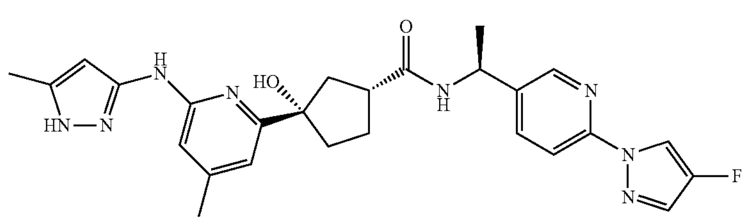 |

TABLE 1-continued

Exemplary Compounds

| Compound # | Structure |
|---|---|
| 122 | 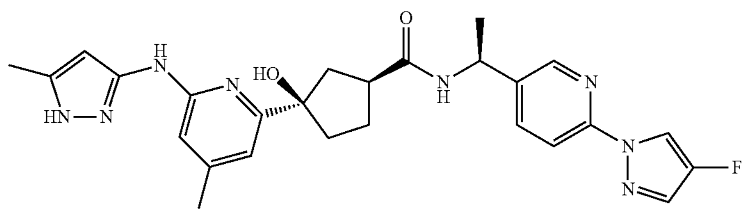 [SMILES: Cc1cc(Nc2cc(C)[nH]n2)nc([C@@]2(O)CC[C@H](C(=O)N[C@@H](C)c3cnc(-n4cc(F)cn4)cn3)C2)c1] |
| 123 | 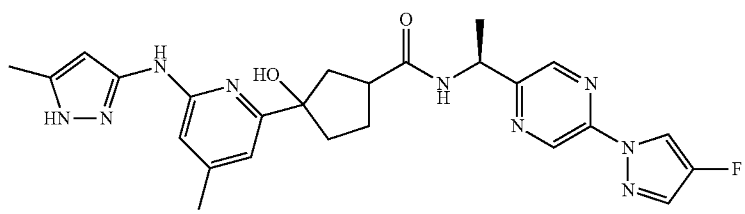 |
| 124 | 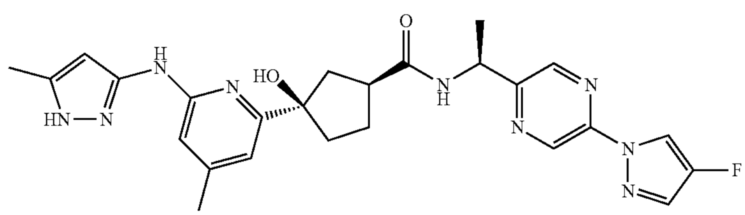 |
| 125 | 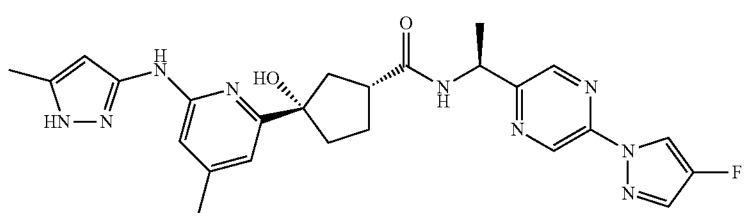 [SMILES: Cc1cc(Nc2cc(C)[nH]n2)nc([C@]2(O)CC[C@@H](C(=O)N[C@@H](C)c3cnc(-n4cc(F)cn4)cn3)C2)c1] |
| 126 | 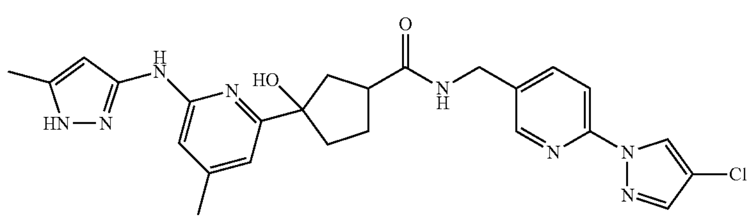 [SMILES: Cc1cc(Nc2cc(C)[nH]n2)nc(C2(O)CCC(C(=O)NCc3ccc(-n4cc(Cl)cn4)nc3)C2)c1] |
| 127 | 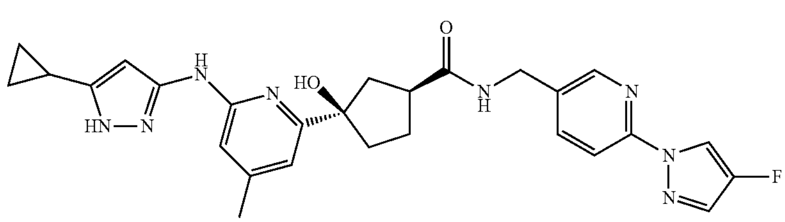 [SMILES: Cc1cc(Nc2cc(C3CC3)[nH]n2)nc([C@@]2(O)CC[C@H](C(=O)NCc3ccc(-n4cc(F)cn4)nc3)C2)c1] |

TABLE 1-continued

Exemplary Compounds

| Compound # | Structure |
|---|---|
| 128 | 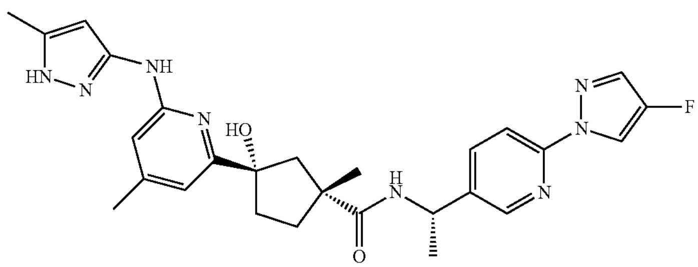 [SMILES: Cc1cc(Nc2cc(C)[nH]n2)nc([C@]2(O)CC[C@@](C)(C(=O)N[C@@H](C)c3ccc(-n4cc(F)cn4)nc3)C2)c1] |
| 129 | 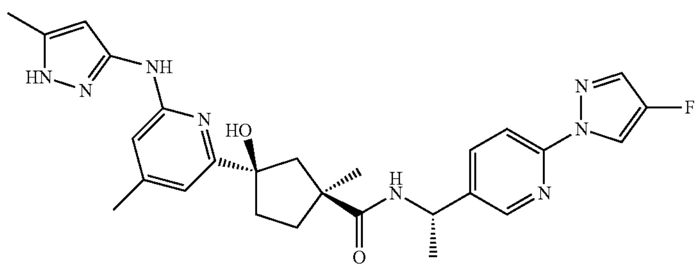 [SMILES: Cc1cc(Nc2cc(C)[nH]n2)nc([C@@]2(O)CC[C@](C)(C(=O)N[C@@H](C)c3ccc(-n4cc(F)cn4)nc3)C2)c1] |

Pharmaceutically acceptable salts of these compounds are also contemplated for the uses described herein.

"Pharmaceutically acceptable salt" refers to any salt of a compound of the disclosure which retains its biological properties and which is not toxic or otherwise undesirable for pharmaceutical use. Pharmaceutically acceptable salts may be derived from a variety of organic and inorganic counter-ions well known in the art and include. Such salts include: (1) acid addition salts formed with organic or inorganic acids such as hydrochloric, hydrobromic, sulfuric, nitric, phosphoric, sulfamic, acetic, trifluoroacetic, trichloroacetic, propionic, hexanoic, cyclopentylpropionic, glycolic, glutaric, pyruvic, lactic, malonic, succinic, sorbic, ascorbic, malic, maleic, fumaric, tartaric, citric, benzoic, 3-(4-hydroxybenzoyl)benzoic, picric, cinnamic, mandelic, phthalic, lauric, methanesulfonic, ethanesulfonic, 1,2-ethane-disulfonic, 2-hydroxyethanesulfonic, benzenesulfonic, 4-chlorobenzenesulfonic, 2-naphthalenesulfonic, 4-toluenesulfonic, camphoric, camphorsulfonic, 4-methylbicyclo[2.2.2]-oct-2-ene-1-carboxylic, glucoheptonic, 3-phenylpropionic, trimethylacetic, tert-butylacetic, lauryl sulfuric, gluconic, benzoic, glutamic, hydroxynaphthoic, salicylic, stearic, cyclohexylsulfamic, quinic, muconic acid and the like acids; or (2) salts formed when an acidic proton present in the parent compound either (a) is replaced by a metal ion, e.g., an alkali metal ion, an alkaline earth ion or an aluminum ion, or alkali metal or alkaline earth metal hydroxides, such as sodium, potassium, calcium, magnesium, aluminum, lithium, zinc, and barium hydroxide, ammonia or (b) coordinates with an organic base, such as aliphatic, alicyclic, or aromatic organic amines, such as ammonia, methylamine, dimethylamine, diethylamine, picoline, ethanolamine, diethanolamine, triethanolamine, ethylenediamine, lysine, arginine, ornithine, choline, N,N'-dibenzylethylene-diamine, chloroprocaine, diethanolamine, procaine, N-benzylphenethylamine, N-methylglucamine piperazine, tris(hydroxymethyl)-aminomethane, tetramethylammonium hydroxide, and the like. Pharmaceutically acceptable salts further include, by way of example only, sodium, potassium, calcium, magnesium, ammonium, tetraalkylammonium and the like, and when the compound contains a basic functionality, salts of non-toxic organic or inorganic acids, such as hydrochloride, hydrobromide, tartrate, mesylate, besylate, acetate, maleate, oxalate and the like.

Pharmaceutical Compositions

Pharmaceutical compositions of the disclosure comprise one or more compounds of the disclosure and one or more physiologically or pharmaceutically acceptable carrier. The term "pharmaceutically acceptable carrier" refers to a pharmaceutically-acceptable material, composition or vehicle, such as a liquid or solid filler, diluent, excipient, solvent or encapsulating material, involved in carrying or transporting any subject composition or component thereof. Each carrier must be "acceptable" in the sense of being compatible with the subject composition and its components and not injurious to the patient. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The compositions of the disclosure may be administered orally, parenterally, by inhalation spray, topically, rectally, nasally, buccally, vaginally or via an implanted reservoir.

The term "parenteral" as used herein includes subcutaneous, intravenous, intramuscular, intra-articular, intra-synovial, intrasternal, intrathecal, intrahepatic, intralesional and intracranial injection or infusion techniques. In some embodiments, the compositions of the disclosure are administered orally, intraperitoneally or intravenously. Sterile injectable forms of the compositions of this disclosure may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tween, Spans and other emulsifying agents or bioavailability enhancers which are commonly used in the manufacture of pharmaceutically acceptable solid, liquid, or other dosage forms may also be used for the purposes of formulation.

The pharmaceutically acceptable compositions of this disclosure may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutically acceptable compositions of this disclosure may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

The pharmaceutically acceptable compositions of this disclosure may also be administered topically, especially when the target of treatment includes areas or organs readily accessible by topical application, including diseases of the eye, the skin, or the lower intestinal tract. Suitable topical formulations are readily prepared for each of these areas or organs. Topical application for the lower intestinal tract can be effected in a rectal suppository formulation (see above) or in a suitable enema formulation. Topically-transdermal patches may also be used.

For topical applications, the pharmaceutically acceptable compositions may be formulated in a suitable ointment containing the active component suspended or dissolved in one or more carriers. Carriers for topical administration of the compounds of this disclosure include, but are not limited to, mineral oil, liquid petrolatum, white petrolatum, propylene glycol, polyoxyethylene, polyoxypropylene compound, emulsifying wax and water. Alternatively, the pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

The pharmaceutically acceptable compositions of this disclosure may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of the compounds of the present disclosure that may be combined with the carrier materials to produce a composition in a single dosage form will vary depending upon the host treated, the particular mode of administration. Preferably, the compositions should be formulated so that a dosage of between 0.01-100 mg/kg body weight/day of the inhibitor can be administered to a patient receiving these compositions.

Dosages

Toxicity and therapeutic efficacy of compounds of the disclosure, including pharmaceutically acceptable salts and deuterated variants, can be determined by standard pharmaceutical procedures in cell cultures or experimental animals. The $LD_{50}$ is the dose lethal to 50% of the population. The $ED_{50}$ is the dose therapeutically effective in 50% of the population. The dose ratio between toxic and therapeutic effects ($LD_{50}/ED_{50}$) is the therapeutic index. Compounds that exhibit large therapeutic indexes are preferred. While compounds that exhibit toxic side effects may be used, care should be taken to design a delivery system that targets such compounds to the site of affected tissue in order to minimize potential damage to uninfected cells and, thereby, reduce side effects.

Data obtained from the cell culture assays and animal studies can be used in formulating a range of dosage for use in humans. The dosage of such compounds may lie within a range of circulating concentrations that include the $ED_{50}$ with little or no toxicity. The dosage may vary within this range depending upon the dosage form employed and the route of administration utilized. For any compound, the therapeutically effective dose can be estimated initially from cell culture assays. A dose may be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma may be measured, for example, by high performance liquid chromatography.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated.

The amount of a compound of the present disclosure in the composition will also depend upon the particular compound in the composition.

Treatment

In one aspect, the disclosure features a method for inhibiting RET activity in a cell or in a subject, comprising the step of contacting the cell or administering to the patient a compound as described herein or a pharmaceutical composition thereof.

In one aspect, the disclosure features a method for treating a subject suffering from a condition mediated by aberrant RET activity, comprising administering to the subject a therapeutically effective amount of a compound as described herein or a pharmaceutical composition thereof.

In one aspect, the disclosure features a method for treating a subject who has developed resistance to a cancer treatment comprising a wild-type RET inhibitor, comprising administering to the subject a therapeutically effective amount of a compound as described herein or a pharmaceutical composition thereof. In some embodiments, the subject is suffering from papillary thyroid carcinoma or non-small cell lung cancer.

In one aspect, the disclosure features a method for treating a subject who has developed resistance to a treatment for a condition mediated by aberrant RET activity, comprising administering to the subject a therapeutically effective amount of a compound as described herein or a pharmaceutical composition thereof.

RET fusions have been implicated in several types of cancers. Generally, these RET fusions have a RET kinase domain that is the same as in wild-type RET; therefore, as used herein, any RET protein with the same kinase domain as wild-type RET will be referred to as "wild-type RET" unless noted otherwise. Mutations can occur at least in the RET extracellular and kinase domains. Mutations can occur in the RET kinase domain, leading to resistant mutants of RET.

The activity of exemplary compounds that are approved or in development for RET-related conditions is shown below. As shown, the compounds are active against the wild-type RET, but are much less active against the mutated forms ("wild-type RET inhibitors").

TABLE 2

| Compound | RET wt Biochemical $IC_{50}$ (nM) | RET V804L Biochemical $IC_{50}$ (nM) | RET V804M Biochemical $IC_{50}$ (nM) |
| --- | --- | --- | --- |
| Cabozantinib | 46 | 219 | 585 |
| Vandetanib | 1.2 | 902 | 607 |
| Sorafenib | 7.9 | 95.2 | 32.4 |
| Regorafenib | 5.1 | 29.8 | 46.7 |

The disclosure provides compounds that inhibit both wild-type RET and resistant mutants of RET. In addition, the compounds of the disclosure can be selective for wild-type RET, over other kinases, thus leading to reduced toxicities associated with inhibiting other kinases. In one aspect, compounds of the disclosure are selective for RET over KDR. In one aspect, compounds of the disclosure do not cause adverse effects such as hypertension, arterial thrombosis, and hemorrhage.

In addition, the disclosure provides inhibitors of mutant RET. Mutations can be predicted using structural biology and computational analyses, as well as by examining codon sequences in which a sequence change gives rise to a codon for a different amino acid. Using such methods, resistant mutants for RET are predicted to have point mutations at the 804 gatekeeper residue in the RET protein and/or at residues at or near the gatekeeper residue. In some embodiments, the mutation may be at one or more of the 804, 806, 810, 865, 870, 891, and 918 residues. Specific examples of RET resistant mutants include: V804L, V804M, V804E, Y806C, Y806S, Y806H, Y806N, G810R, G810S, L865V, L870F, S891A and M918T mutants.

Mutations occurring from administration of a particular inhibitor (e.g., a known RET wild-type inhibitor) can be determined experimentally by exposing cells to a mutation-promoting agent, such as ENU. The cells are washed, then plated with increasing concentrations (2-100× proliferation $IC_{50}$) of the compound of choice. The wells with cellular outgrowth are then collected after 3-4 weeks. The RET kinase domain is then sequenced to identify resistance mutations (i.e., altered forms of the RET protein that retain enzymatic activity). Resistance can be confirmed by exposing these cells with the compound of choice. Resistant mutants that have been identified experimentally include the V804L, V804E, V804M, and Y806H mutants. In some embodiments, the mutation is a substitution of cysteine (C609, C611, C618, C620, C630, and C634) in the RET extracellular domain for any other amino acid. In some embodiments, the RET cysteine variants (affecting C609, C611, C618, and C620) are the "Janus mutations." In some embodiments, RET mutations include: RET C634W, RET M918T, V804L, V804E, V804M, V804L, Y806C, Y806S, Y806N, Y806H, G810R, G810S, L865V, L870F, and S891A mutants.

Because of their activity against wild-type RET and mutant RET, the compounds described herein can be used to treat a patient with a condition associated with aberrant RET activity. The compounds described herein can provide treatments for irritable bowel syndrome (IBS), proliferative diseases, and any other conditions related to aberrant RET activity. The compounds can be used to treat irritable bowel syndrome. The compounds can be used to treat various cancers. In some embodiments, the cancer is selected from papillary thyroid carcinoma (PTC), medullary thyroid cancer (MTC), pheochromocytoma (PC), pancreatic ductal adenocarcinoma, multiple endocrine neoplasia (MEN2A and MEN2B), metastatic breast cancer, testicular cancer, small cell lung cancer, non-small cell lung cancer, chronic myelomonocytic leukemia, colorectal cancer, ovarian cancer, and cancers of the salivary gland. In some embodiments, the cancer is a solid tumor. In some embodiments, the condition associated with aberrant RET activity is a thyroid cancer (e.g., papillary thyroid carcinoma, thyroid adenocarcinoma, or MTC, e.g., familial MTC), lung cancer (e.g., lung adenocarcinoma, small-cell lung carcinoma, or non-small cell lung carcinoma), breast cancer (e.g., estrogen receptor-positive tumors and endocrine-resistant tumors e.g., resistant to oestrogen modulators such as tamoxifen, agents that block oestrogen biosynthesis such as aromatase inhibitors, and oestrogen receptor antagonists such as fulvestrant), pancreatic cancer (e.g., carcinoma of the pancreas or pancreatic ductal carcinoma), haematopoietic cancer, e.g., a leukemia (e.g., chronic myelomonocytic leukemia or acute myeloid leukemia), colon cancer (e.g., colon carcinoma), melanoma (e.g., cutaneous or desmoplastic malignant melanomas), prostate cancer, renal cancer (e.g., renal cell carcinoma), and head and neck tumors, neuroblastoma, ganglioneuroma (e.g., ganglioneuroma of the mouth or gut), colon cancer (e.g., sporadic colon cancers), MEN2A (multiple endocrine neoplasia type 2A), or MEN2B (multiple endocrine neoplasia type 2B). In one aspect, the MEN2A is characterized by MTC and includes adrenal tumor pheochromocytoma. Substitutions of cysteines in RET are found in subjects with MEN2A and also frequent in FMTC. RET extracellular domain exon 8 mutations, such as G533C) or the RET intracellular domain (residues E768, L790, Y791, V804, and S891) are associated with FMTC or MEN2A. Substitutions in the RET kinase domain, Met918 to Thr (M918T) or A883F are found in subjects with MEN2B. RET M918T and RET A883F are also found in sporadic MTC.

The compounds can also be used to treat a patient who has developed resistance to a wild-type RET inhibitor, or a patient with a particular RET mutant. The method includes the step of administering a compound or composition of the disclosure that is active against one or more RET resistant mutants. In certain embodiments, the RET resistant mutant is selected from V804L, V804M, V804E, Y806C, Y806S, Y806N, Y806H, G810R, G810S, L865V, L870F, S891A and M918T. By "active" is meant that a compound has an $IC_{50}$ of less than 1 μM, 500 nM, 250 nM, 100 nM, 75 nM, 50 nM, 25 nM, 10 nM, or 5 nM when measured in a biochemical assay, against at least one resistant mutant.

In some embodiments, the cancer is a solid tumor. In some embodiments, the condition associated with aberrant RET activity is a thyroid cancer (e.g., papillary thyroid carcinoma, thyroid adenocarcinoma, or MTC, e.g., familial MTC), lung cancer (e.g., lung adenocarcinoma, small-cell lung carcinoma, or non-small cell lung carcinoma), breast cancer (e.g., estrogen receptor-positive tumors and endocrine-resistant tumors e.g., resistant to oestrogen modulators such as tamoxifen, agents that block oestrogen biosynthesis such as aromatase inhibitors, and oestrogen receptor antagonists such as fulvestrant), pancreatic cancer (e.g., carcinoma of the pancreas or pancreatic ductal carcinoma), haematopoietic cancer, e.g., a leukemia (e.g., chronic myelomonocytic leukemia or acute myeloid leukemia), colon cancer (e.g., colon carcinoma), melanoma (e.g., cutaneous or desmoplastic malignant melanomas), prostate cancer, renal cancer (e.g., renal cell carcinoma), and head and neck tumors, neuroblastoma, ganglioneuroma (e.g., ganglioneuroma of the mouth or gut), colon cancer (e.g., sporadic colon cancers), MEN2A (multiple endocrine neoplasia type 2A), or MEN2B (multiple endocrine neoplasia type 2B). In one aspect, the MEN2A is characterized by MTC and includes adrenal tumor pheochromocytoma. Substitutions of cysteines in RET are found in subjects with MEN2A and also frequent in FMTC. RET extracellular domain exon 8 mutations, such as G533C) or the RET intracellular domain (residues E768, L790, Y791, V804, and S891) are associated with FMTC or MEN2A. Substitutions in the RET kinase domain, Met918 to Thr (M918T) or A883F are found in subjects with MEN2B. RET M918T and RET A883F are also found in sporadic MTC.

The compounds may also be used to treat a subject having a RET-altered cell, cancer, gene, or gene product. The RET alteration may be, e.g., a point mutation, insertion, deletion, amplification, or fusion, or a combination thereof.

The compounds may also be used to treat a subject having a RET-altered cell, cancer, gene, or gene product comprising a RET alteration described in Table 3 or Table 4 herein. In some embodiments, the subject has a fusion between RET and a RET fusion partner listed in Table 3, e.g., comprises a fusion protein that comprises RET or a fragment thereof and a protein of Table 3 or fragment thereof. In some embodiments, the fusion partner is N-terminal or C-terminal of RET. In some embodiments, the subject has an alteration at a position in RET that is described in Table 4. In some embodiments, a subset of the subject's cells, e.g., a subset of the subject's tumor cells, comprise the RET alteration. In some embodiments, a subset of the subject's cells, e.g., a subset of the subject's tumor cells, are RET-altered. In some embodiments, the subject has a cancer listed in Table 3, e.g., the subject has both a RET mutation and a cancer listed in Table 3.

TABLE 3

RET fusions

| RET fusion partner | Exemplary cancers in which the fusion is found |
|---|---|
| BCR | Chronic Myelomonocytic Leukemia (CMML) |
| CLIP 1 | Adenocarcinoma |
| KIF5B | NSCLC, Ovarian Cancer, Spitzoid Neoplasm; Lung Adenocarcinoma, Adenosquamous Carcinomas |
| CCDC6 | NSCLC, Colon Cancer, Papillary Thyroid Cancer; Adenocarcinoma; Lung Adenocarcinoma; Metastatic Colorectal Cancer; Adenosquamous Carcinoma, Metastatic papillary thyroid cancer |
| PTC1ex9 | Metastatic papillary thyroid cancer |
| NCOA4 | Papillary Thyroid Cancer, NSCLC, Colon Cancer, Salivary Gland Cancer, Metastatic Colorectal Cancer; Lung Adenocarcinoma, Adenosquamous Carcinomas; Diffuse Sclerosing Variant of Papillary Thyroid Cancer |
| TRIM33 | NSCLC, Papillary Thyroid Cancer |
| ERC1 | Papillary Thyroid Cancer, Breast Cancer |
| FGFR1OP | CMML, Primary Myelofibrosis with secondary Acute Myeloid Leukemia |
| MBD1 | Papillary Thyroid Cancer |
| RAB6IP2 | Papillary Thyroid Cancer |
| PRKAR1A | Papillary Thyroid Cancer |
| TRIM24 | Papillary Thyroid Cancer |
| KTN1 | Papillary Thyroid Cancer |
| GOLGA5 | Papillary Thyroid Cancer, Spitzoid Neoplasms |
| HOOK3 | Papillary Thyroid Cancer |
| KIAA1468 | Papillary Thyroid Cancer, Lung Adenocarcinoma |
| TRIM27 | Papillary Thyroid Cancer |
| AKAP13 | Papillary Thyroid Cancer |
| FKBP15 | Papillary Thyroid Cancer |
| SPECC1L | Papillary Thyroid Cancer, Thyroid Gland Carcinoma |

TABLE 3-continued

RET fusions

| RET fusion partner | Exemplary cancers in which the fusion is found |
|---|---|
| TBL1XR1 | Papillary Thyroid Cancer, Thyroid Gland Carcinoma |
| CEP55 | Diffuse Gastric Cancer |
| CUX1 | Lung Adenocarcinoma |
| ACBD5 | Papillary Thyroid Carcinoma |
| MYH13 | Medullary Thyroid Carcinoma |
| PIBF1 | Bronchiolus Lung Cell Carcinoma |
| KIAA1217 | Papillary Thyroid Cancer, Lung Adenocarcinoma, NSCLC |
| MPRIP | NSCLC |

TABLE 4

RET mutations

| | |
|---|---|
| Amino acid position 2 | Amino acid position 665 (e.g., H665Q) |
| Amino acid position 3 | Amino acid position 666 (e.g., K666E, K666M, or K666N) |
| Amino acid position 4 | Amino acid position 686 (e.g., S686N) |
| Amino acid position 5 | Amino acid position 691 (e.g., G691S) |
| Amino acid position 6 | Amino acid position 694 (e.g., R694Q) |
| Amino acid position 7 | Amino acid position 700 (e.g., M700L) |
| Amino acid position 8 | Amino acid position 706 (e.g., V706M or V706A) |
| Amino acid position 11 | Amino acid position 713 splice variant (e.g., E713K) |
| Amino acid position 12 | Amino acid position 736 (e.g., G736R) |
| Amino acid position 13 | Amino acid position 748 (e.g., G748C) |
| Amino acid position 20 | Amino acid position 750 (e.g., A750P) |
| Amino acid position 32 (e.g., S32L) | Amino acid position 765 (e.g., S765P) |
| Amino acid position 34 (e.g., D34S) | Amino acid position 766 (e.g., P766S or P766M6) |
| Amino acid position 40 (e.g., L40P) | Amino acid position 768 (e.g., E768Q or E768D) |
| Amino acid position 64 (e.g., P64L) | Amino acid position 769 (e.g., L769L) |
| Amino acid position 67 (e.g., R67H) | Amino acid position 770 (e.g., R770Q) |
| Amino acid position 114 (e.g., R114H) | Amino acid position 771 (e.g., D771N) |
| Amino acid position 136 (e.g., glutamic acid to stop codon) | Amino acid position 777 (e.g., N777S) |
| Amino acid position 145 (e.g., V145G) | Amino acid position 778 (e.g., V778I) |
| Amino acid position 180 (e.g., arginine to stop codon) | Amino acid position 781 (e.g., Q781R) |
| Amino acid position 200 | Amino acid position 790 (e.g., L790F) |
| Amino acid position 292 (e.g., V292M) | Amino acid position 791 (e.g., Y791F or Y791N) |
| Amino acid position 294 | Amino acid position 802 |
| Amino acid position 321 (e.g., G321R) | Amino acid position 804 (e.g., V804L, V804M, V804M*, or V804E) |
| Amino acid position 330 (e.g., R330Q) | Amino acid position 805 (e.g., E805K) |
| Amino acid position 338 (e.g., T338I) | Amino acid position 806 (e.g., E806C, Y806E, Y806F, Y806S, Y806G, or Y806C) |
| Amino acid position 360 (e.g., R360W) | Amino acid position 818 (e.g., E818K) |
| Amino acid position 373 (e.g., alanine to frameshift) | Amino acid position 819 (e.g., S819I) |
| Amino acid position 393 (e.g., F393L) | Amino acid position 823 (e.g., G823E) |
| Amino acid position 432 | Amino acid position 826 (e.g., Y826M) |
| Δ Amino acid residues 505-506 (6-Base Pair In-Frame Germline Deletion in Exon 7) | Amino acid position 833 (e.g., R833C) |
| Amino acid position 510 (e.g., A510V) | Amino acid position 841 (e.g., P841L or P841P) |
| Amino acid position 511 (e.g., E511K) | Amino acid position 843 (e.g., E843D) |
| Amino acid position 513 (e.g., A513D) | Amino acid position 844 (e.g., R844W, R844Q, or R844L) |
| Amino acid position 515 (e.g., C515S, C515W) | Amino acid position 848 (e.g., M848T) |
| Amino acid position 525 (e.g., R525W) | Amino acid position 852 (e.g., I852M) |
| Amino acid position 531 (e.g., C531R, or 9 base pair duplication) | Amino acid position 866 (e.g., A866W) |
| Amino acid position 532 (e.g., duplication) | Amino acid position 873 (e.g., R873W) |
| Amino acid position 533 (e.g., G533C or G533S) | Amino acid position 876 (e.g., A876V) |
| Amino acid position 550 (e.g., G550E) | Amino acid position 881 (e.g., L881V) |
| Amino acid position 591 (e.g., V591I) | Amino acid position 882 |
| Amino acid position 593 (e.g., G593E) | Amino acid position 883 (e.g., A883F, A883S, A883T, or A883T*) |
| Amino acid position 600 (e.g., R600Q) | Amino acid position 884 (e.g., E884K) |

TABLE 4-continued

| RET mutations | |
|---|---|
| Amino acid position 602 (e.g., I602V) | Amino acid position 886 (e.g., R886W) |
| Amino acid position 603 (e.g., K603Q or K603E2) | Amino acid position 891 (e.g., S891A) |
| Amino acid position 606 (e.g., Y606C) | Amino acid position 897 (e.g., R897Q) |
| Amino acid position 609 (e.g., C609Y, C609S, C609G, C609R, C609F, or C609W) | Amino acid position 898 (e.g., D898V) |
| Amino acid position 611 (e.g., C611R, C611S, C611G, C611Y, C611F, or C611W) | Amino acid position 901 (e.g., E901K) |
| Amino acid position 618 (e.g., C618S, C618Y, C618R, C618Y, C618G, C618F, C618W) | Amino acid position 904 (e.g., S904F or S904C2) |
| Amino acid position 619 (e.g., F619F) | Amino acid position 907 (e.g., K907E or K907M) |
| Amino acid position 620 (e.g., C620S, C620W, C620R, C620G, C620L, C620Y, C620F) | Amino acid position 908 (e.g., R908K) |
| Amino acid position 623 (e.g., E623K) | Amino acid position 911 (e.g., G911D) |
| Amino acid position 624 (e.g., D624N) | Amino acid position 912 (e.g., R912P, R912Q) |
| Amino acid position 630 (e.g., C630A, C630R, C630S, C630Y, or C630F) | Amino acid position 918 (e.g., M918T, M918V, or M918L6) |
| Amino acid position 631 (e.g., D631N, D631Y, D631A, D631G, D631V, or D631E) | Amino acid position 919 (e.g., A919V) |
| Amino acid position 632 (e.g., E632K or E632G5) | Amino acid position 921 (e.g., E921K) |
| Δ Amino acid residues 632-633 (6-Base Pair In-Frame Germline Deletion in Exon 11) | Amino acid position 922 (e.g., S922P or S922Y) |
| Amino acid position 633 (e.g., 9 base pair duplication) | Amino acid position 930 (e.g., T930M) |
| Amino acid position 634 (e.g., C634W, C634Y, C634S, C634R, C634F, C634G, C634L, C634A, or C634T, or an insertion ELCR2, or a 12 base pair duplication) | Amino acid position 961 (e.g., F961L) |
| Amino acid position 635 (e.g., R635G) | Amino acid position 972 (e.g., R972G) |
| Amino acid position 636 (e.g., T636P or T636M4) | Amino acid position 982 (e.g., R982C) |
| Amino acid position 640 (e.g., A640G) | Amino acid position 1009 (e.g., M1009V) |
| Amino acid position 641 (e.g., A641S or A641T8) | Amino acid position 1017 (e.g., D1017N) |
| Amino acid position 648 (e.g., V6481) | Amino acid position 1041 (e.g., V1041G) |
| Amino acid position 649 (e.g., S649L) | Amino acid position 1064 (e.g., M1064T) |
| Amino acid position 664 (e.g., A664D) | RET + 3 |

RET has two primary protein and mRNA isoforms, named RET51 and RET9. In some embodiments, RET has a sequence of isoform RET51 (SEQ ID NO: 1). The kinase domain corresponds to amino acids 724-1016 of SEQ ID NO: 1.

In some embodiments, RET has a sequence of isoform RET9 (SEQ ID NO: 2).

In some embodiments, RET51 is encoded by a nucleic acid having the sequence of SEQ ID NO: 3.

In some embodiments, RET9 is encoded by a nucleic acid having the sequence of SEQ ID NO: 4.

The compounds and compositions described herein can be administered alone or in combination with other compounds, including other RET-modulating compounds, or other therapeutic agents. In some embodiments, the compound or composition of the disclosure may be administered in combination with one or more compounds selected from cabozantinib (COMETRIQ), vandetanib (CALPRESA), sorafenib (NEXAVAR), sunitinib (SUTENT), regorafenib (STAVARGA), ponatinib (ICLUSIG), bevacizumab (AVASTIN), crizotinib (XALKORI), or gefitinib (IRESSA). The compound or composition of the disclosure may be administered simultaneously or sequentially with the other therapeutic agent by the same or different routes of administration. The compound of the disclosure may be included in a single formulation with the other therapeutic agent or in separate formulations.

Synthesis

Compounds of the disclosure, including salts and N-oxides thereof, can be prepared using known organic synthesis techniques and can be synthesized according to any of numerous possible synthetic routes, such as those in the Schemes below. The reactions for preparing compounds of the disclosure can be carried out in suitable solvents which can be readily selected by one of skill in the art of organic synthesis. Suitable solvents can be substantially non-reactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the disclosure can involve the protection and deprotection of various chemical groups. The need for protection and deprotection, and the selection of appropriate protecting groups, can be readily determined by one skilled in the art. The chemistry of protecting groups can be found, for example, in Wuts and Greene, Protective Groups in Organic Synthesis, 4th ed., John Wiley & Sons: New Jersey, (2006), which is incorporated herein by reference in its entirety.

Reactions can be monitored according to any suitable method known in the art. For example, product formation can be monitored by spectroscopic means, such as nuclear magnetic resonance (NMR) spectroscopy (e.g., $^1$H or $^{13}$C), infrared (IR) spectroscopy, spectrophotometry (e.g., UV-visible), mass spectrometry (MS), or by chromatographic methods such as high performance liquid chromatography (HPLC) or thin layer chromatography (TLC). Analytical instruments and methods for compound characterization:

LC-MS:

Unless otherwise indicated, all liquid chromatography-mass spectrometry (LC-MS) data (sample analyzed for purity and identity) were obtained with an Agilent model-1260 LC system using an Agilent model 6120 mass spectrometer utilizing ES-API ionization fitted with an Agilent Poroshel 120 (EC-C18, 2.7 um particle size, 3.0×50 mm dimensions) reverse-phase column at 22.4 degrees Celsius. The mobile phase consisted of a mixture of solvent 0.1% formic acid in water and 0.1% formic acid in acetonitrile. A constant gradient from 95% aqueous/5% organic to 5% aqueous/95% organic mobile phase over the course of 4 minutes was utilized. The flow rate was constant at 1 mL/min.

Prep LC-MS:

Preparative HPLC was performed on a Shimadzu Discovery VP® Preparative system fitted with a Luna 5u C18(2) 100A, AXIA packed, 250×21.2 mm reverse-phase column at 22.4 degrees Celsius. The mobile phase consisted of a mixture of solvent 0.1% formic acid in water and 0.1% formic acid in acetonitrile. A constant gradient from 95% aqueous/5% organic to 5% aqueous/95% organic mobile phase over the course of 25 minutes was utilized. The flow rate was constant at 20 mL/min. Reactions carried out in a microwave were done so in a Biotage Initiator microwave unit.

Silica Gel Chromatography:

Silica gel chromatography was performed on either a Teledyne Isco CombiFlash® Rf unit or a Biotage® Isolera Four unit.

Proton NMR:

Unless otherwise indicated, all $^1$H NMR spectra were obtained with a Varian 400 MHz Unity Inova 400 MHz NMR instrument (acquisition time=3.5 seconds with a 1 second delay; 16 to 64 scans). Where characterized, all protons were reported in DMSO-d6 solvent as parts-per million (ppm) with respect to residual DMSO (2.50 ppm).

The below Synthetic Protocols are meant to provide general guidance in connection with preparing the compounds of the disclosure. One skilled in the art would understand that the preparations shown in the Synthetic Protocols can be modified or optimized using general knowledge of organic chemistry to prepare various compounds of the disclosure. In each of the Synthetic Protocols below, "R" represents a hydrolyzable moiety, and "PG" represents a protecting group.

Synthetic Protocol 1:

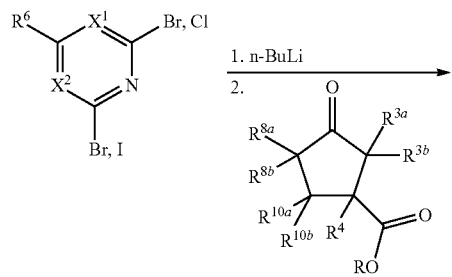

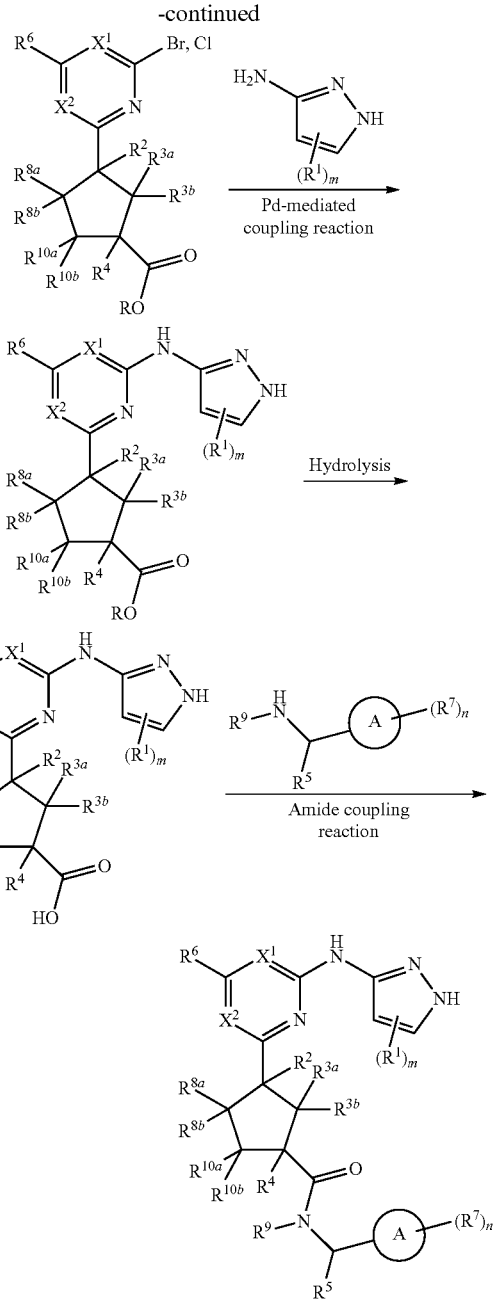

An aryl dihalide can be treated with an organolithium or organomagnesium halide reagent, such as n-BuLi or i-PrMgCl, and the arylmetal reagent can then undergo addition to an ester substituted cyclopentanone (either commercially available or prepared as described in "Synthesis of Ketone Intermediates"). The remaining halide can then undergo a coupling reaction with an arylamine under SnAr conditions or metal-catalyzed coupling conditions to give a tricyclic ester intermediate. The ester can then be hydrolyzed under basic conditions to give an acid, which can then undergo an amide coupling reaction with an amine (either commercially available or prepared as described in "Synthesis of Amine Intermediates"). The amides are examples of RET inhibitors described herein.

Synthetic Protocol 2:

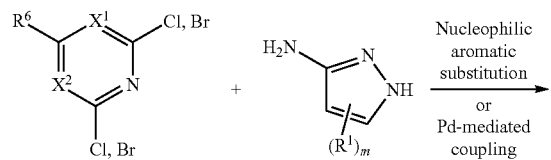

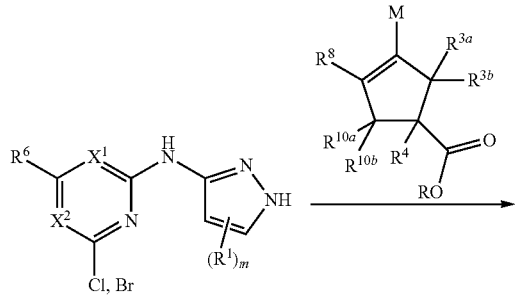

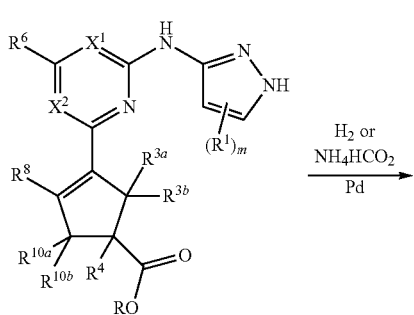

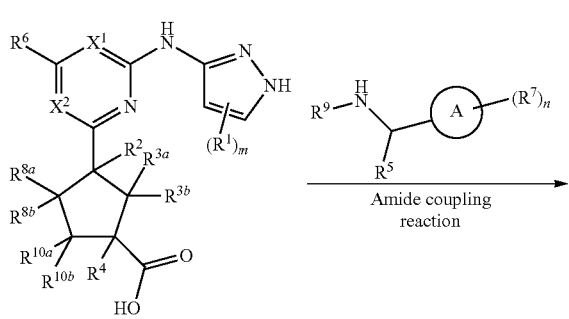

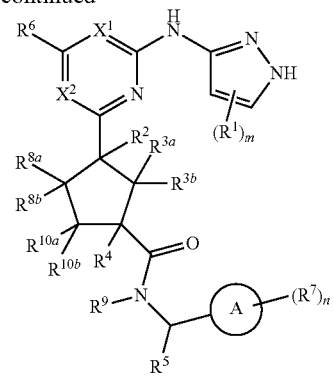

The heteroaryl dihalide can be coupled to an amino pyrazole under nucleophilic aromatic substitution reaction conditions using a base such as diisopropylethylamine (DIPEA) or triethylamine (TEA) in a polar solvent to provide the bicyclic ring system. The bicyclic heteroaryl halide can then be coupled to a to a boron, tin or zinc alkenyl or alkyl reagent via a Palladium-mediated coupling reaction, e.g., Suzuki, Stille, Negishi coupling, to provide the tricyclic ring system. For example, in Synthetic Protocol 2, the bicyclic heteroaryl halide of the can be coupled to a variety of ester substituted cyclopentenyl boronic esters (commercially available or prepared as described herein) under Suzuki coupling reaction conditions (X=halo, e.g., chloro; and M=B(OR)$_2$) to provide the tricyclic carboxylic ester intermediate. The carboxylic ester can then be hydrolyzed under acidic or basic conditions to provide a carboxylic acid intermediate. The carboxylic acid intermediate can then be coupled to a variety of amines, such as those described below under the heading "Synthesis of Amine Intermediates," to provide the amide final product.

Synthetic Protocol 3:

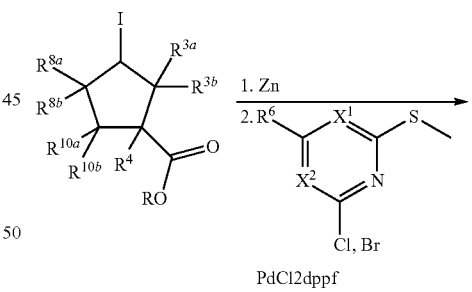

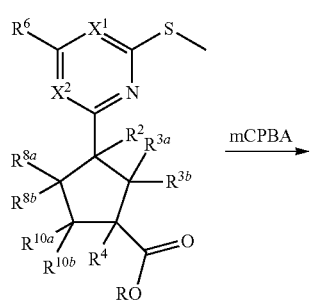

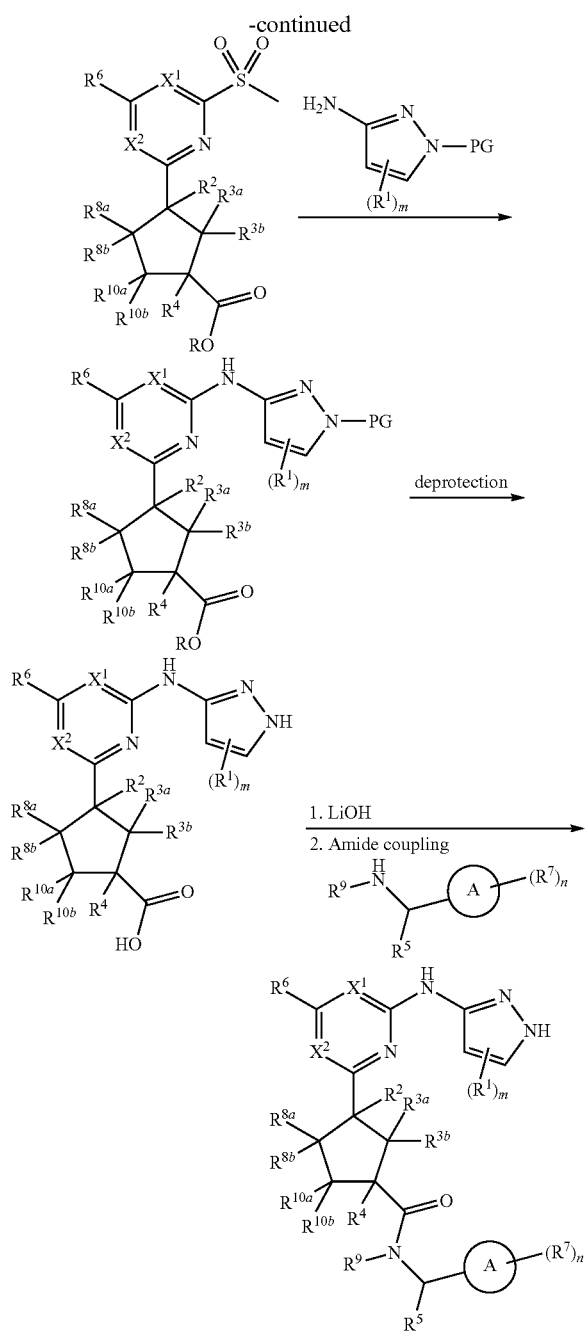

A substituted cyclopentyl iodide (either commercially available or prepared as described in "Synthesis of Iodide Intermediates") is treated with activated zinc. The zinc could be activated by a variety methods, including but not limited to the method of Reike or treatment with TMS-Cl and 1,2-dibromoethane. The cycloalkyl zinc reagent can then be coupled to a heteroaryl halide with palladium catalysis under Negishi coupling conditions. The thiomethyl group of the resulting product can then be converted to a sulfone. The sulfone can then be displaced by a protected amino pyrazole, using a protecting group such as THP to protect the ring nitrogen of the pyrazole. The protecting group can then be removed under standard deprotection conditions, for example acidic hydrolysis to remove a THP. The tricyclic ester intermediate can be hydrolyzed under acidic or basic conditions to give a tricyclic carboxylic acid intermediate. Finally the carboxylic acid intermediate can then be coupled to a variety of amines, such as those described below under the heading "Synthesis of Amine Intermediates," to provide the amide final product.

EXAMPLES

The following examples are intended to be illustrative, and are not meant in any way to be limiting.

Example 1. Synthesis of Compounds 121 and 122

Step 1: Synthesis of methyl (1R,3S and 1S,3R)-3-(6-bromo-4-methylpyridin-2-yl)-3-hydroxycyclopentane-1-carboxylate and methyl (1R,3R and 1S,3S)-3-(6-bromo-4-methylpyridin-2-yl)-3-hydroxycyclopentane-1-carboxylate

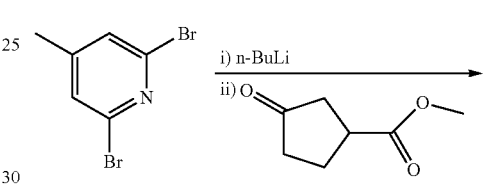

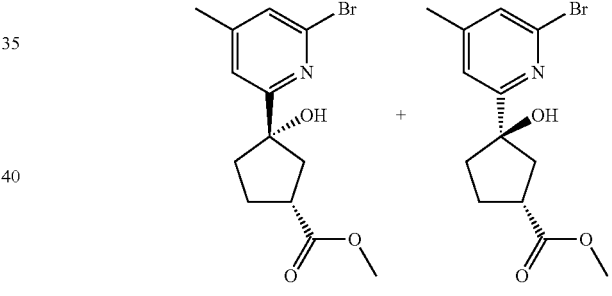

A solution of n-BuLi (4.4 mL, 2.5 M in n-hexane, 11 mmol) was slowly added to a solution of 2,6-dibromo-4-methylpyridine (2.75 g, 10.9 mmol) in DCM (83 mL) at −78° C. under $N_2$. After stirring for 1.5 h at −78° C., methyl 3-oxocyclopentanecarboxylate (1.54 g, 11.0 mmol) was added. The cooling bath was removed and the reaction mixture was stirred for 2 h, and then was quenched by addition of saturated aqueous NH4Cl solution. The reaction mixture was extracted with ethyl acetate, and the organic layers were dried over sodium sulfate, filtered, and concentrated. The residue was purified by flash column chromatography on silica gel (isocratic elution, 8% ethyl acetate-petroleum ether) to give two product diastereomers. Peak 1 (550 mg, yellow solid) was determined to be the 1R,3S and 1S,3R isomers, and peak 2 (350 mg, yellow oil) was determined to be the 1R,3R and 1S,3S isomers. MS (ES+) $C_{13}H_{16}BrNO_3$ requires: 313. found: 314 [M+H]+.

Step 2: Synthesis of methyl (1R,3S and 1S,3R)-3-hydroxy-3-(4-methyl-6-((5-methyl-1H-pyrazol-3-yl)amino)pyridin-2-yl)cyclopentane-1-carboxylate

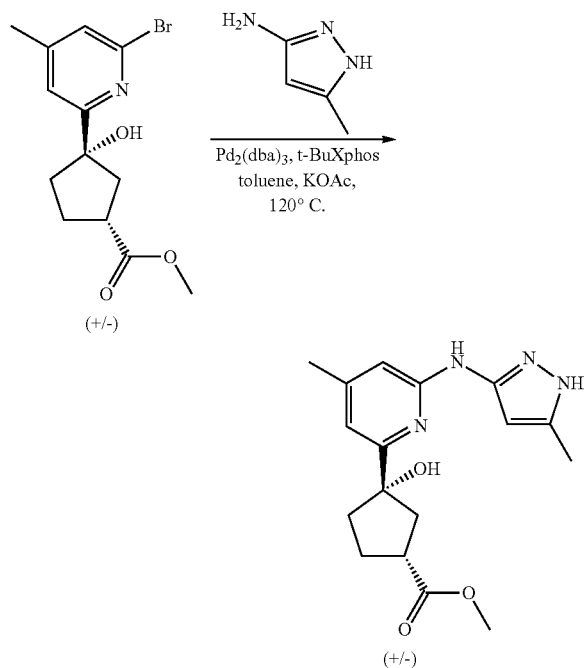

A mixture of methyl (1R,3S and 1S,3R)-3-(6-bromo-4-methylpyridin-2-yl)-3-hydroxycyclopentane-1-carboxylate (1.5 g, 4.77 mmol), 5-methyl-1H-pyrazol-3-amine (926 mg, 9.54 mmol), Pd$_2$(dba)$_3$ (873 mg, 0.954 mmol), t-BuXphos (404 mg, 0.954 mmol) and KOAc (1.4 g, 14.3 mmol) in toluene (30 mL) was degassed with nitrogen and refluxed at 120° C. for 16 h. The reaction mixture was cooled to ambient temperature and concentrated to give a residue, which was purified by flash column chromatography on silica gel (gradient elution, 30 to 100% ethyl acetate-petroleum ether) to afford the title compound (1.0 g, 64%) as a white solid. MS (ES+) C$_{17}$H$_{22}$N$_4$O$_3$ requires: 330. found: 331 [M+H]$^+$.

Step 3: Synthesis of (1R,3S and 1S,3R)-3-hydroxy-3-(4-methyl-6-((5-methyl-1H-pyrazol-3-yl)amino)pyridin-2-yl)cyclopentane-1-carboxylic acid

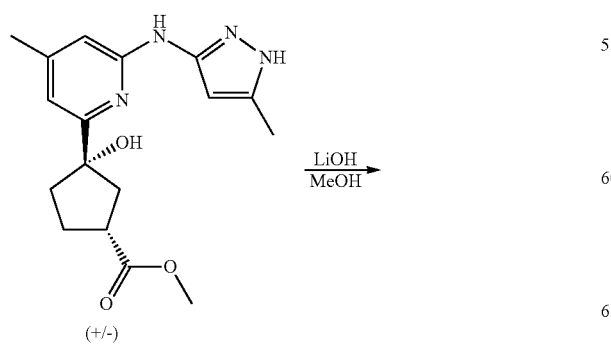

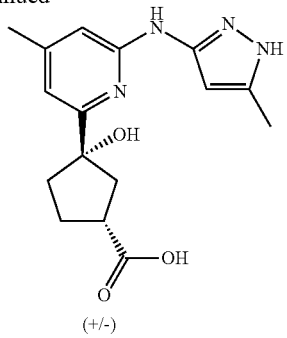

To a solution of methyl (1R,3S and 1S,3R)-3-hydroxy-3-(4-methyl-6-((5-methyl-1H-pyrazol-3-yl)amino)pyridin-2-yl)cyclopentane-1-carboxylate (400 mg, 1.21 mmol) in THF/H$_2$O (5 mL) was added Leo (28.9 mg, 1.21 mmol). The mixture was stirred at ambient temperature for 16 h. The reaction mixture was concentrated and purified directly by preparative rp-HPLC (gradient elution 10 to 100% ACN in water with 0.1% TFA) to give the title compound (70 mg, 18%). MS (ES+) C$_{16}$H$_{20}$N$_4$O$_3$ requires: 316. found: 317 [M+H]$^+$.

Step 4: Synthesis of (1R,3S)—N—((S)-1-(6-(4-fluoro-1H-pyrazol-1-yl)pyridin-3-yl)ethyl)-3-hydroxy-3-(4-methyl-6-((5-methyl-1H-pyrazol-3-yl)amino)pyridin-2-yl)cyclopentane-1-carboxamide and (1S,3R)—N—((S)-1-(6-(4-fluoro-1H-pyrazol-1-yl)pyridin-3-yl)ethyl)-3-hydroxy-3-(4-methyl-6-((5-methyl-1H-pyrazol-3-yl)amino)pyridin-2-yl)cyclopentane-1-carboxamide

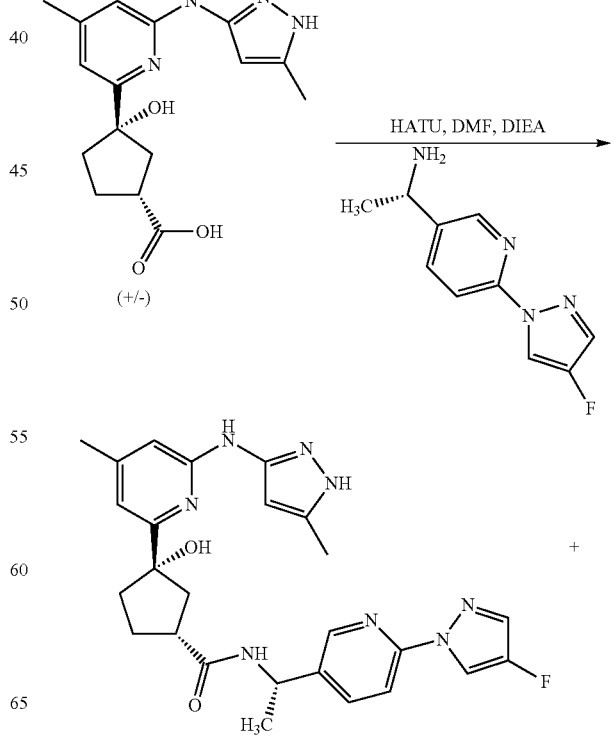

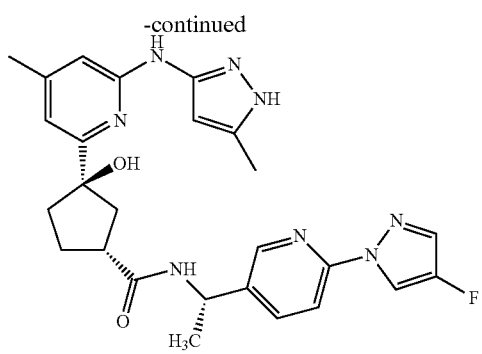

To a mixture of (1R,3 S and 1 S,3R)-3-hydroxy-3-(4-methyl-6-((5-methyl-1H-pyrazol-3-yl)amino)pyridin-2-yl)cyclopentane-1-carboxylic acid (28 mg, 88.5 μmol) in DMF (1 mL) was added (S)-1-(6-(4-fluoro-1H-pyrazol-1-yl)pyridin-3-yl)ethanamine (18.2 mg, 88.5 μmol), DIEA (22.8 mg, 177 μmol) and HATU (50.1 mg, 132 μmol). The mixture was stirred at ambient temperature for 4 h. The mixture was concentrated and purified by preparative reverse phase (rp)-HPLC (gradient elution 10 to 100% ACN in water with 0.1% TFA) to give the title compounds as a mixture of isomers (7.5 mg, 16.8%). The isomeric mixture (86 mg) was dissolved in methanol/dichloromethane/2-propanol (12 mL, 4:1:1) and purified by SFC (ChiralPak AD-H 21×250 mm, 45% 2-propanol containing 0.25% DEA in CO2, 2.5 mL injections, 70 mL/min). Peak 1 was concentrated to give (1R,3S)—N—((S)-1-(6-(4-fluoro-1H-pyrazol-1-yl)pyridin-3-yl)ethyl)-3-hydroxy-3-(4-methyl-6-((5-methyl-1H-pyrazol-3-yl)amino)pyridin-2-yl)cyclopentane-1-carboxamide (Compound 121; 36.6 mg) as a white solid. Peak 2 was concentrated to give (1S,3R)—N—((S)-1-(6-(4-fluoro-1H-pyrazol-1-yl)pyridin-3-yl)ethyl)-3-hydroxy-3-(4-methyl-6-((5-methyl-1H-pyrazol-3-yl)amino)pyridin-2-yl)cyclopentane-1-carboxamide (Compound 122; 36.0 mg) as a white solid. The absolute stereochemistry of the cyclopentyl ring was assigned arbitrarily. Spectral data can be found in Table 5.

Example 2. Synthesis of Compounds 106, 107, 108, 109 and 110

Step 1: Synthesis of 2-chloro-6-methyl-N-(5-methyl-1H-pyrazol-3-yl)pyrimidin-4-amine

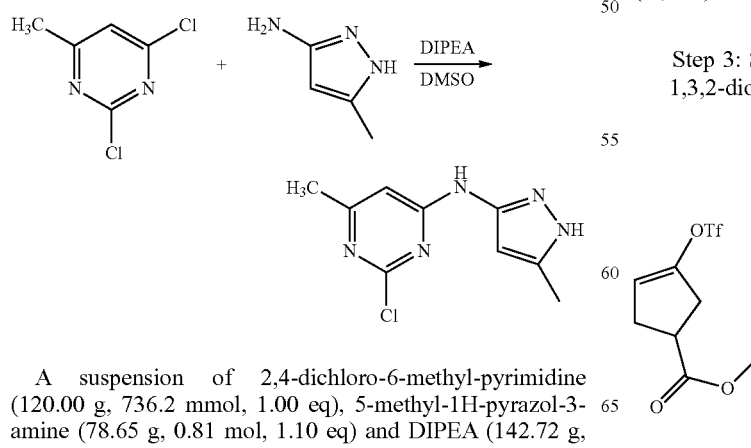

A suspension of 2,4-dichloro-6-methyl-pyrimidine (120.00 g, 736.2 mmol, 1.00 eq), 5-methyl-1H-pyrazol-3-amine (78.65 g, 0.81 mol, 1.10 eq) and DIPEA (142.72 g, 1.10 mol, 1.50 eq) in DMSO (400.00 mL) was heated at 60° C. for 16 hrs. TLC (PE/EA, 5:1, 1:1) showed the reaction was complete. The reaction mixture was cooled to 30° C. and poured into ice-water (800 mL). The resulting mixture was extracted with MTBE (800 mL×10). The combined organic layers were washed with water (400 mL×3), brine (400 mL×3) and dried over Na₂SO₄. After filtration, the filtrate was concentrated under reduced pressure and the residue was recrystallized from DCM (10 mL/g) to afford 2-chloro-6-methyl-N-(5-methyl-1H-pyrazol-3-yl)pyrimidin-4-amine (105.60 g, 472.14 mmol, 64%) as a yellow solid. The structure was confirmed by LC-MS and NMR.

Step 2: Synthesis of methyl 3-(((trifluoromethyl)sulfonyl)oxy)cyclopent-3-ene-1-carboxylate

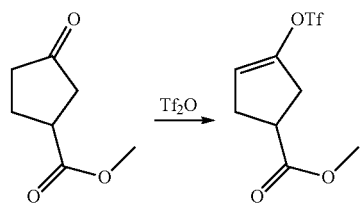

Methyl 3-oxocyclopentanecarboxylate (2.6 g, 18 mmol) and DIPEA (6.4 ml, 37 mmol) in Toluene (52 mL) were heated to 45° C. After reaching 45° C., triflic anhydride (5.9 ml, 35 mmol) was added dropwise over 2 min. The reaction mixture was stirred at 45° C. for 30 min, and then was partitioned between ethyl acetate and saturated aqueous sodium bicarbonate solution. The organic layer was washed with brine, dried over sodium sulfate, filtered, and concentrated. The residue was purified by flash-column chromatography on silica gel (gradient elution, 0 to 15% ethyl acetate-hexanes) to give methyl 3-(((trifluoromethyl)sulfonyl)oxy)cyclopent-3-ene-1-carboxylate (3.8 g, 76%) as a colorless oil. The product was a mixture (~1:1) of two olefin isomers. Spectral data for the mixture of isomers: ¹H NMR (400 MHz, Chloroform-d) δ 5.70 (p, J=1.9 Hz, 1H), 5.59 (h, J=2.1 Hz, 1H), 3.76-3.69 (m, 6H), 3.67-3.57 (m, 1H), 3.28 (dddd, J=9.9, 8.3, 6.7, 1.6 Hz, 1H), 2.98 (dtt, J=16.3, 3.8, 2.3 Hz, 1H), 2.88-2.78 (m, 1H), 2.83-2.54 (m, 4H), 2.41-2.24 (m, 2H).

Step 3: Synthesis of methyl 3-(4,4,5,5-tetramethyl-1,3,2-dioxaborolan-2-yl)cyclopent-3-ene-1-carboxylate

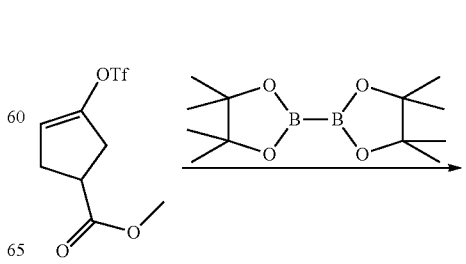

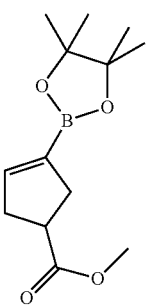

Nitrogen gas was bubbled through a mixture of methyl 3-(((trifluoromethyl)sulfonyl)oxy)cyclopent-3-ene-1-carboxylate (3.8 g, 14 mmol), bis(pinacolato)diboron (3.9 g, 15 mmol), and potassium acetate (1.77 g, 18.0 mmol) in dioxane (46 mL) for 20 min. $PdCl_2(dppf)$ (0.51 g, 0.69 mmol) was then added and the reaction mixture was sealed. The reaction mixture was heated to 90° C. for 16 h, and then was cooled to ambient temperature and partitioned between ethyl acetate and water. The organic layer was washed with brine, dried over sodium sulfate, filtered, and concentrated. The residue was purified by flash-column chromatography on silica gel (gradient elution, 0 to 70% ethyl acetate-hexanes) to give methyl 3-(4,4,5,5-tetramethyl-1,3,2-dioxaborolan-2-yl)cyclopent-3-ene-1-carboxylate (2.54 g) as a mixture of olefin isomers.

Step 4: Synthesis of methyl 3-(4-methyl-6-((5-methyl-1H-pyrazol-3-yl)amino)pyrimidin-2-yl)cyclopent-3-ene-1-carboxylate

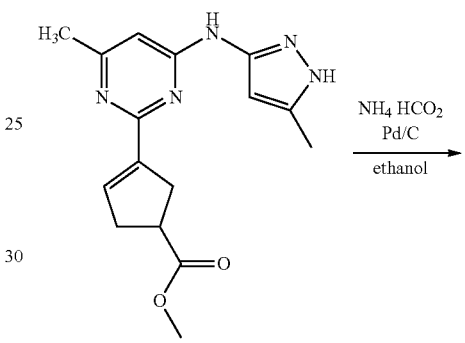

A mixture of 2-chloro-6-methyl-N-(5-methyl-1H-pyrazol-3-yl)pyrimidin-4-amine (0.500 g, 2.24 mmol), methyl 3-(4,4,5,5-tetramethyl-1,3,2-dioxaborolan-2-yl)cyclopent-3-ene-1-carboxylate (0.564 g, 2.24 mmol), and potassium carbonate (0.618 g, 4.47 mmol) in dioxane (8.4 ml) and water (2.8 ml) was sparged with nitrogen gas for 10 min, then $Pd(PPh_3)_4$ (0.258 g, 0.224 mmol) was added and the reaction vessel was sealed. The reaction mixture was heated in a microwave reactor at 125° C. for 70 min. The reaction mixture was then cooled to ambient temperature and partitioned between 5:1 ethyl acetate/IPA and water. The organic layer was dried over sodium sulfate. The dried solution was filtered, concentrated, and purified by silica gel chromatography (gradient elution, 0 to 10% methanol-DCM) to give methyl 3-(4-methyl-6-((5-methyl-1H-pyrazol-3-yl)amino)pyrimidin-2-yl)cyclopent-3-ene-1-carboxylate (0.50 g, 71%) as a yellow oil. MS (ES+) $C_{16}H_{19}N_5O_2$ requires: 313. found: 314 $[M+H]^+$.

Step 5: Synthesis of methyl 3-(4-methyl-6-((5-methyl-1H-pyrazol-3-yl)amino)pyrimidin-2-yl)cyclopentane-1-carboxylate

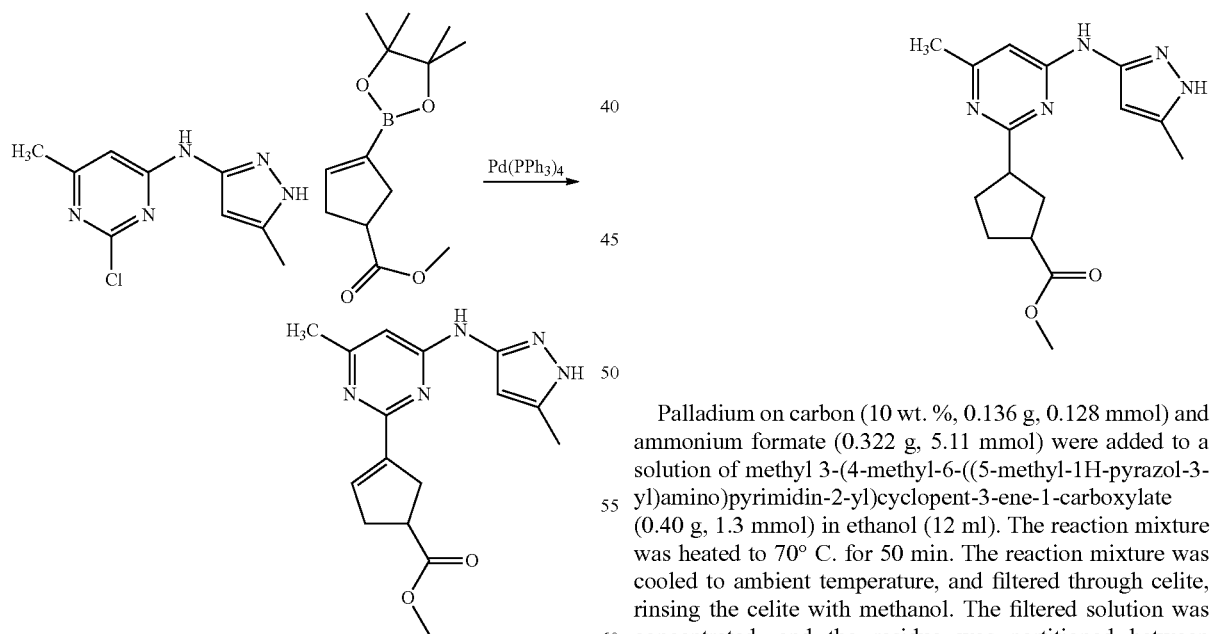

Palladium on carbon (10 wt. %, 0.136 g, 0.128 mmol) and ammonium formate (0.322 g, 5.11 mmol) were added to a solution of methyl 3-(4-methyl-6-((5-methyl-1H-pyrazol-3-yl)amino)pyrimidin-2-yl)cyclopent-3-ene-1-carboxylate (0.40 g, 1.3 mmol) in ethanol (12 ml). The reaction mixture was heated to 70° C. for 50 min. The reaction mixture was cooled to ambient temperature, and filtered through celite, rinsing the celite with methanol. The filtered solution was concentrated, and the residue was partitioned between DCM/IPA (5:1) and saturated aqueous sodium bicarbonate solution. The organic layer was dried over sodium sulfate, filtered, and concentrated to give methyl 3-(4-methyl-6-((5-methyl-1H-pyrazol-3-yl)amino)pyrimidin-2-yl)cyclopentane-1-carboxylate (343 mg, 85%) as a ~6:1 mixture of diastereomers. MS (ES+) $C_{16}H_{21}N_5O_2$ requires: 315. found: 316 $[M+H]^+$.

Step 6: Synthesis of 3-(4-methyl-6-((5-methyl-1H-pyrazol-3-yl)amino)pyrimidin-2-yl)cyclopentane-1-carboxylic acid

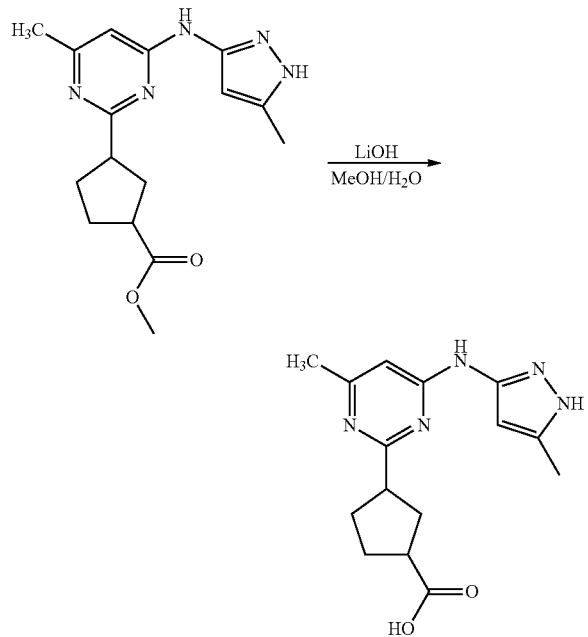

Sodium methoxide (30 wt. % in methanol, 98 mg, 0.54 mmol) was added to a solution of methyl 3-(4-methyl-6-((5-methyl-1H-pyrazol-3-yl)amino)pyrimidin-2-yl)cyclopentane-1-carboxylate (343 mg, 1.09 mmol) in methanol (11 mL) at ambient temperature. The reaction mixture was sealed and heated to 60° C. for 17 h. Analysis by LCMS showed that the ratio of diastereomers had changed from ~6:1 to 2:1. The reaction mixture was then heated at 80° C. for 2 h, 90° C. for 2 h, and then 130° C. for 30 min. After cooling to ambient temperature, analysis by LCMS showed that the ratio of diastereomers was ~1:1. Water (2 mL), and lithium hydroxide monohydrate (0.091 g, 2.2 mmol) was added and the reaction mixture was stirred at ambient temperature for 1 h. HCl (4.0 M in dioxane, 0.82 mL, 3.3 mmol) was then added and the reaction mixture was concentrated to give 3-(4-methyl-6-((5-methyl-1H-pyrazol-3-yl)amino)pyrimidin-2-yl)cyclopentane-1-carboxylic acid, which was used in the next step without any further purification.

Step 7: Synthesis of N—((S)-1-(6-(4-fluoro-1H-pyrazol-1-yl)pyridin-3-yl)ethyl)-3-(4-methyl-6-((5-methyl-1H-pyrazol-3-yl)amino)pyrimidin-2-yl)cyclopentane-1-carboxamide (Compound 106)

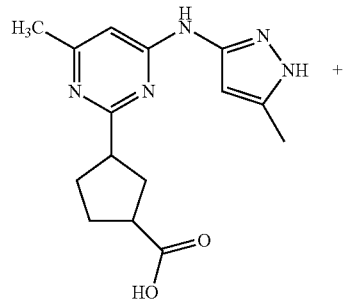

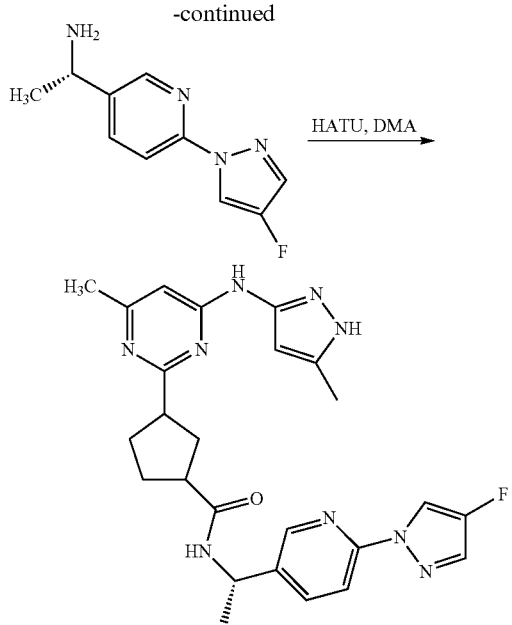

HATU (414 mg, 1.09 mmol) was added to a solution of crude 3-(4-methyl-6-((5-methyl-1H-pyrazol-3-yl)amino)pyrimidin-2-yl)cyclopentane-1-carboxylic acid (330 mg, 1.1 mmol), (S)-1-(6-(4-fluoro-1H-pyrazol-1-yl)pyridin-3-yl)ethanamine hydrochloride salt (224 mg, 0.93 mmol), and DIPEA (0.95 mL, 5.4 mmol) in DMF (10 mL) at ambient temperature. The reaction mixture was stirred for 60 min, and then was partitioned between ethyl acetate and water. The organic layer was washed with saturated aqueous sodium chloride solution, dried over sodium sulfate, filtered, and concentrated. The residue was purified by silica gel chromatography (gradient elution, 0 to 12% methanol-dichloromethane) to give N—((S)-1-(6-(4-fluoro-1H-pyrazol-1-yl)pyridin-3-yl)ethyl)-3-(4-methyl-6-((5-methyl-1H-pyrazol-3-yl)amino)pyrimidin-2-yl)cyclopentane-1-carboxamide (Compound 106; 242 mg, 45% yield) as a white solid. MS (ES+) $C_{25}H_{28}FN_9O$ requires: 489. found: 490 [M+H]$^+$.

The four stereoisomers of the cyclopentane could be separated by a two-step chiral SFC procedure. The isomeric mixture (229 mg) was dissolved in methanol (7 mL) and purified by SFC (ChiralPak AD-H 21×250 mm, 45% 2-propanol containing 0.25% DEA in $CO_2$, 2 mL injections, 70 mL/min) to give 3 peaks. Peak 1 was concentrated give 110 mg of two isomers, and was redissolved in methanol/dichloromethane (4 mL, 2 mL) and purified by SFC (ChiralPak AS 20×250 mm, 20% methanol containing 0.25% DEA in CO2, 0.5 mL injections, 70 mL/min). Peak 1 from the second chiral separation was concentrated to give (1R, 3R)—N—((S)-1-(6-(4-fluoro-1H-pyrazol-1-yl)pyridin-3-yl)ethyl)-3-(4-methyl-6-((5-methyl-1H-pyrazol-3-yl)amino)pyrimidin-2-yl)cyclopentane-1-carboxamide (Compound 109; 36 mg) as a white solid. Peak 2 from the second chiral separation was concentrated to give (1S,3S)—N—((S)-1-(6-(4-fluoro-1H-pyrazol-1-yl)pyridin-3-yl)ethyl)-3-(4-methyl-6-((5-methyl-1H-pyrazol-3-yl)amino)pyrimidin-2-yl)cyclopentane-1-carboxamide (Compound 110; 49 mg) as a white solid. Peak 2 from the first chiral separation was concentrated to give (1S,3R)—N—((S)-1-(6-(4-fluoro-1H-pyrazol-1-yl)pyridin-3-yl)ethyl)-3-(4-methyl-6-((5-methyl-1H-pyrazol-3-yl)amino)pyrimidin-2-yl)cyclopentane-1-carboxamide (Compound 107; 42 mg) as a white solid. Peak 3 from the first chiral separation was concentrated to give (1R,3S)—N—((S)-1-(6-(4-fluoro-1H-pyrazol-1-yl)pyridin-3-yl)ethyl)-3-(4-methyl-6-((5-methyl-1H-pyrazol-3-yl)amino)pyrimidin-2-yl)cyclopentane-1-carboxamide (Compound 108; 44 mg) as a white solid. The absolute stereochemistry of the cyclopentyl ring was assigned arbitrarily. Spectral data is in the compound table.

Example 3: General Synthesis of Compounds 116 and 117

Step 1: Synthesis of ethyl (1R,3R and 1S,3S)-1-methyl-3-(6-methyl-2-(methylthio)pyrimidin-4-yl)cyclopentane-1-carboxylate

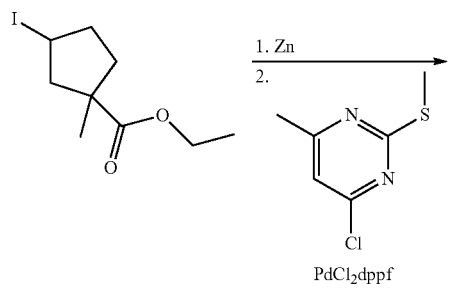

1S,3 S)-1-methyl-3-(6-methyl-2-(methylthio)pyrimidin-4-yl)cyclopentane-1-carboxylate (700 mg) as a colorless oil. MS (ES+) $C_{15}H_{22}N_2O_2S$ requires: 294. found: 295 [M+H]$^+$. $^1$H NMR (400 MHz, CDCl$_3$): δ ppm 6.67 (s, 1H), 4.17 (q, J=7.2 Hz, 2H), 3.27-3.18 (m, 1H), 2.61-2.53 (m, 4H), 2.42 (s, 3H), 2.30-2.23 (m, 1H), 2.14-2.05 (m, 1H), 2.02-1.91 (m, 1H), 1.81-1.72 (m, 2H), 1.38 (s, 3H), 1.29 (t, J=7.2 Hz, 3H).

Step 2: Synthesis of ethyl (1R,3R and 1S,3S)-1-methyl-3-(6-methyl-2-(methylsulfonyl)pyrimidin-4-yl)cyclopentane-1-carboxylate

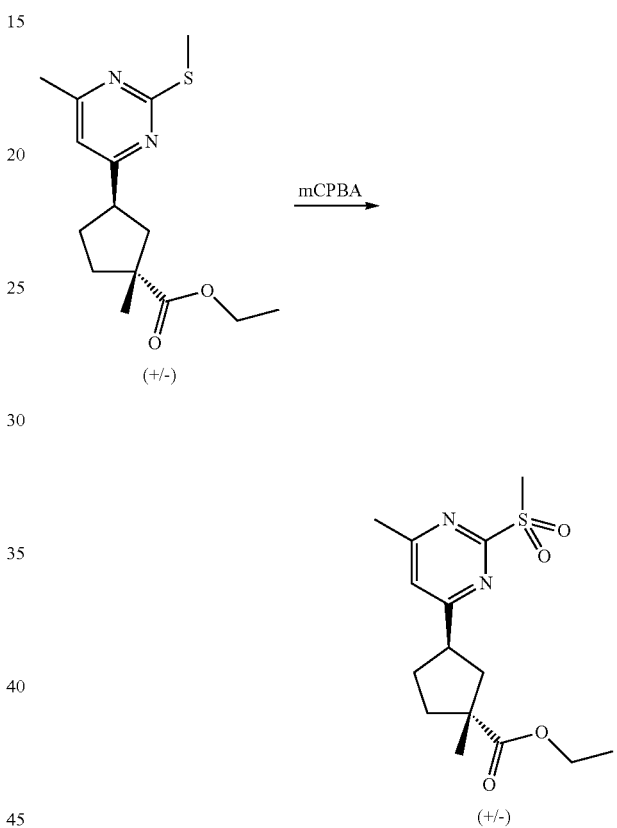

Ethyl 3-iodo-1-methylcyclopentanecarboxylate (5.60 g, 19.9 mmol) was dissolved in dimethylacetamide (66 mL) in a pressure vessel under a stream of nitrogen. Rieke Zinc (28.6 mL of a 50 mg/mL suspension in THF, 21.8 mmol) was added quickly via syringe. The vessel was capped and stirred at ambient temperature for 15 minutes. The vessel was opened under a stream of nitrogen and 4-chloro-6-methyl-2-(methylthio)pyrimidine (4.16 g, 23.8 mmol) was added followed by PdCl$_2$dppf (1.09 mg, 1.49 mmol). The vessel was capped and heated to 80° C. for 2 h. The reaction mixture was then cooled to room temperature, diluted with ethyl acetate, and filtered through celite. The filtrate was transferred to a separatory funnel and washed with water (3×), brine, and dried over sodium sulfate. The dried solution was filtered, and the filtrate was concentrated. The residue was purified by flash-column chromatography on silica gel (gradient elution, 0 to 100% ethyl acetate-hexanes) to give ethyl 1-methyl-3-(6-methyl-2-(methylthio)pyrimidin-4-yl)cyclopentane-1-carboxylate (2.1 g, 36%) as a mixture of cis and trans isomers. The isomers were separated by preparative HPLC (column: Phenomenex Gemini C18 250*50 mm*10 um; mobile phase: 45-70% water [0.05% ammonia hydroxide v/v]-ACN) to give ethyl (1R,3R and To a solution of ethyl (1R,3R and 1S,3S)-1-methyl-3-(6-methyl-2-(methylthio)pyrimidin-4-yl)cyclopentane-1-carboxylate (700 mg, 2.50 mmol) in tetrahydrofuran (15.0 mL) and water (5.0 mL) was added oxone (1.90 g, 12.5 mmol) at 10° C. The mixture was stirred at 10° C. for 16 hours. TLC indicated the starting material was consumed completely and one new spot formed. The reaction mixture was quenched by addition sodium thiosulfate (2.0 g) and stirred at 15° C. for 30 mins. The resulting solution was adjusted to pH=8 with saturated aqueous sodium bicarbonate solution and extracted with ethyl acetate (25 mL×3). The combined organic layers were washed with brine, dried over anhydrous sodium sulfate, filtered and concentrated under reduced pressure to give a residue. The crude compound (750 mg, 96% yield) was used in the next step without further purification. MS (ES+) $C_{15}H_{22}N_2O_4S$ requires: 326. found: 327 [M+H]$^+$.

Step 3: Synthesis of ethyl (1R,3R and 1S,3S)-1-methyl-3-(6-methyl-2-((5-methyl-1-(tetrahydro-2H-pyran-2-yl)-1H-pyrazol-3-yl)amino)pyrimidin-4-yl)cyclopentane-1-carboxylate

Step 4: Synthesis of ethyl (1R,3R and 1S,3S)-1-methyl-3-(6-methyl-2-((5-methyl-1H-pyrazol-3-yl)amino)pyrimidin-4-yl)cyclopentane-1-carboxylate

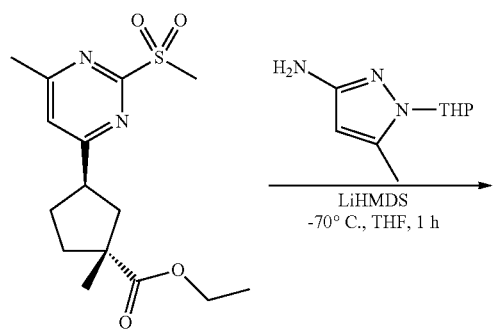

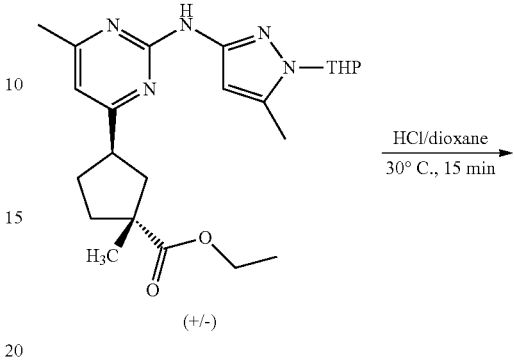

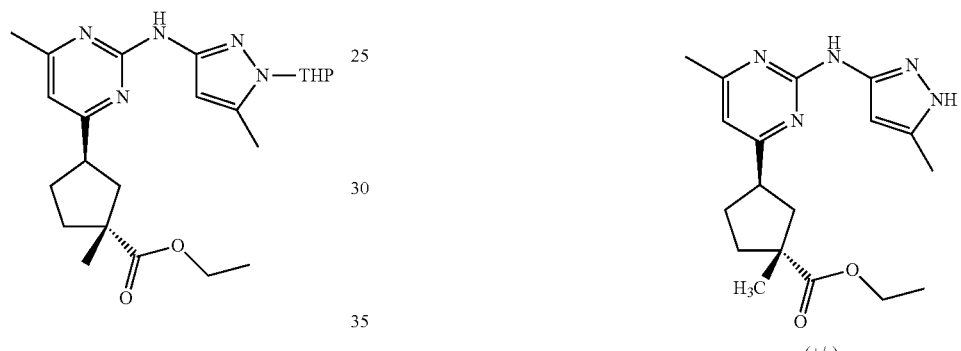

To a solution of 5-methyl-1-(tetrahydro-2H-pyran-2-yl)-1H-pyrazol-3-amine (609 mg, 3.36 mmol) in tetrahydrofuran (30.0 mL) was added LiHMDS (1 M, 3.36 mL, 3.36 mmol) dropwise at −70° C. After addition, the mixture was stirred at −70° C. for 30 min, and then compound ethyl (1R,3R and 1S,3S)-1-methyl-3-(6-methyl-2-(methylsulfonyl)pyrimidin-4-yl)cyclopentane-1-carboxylate (700 mg, 2.24 mmol) was added at −70° C. The resulting mixture was stirred at −70° C. for 30 minutes. The reaction mixture was quenched by addition water (25 mL) at 0° C. and extracted with ethyl acetate (20 mL×3). The combined organic layers were dried over anhydrous sodium sulfate, filtered and concentrated under reduced pressure to give a residue. The residue was purified by column chromatography on silica gel (gradient elution, Petroleum ether/Ethyl acetate=5:1 to 3:1) to afford crude ethyl (1R,3R and 1S,3S)-1-methyl-3-(6-methyl-2-((5-methyl-1-(tetrahydro-2H-pyran-2-yl)-1H-pyrazol-3-yl)amino)pyrimidin-4-yl)cyclopentane-1-carboxylate (700 mg) as a yellow oil. MS (ES+) $C_{23}H_{33}N_5O_3$ requires: 427. found: 428 [M+H]$^+$. $^1$H-NMR (400 MHz, CDCl$_3$): δ ppm 7.46 (s, 1H), 7.22 (s, 1H), 6.70 (s, 1H), 6.44 (s, 1H), 6.44 (s, 1H), 5.20-5.17 (m, 1H), 4.20-4.06 (m, 7H), 3.69-3.62 (m, 1H), 3.44-3.39 (m, 1H), 3.37 (s, 3H), 3.23-3.14 (m, 1H), 2.69-2.62 (m, 4H), 2.59-2.54 (m, 1H), 2.47-2.38 (m, 2H), 2.36 (d, J=2.8 Hz, 7H), 2.33-2.16 (m, 4H), 2.14-2.07 (m, 2H), 2.01-1.82 (m, 4H), 1.81-1.71 (m, 7H), 1.67-1.59 (m, 1H), 1.39 (d, J=5.6 Hz, 6H), 1.34-1.27 (m, 8H).

A solution of ethyl (1R,3R and 1S,3S)-1-methyl-3-(6-methyl-2-((5-methyl-1-(tetrahydro-2H-pyran-2-yl)-1H-pyrazol-3-yl)amino)pyrimidin-4-yl)cyclopentane-1-carboxylate (700 mg) in 4 N HCl/dioxane (20.0 mL) was stirred at 30° C. for 15 min. The reaction mixture was concentrated under reduced pressure to remove solvent. The residue was treated with saturated aqueous sodium bicarbonate solution (15 mL) and extracted with ethyl acetate (15 mL×3). The combined organic layers were dried over anhydrous sodium sulfate, filtered and concentrated under reduced pressure to give a residue. The residue was purified by flash column chromatography on silica gel (gradient elution, EA/PE=1/3~2/1) to give ethyl (1R,3R and 1S,3S)-1-methyl-3-(6-methyl-2-((5-methyl-1H-pyrazol-3-yl)amino)pyrimidin-4-yl)cyclopentane-1-carboxylate (400 mg, 71% yield) as a colorless oil. MS (ES+) $C_{18}H_{25}N_5O_2$ requires: 343. found: 344 [M+H]$^+$. $^1$H-NMR (400 MHz, CDCl3): δ ppm 7.78 (s, 2H), 6.46 (d, J=15.6 Hz, 2H), 5.91 (s, 1H), 4.12-4.06 (m, 5H), 3.19-3.10 (m, 2H), 2.55-2.48 (m, 1H), 2.40-2.35 (m, 1H), 2.32 (s, 6H), 2.30-2.25 (s, 1H), 2.23-2.20 (m, 7H), 2.10-2.00 (m, 2H), 1.93-1.84 (m, 3H), 1.70-1.64 (m, 2H), 1.60-1.52 (m, 1H), 1.29 (d, J=13.6 Hz, 6H), 1.23-1.14 (m, 7H).

Step 5: Synthesis of (1R,3R and 1S,3S)-1-methyl-3-(6-methyl-2-((5-methyl-1H-pyrazol-3-yl)amino)pyrimidin-4-yl)cyclopentane-1-carboxylic acid

Step 6: Synthesis of (1R,3R or 1S,3S)—N—((S)-1-(6-(4-fluoro-1H-pyrazol-1-yl)pyridin-3-yl)ethyl)-1-methyl-3-(6-methyl-2-((5-methyl-1H-pyrazol-3-yl)amino)pyrimidin-4-yl)cyclopentane-1-carboxamide

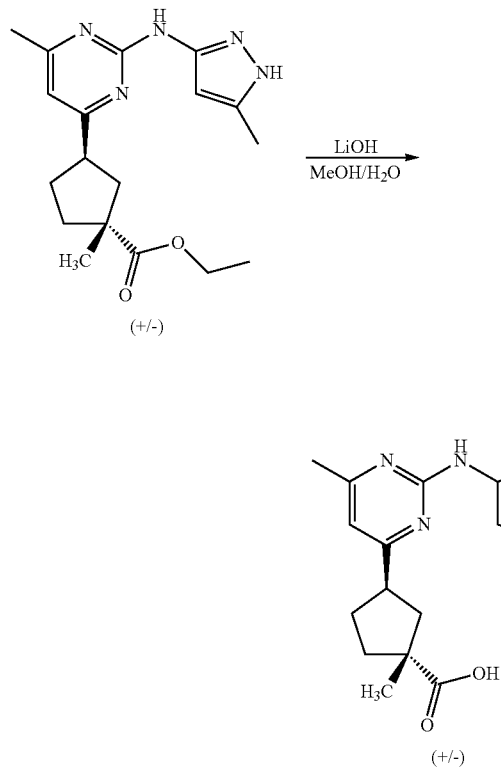

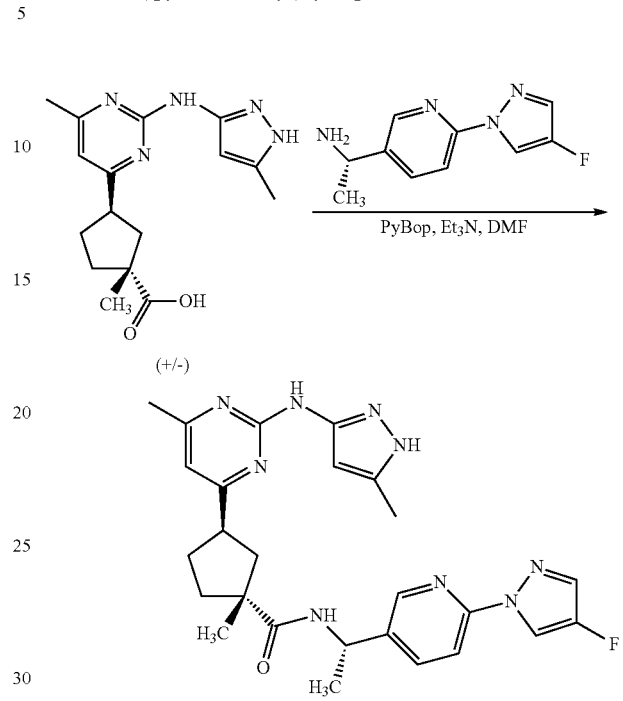

To a solution of ethyl (1R,3R and 1S,3S)-1-methyl-3-(6-methyl-2-((5-methyl-1H-pyrazol-3-yl)amino)pyrimidin-4-yl)cyclopentane-1-carboxylate (800 mg, 1.16 mmol) in methanol (20.0 mL) and water (6.0 mL) was added lithium hydroxide (165 mg, 3.49 mmol). The mixture was stirred at 60° C. for 2 h. The reaction mixture was concentrated in vacuo and then acidified by addition of 0.5 N aqueous hydrochloric acid solution. The aqueous mixture was extracted with ethyl acetate (20 mL×5). The combined organic layers were dried over anhydrous sodium sulfate and concentrated in vacuo to give the crude product (750 mg) as a white solid. NMR analysis indicated that there were two diastereomers present even though the starting material was a racemic single diastereomer. This was confirmed by analytical SFC, which showed 4 peaks. The cis and trans diastereomer pairs were separated by SFC (column: AD (250 mm*30 mm, 10 um, IPA-CO$_2$) to give the desired (1R,3R and 1S,3S) diastereomer pair as the first isomers to elute (350 mg). MS (ES+) C$_{16}$H$_{21}$N$_5$O$_2$ requires: 315. found: 344 [M+H]$^+$. $^1$HNMR (400 MHz, CD$_3$OD): δ ppm 6.64 (s, 1H), 6.28 (s, 1H), 3.98-3.91 (m, 1H), 3.29-3.19 (m, 1H), 2.66-2.61 (m, 1H), 2.38 (s, 3H), 2.36-2.31 (m, 1H), 2.27 (s, 3H), 2.14-2.06 (m, 1H), 1.99-1.89 (m, 2H), 1.70-1.62 (m, 2H), 1.35 (s, 3H), 1.17 (d, J=6.4 Hz, 6H).

To a solution of (1R,3R and 1S,3S)-1-methyl-3-(6-methyl-2-((5-methyl-1H-pyrazol-3-yl)amino)pyrimidin-4-yl)cyclopentane-1-carboxylic acid (200 mg, 0.970 mmol) in dimethyl formamide (8.0 mL) was added triethylamine (130 mg, 1.29 mmol) and PyBop (479 mg, 0.919 mmol). The mixture was stirred at 15° C. for 2 h. LCMS showed the starting material was consumed and desired product was confirmed. The mixture was quenched with water (15 mL), and extracted with ethyl acetate (20 mL×5). The combined organic layers were dried over anhydrous sodium sulfate, filtered and concentrated under reduced pressure. The residue was purified by prep-HPLC (column: Agela Durashell C18 150*25 5 um; mobile phase: [water (0.05% ammonia hydroxide v/v)-ACN]; B %: 37%-67%, 12 min) to give two isomers (150 mg, 46.7% yield). The isomers were separated by SFC (column: AS (250 mm*30 mm, 10 um), ethanol-CO$_2$ mobile phase) to give (1R,3R or 1S,3 S)—N—((S)-1-(6-(4-fluoro-1H-pyrazol-1-yl)pyridin-3-yl)ethyl)-1-methyl-3-(6-methyl-2-((5-methyl-1H-pyrazol-3-yl)amino)pyrimidin-4-yl)cyclopentane-1-carboxamide (Compounds 116 and 117, respectively; 65 mg, white solid) as the first peak to elute. Note that it is a pure single stereoisomer with determined relative stereochemistry but undetermined absolute stereochemistry of the cyclopentane ring. MS (ES+) C$_{26}$H$_{31}$FN$_9$O requires: 503. found: 504[M+H]$^+$. $^1$H-NMR (400 MHz, CDCl3): δ ppm 8.44-8.32 (m, 2H), 7.88 (d, J=8.4 Hz, 1H), 7.74 (dd, J=8.4, 2.0 Hz, 1H), 7.58 (d, J=4.0 Hz, 2H), 7.27 (s, 1H), 6.55 (s, 1H), 6.44 (d, J=5.2 Hz, 1H), 5.97 (s, 1H), 5.25-5.14 (m, 1H), 3.37-3.20 (m, 1H), 2.56-2.45 (m, 1H), 2.39 (s, 3H), 2.34-2.28 (m, 1H), 2.26 (s, 3H), 2.22-2.12 (m, 1H), 2.02-1.87 (m, 2H), 1.71-1.59 (m, 1H), 1.49 (d, J=6.8 Hz, 3H), 1.37 (s, 3H).

Example 4. Synthesis of Ketone Intermediate Ethyl 1-methyl-3-oxocyclopentane-1-carboxylate

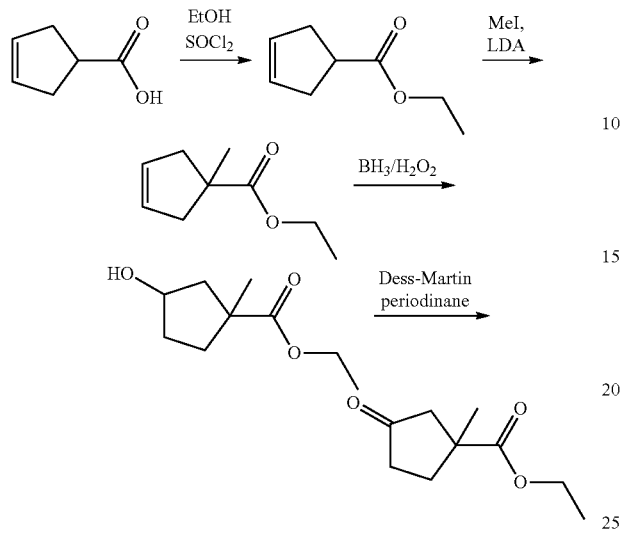

Step 1: Synthesis of ethyl cyclopent-3-ene-1-carboxylate

To a solution of 3-cyclopentene-1-carboxylic acid (200 g, 1.79 mol) in ethanol (2 L) was added thionyl chloride (106 g, 0.892 mol) dropwise at 5-10° C. The reaction mixture was stirred at room temperature for 0.5 h. The mixture was poured into water and then extracted with EtOAc (2 L). The organic layer was washed with 10% aqueous sodium carbonate, dried over anhydrous $Na_2SO_4$ and concentrated to afford ethyl cyclopent-3-ene-1-carboxylate (210 g, 84% yield) as a pale yellow oil.

Step 2: Synthesis of ethyl 1-methylcyclopent-3-ene-1-carboxylate

To a solution of ethyl cyclopent-3-ene-1-carboxylate (200 g, 1.43 mol) in THF (600 mL) was added LDA (2 M in THF, 1.1 L, 2.2 mol) dropwise at −65° C. under nitrogen. The mixture was stirred at −65° C. for 0.5 h and MeI (324 g, 2.28 mol) was added. The reaction mixture was allowed to warm to room temperature and stirred for 16 h. Aqueous ammonium chloride solution (10%, 2 L) was added to quench the reaction and the resulting mixture was extracted with EtOAc (4 L). The organic layer was washed with brine, dried over anhydrous sodium sulfate, filtered, and concentrated. The residue was purified by column chromatography on silica gel (Petroleum ether/EtOAc=100:1) to afford ethyl 1-methylcyclopent-3-ene-1-carboxylate (193 g, 87% yield) as a pale yellow oil.

Step 3: Synthesis of ethyl 3-hydroxy-1-methylcyclopentane-1-carboxylate

To a solution of ethyl 1-methylcyclopent-3-ene-1-carboxylate (135 g, 0.877 mol) in THF (2.7 L) at −5° C. was added $BH_3\text{-}Me_2S$ (10M, 132 mL, 1.32 mol) dropwise under nitrogen. The reaction mixture was stirred at room temperature for 1.5 h. Aqueous $Na_2CO_3$ (10%, 2.7 L) was added dropwise at −5° C. followed by addition of 30% $H_2O_2$ (179 g, 1.58 mol). The reaction mixture was stirred at room temperature for 16 h. EtOAc and 10% aqueous $Na_2S_2O_3$ were added and the organic layer was separated, washed with brine, dried over anhydrous $Na_2SO_4$ and concentrated to afford ethyl 3-hydroxy-1-methylcyclopentane-1-carboxylate (91 g, 60.3% yield), which was used directly in the next step without further purification.

Step 4: Synthesis of ethyl 1-methyl-3-oxocyclopentane-1-carboxylate

To a solution of ethyl 3-hydroxy-1-methylcyclopentane-1-carboxylate (191 g, 1.11 mol) in DCM (3 L) was added Dess-Martin periodinane (565 g, 1.33 mol). The reaction mixture was stirred at room temperature for 12 h. The mixture was filtered and the filtrate was concentrated. The residue was purified by column chromatography on silica gel (Petroleum ether/EtOAc=10:1) to afford compound ethyl 1-methyl-3-oxocyclopentane-1-carboxylate (101.5 g, 53.7% yield) as a light yellow oil. GC-MS (EI): m/z 170 [M]$^+$. $^1$H NMR (400 MHz, DMSO-d6) δ 4.17 (q, J=7.2 Hz, 2H), 2.77 (d, J=18.0 Hz, 1H), 2.45-2.32 (m, 3H), 2.13 (d, J=18.4 Hz, 1H), 1.95-1.90 (m, 1H), 1.38 (s, 3H), 1.25 (t, J=7.2 Hz, 3H).

Example 5. Synthesis of Iodide Intermediate Ethyl 3-iodo-1-methylcyclopentane-1-carboxylate

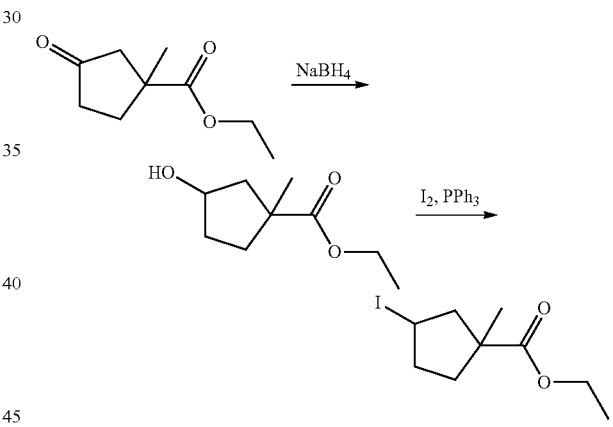

Step 1: Synthesis of ethyl 3-hydroxy-1-methylcyclopentane-1-carboxylate

Ethyl 1-methyl-3-oxocyclopentane-1-carboxylate (21.4 g, 126 mmol) was dissolved in ethanol (210 mL) and the solution was cooled to 0° C. Sodium borohydride (5.23 g, 138 mmol) was added in three portions over 20 min. The cooling bath was removed, and the reaction mixture was stirred for 16 h at ambient temperature. The reaction mixture was then quenched by addition of aqueous saturated ammonium chloride solution. The quenched reaction mixture was evaporated to remove the ethanol, and then the aqueous suspension was extracted with dichloromethane (3×). The combined organic layers were dried over sodium sulfate, filtered, and the filtrate was concentrated. The residue was purified by flash-column chromatography on silica gel (gradient elution, 15% to 60% ethyl acetate-hexanes) to afford ethyl 3-hydroxy-1-methylcyclopentane-1-carboxylate (11.6 g, 54%) as a colorless oil.

Step 2: Synthesis of ethyl 3-iodo-1-methylcyclopentane-1-carboxylate

Ethyl 3-hydroxy-1-methylcyclopentane-1-carboxylate (11.6 g, 67.4 mmol) was dissolved in THF (180 mL) and imidazole (5.96, 88.0 mmol) and triphenylphosphine (23.0 g, 88.0 mmol) were added. The mixture was cooled to 0° C., and then a solution of iodine (22.2 g, 88.0 mmol) in THF (90 mL) was added dropwise over 15 min. The reaction mixture was allowed to warm to ambient temperature and was then stirred for 40 h. The reaction mixture was then poured over saturated sodium thiosulfate solution and extracted with ethyl acetate. The organic layer was dried over sodium sulfate, and the dried solution was filtered. The filtrate was concentrated, and the residue was triturated with hexane (200 mL, stir for 20 min). The mixture was filtered, and the filtrate was evaporated. The residue was purified by flash-column chromatography on silica gel (gradient elution, 0 to 20% ethyl acetate-hexanes) to give the title compound (7.5 g, 40%) as a pale yellow oil. MS (ES+) $C_9H_{15}IO_2$ requires: 282. found: 293 [M+H]$^+$.

Example 6. Synthesis of Amine Intermediates

A. Synthesis of (S)-1-(6-(4-fluoro-1H-pyrazol-1-yl)pyridin-3-yl)ethan-1-amine

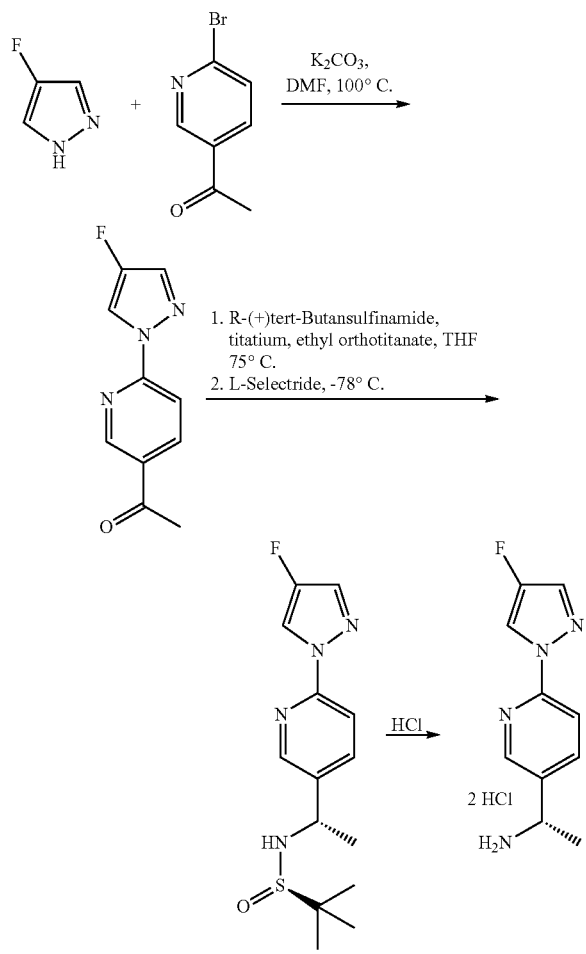

Step 1: 1-(6-(4-fluoro-1H-pyrazol-1-yl)pyridin-3-yl)ethan-1-one

4-Fluoro-1H-pyrazole (4.73 g, 55 mmol) and potassium carbonate (17.27 g, 125 mmol) were combined and stirred in N,N-dimethylformamide (41.7 mL) for 10 minutes in an open sealed tube before addition of 2-bromo-5-acetylpyridine (10 g, 50 mmol). The reaction tube was sealed and stirred 20 hours at 100° C. The reaction mixture was then cooled to room temperature and poured into water (~700 mL). The mixture was sonicated and stirred for 20 minutes. A beige solid was isolated by filtration, washed with small amounts of water, and dried to yield 1-(6-(4-fluoro-1H-pyrazol-1-yl)pyridin-3-yl)ethan-1-one (9.81 g, 96% yield). MS: M+1=206.0.

Step 2: (R)—N—((S)-1-(6-(4-fluoro-1H-pyrazol-1-yl)pyridin-3-yl)ethyl)-2-methylpropane-2-sulfinamide To a stirred room temperature solution of 1-(6-(4-fluoro-1H-pyrazol-1-yl)pyridin-3-yl)ethan-1-one (9.806 g, 47.8 mmol) in THF (96 mL) was added (R)-(−)-t-Butylsulfinamide (5.79 g, 47.8 mmol) followed by titanium (IV) ethoxide (21.8 g, 96 mmol). The solution was stirred at 75° C. on an oil bath for 15 hours. The reaction solution was cooled to room temperature and then to −78° C. (external temperature) before the next step. To the −78° C. solution was added dropwise over nearly 55 minutes L-Selectride (143 mL of 1N in THF, 143 mmol). During addition, some bubbling was observed. The reaction was then stirred after the addition was completed for 15 minutes at −78° C. before warming to room temperature. LC-MS of sample taken during removal from cold bath showed reaction was completed. The reaction was cooled to −50° C. and quenched slowly with methanol (~10 mL), then poured into water (600 mL) and stirred. An off-white precipitate was removed by filtration, with ethyl acetate used for washes. The filtrate was diluted with ethyl acetate (800 mL), the layers were separated, and the organic layer was dried over sodium sulfate, filtered, and concentrated down. The crude was purified by silica gel chromatography to yield (R)—N—((S)-1-(6-(4-fluoro-1H-pyrazol-1-yl)pyridin-3-yl)ethyl)-2-methylpropane-2-sulfinamide (10.5 g, 99% purity, 70.3% yield) as a light yellow solid. MS: M+1=311.1.

Step 3: (S)-1-(6-(4-fluoro-1H-pyrazol-1-yl)pyridin-3-yl)ethan-1-amine

A solution of (R)—N—((S)-1-(6-(4-fluoro-1H-pyrazol-1-yl)pyridin-3-yl)ethyl)-2-methylpropane-2-sulfinamide (10.53 g, 33.9 mmol)) in methanol (79 mmol) and 4N HCl/dioxane (85 mL, 339 mmol) was stirred 2.5 hours. LC-MS showed reaction was completed. The reaction solution was poured into diethyl ether (300 mL). A sticky solid was formed. The mixture was treated with ethyl acetate (200 mL) and sonicated. The solvents were decanted, and the sticky solid was treated with more ethyl acetate (~200 mL), sonicated and stirred. The bulk of the sticky solid was converted to a suspension. A light yellow solid was isolated by filtration, washed with smaller amounts of ethyl acetate, and dried to yield (S)-1-(6-(4-fluoro-1H-pyrazol-1-yl)pyridin-3-yl)ethan-1-amine (7.419 g, 78% yield). LC-MS confirmed desired product in high purity. MS: M+1=207.1.

B. Synthesis of (S)-1-(5-(4-fluoro-1H-pyrazol-1-yl)pyrazin-2-yl)ethan-1-amine

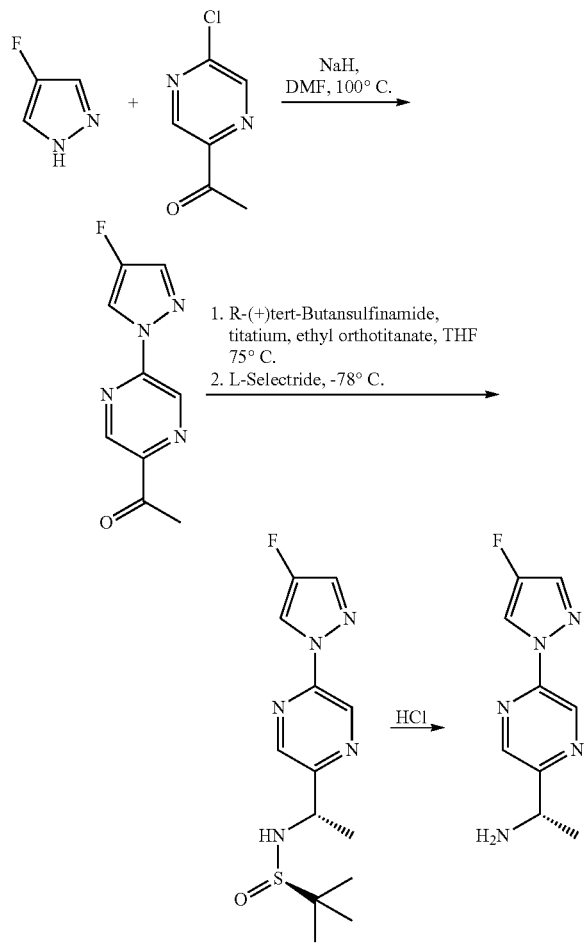

Step 1: 1-(5-(4-fluoro-1H-pyrazol-1-yl)pyrazin-2-yl)ethan-1-one

Sodium hydride (60 wt. %, 276 mg, 6.90 mmol) was added to a mixture of 1-(5-chloropyrazin-2-yl)ethanone (800 mg, 5.11 mmol) and 4-Fluoro-1H-pyrazole (484 mg, 5.62 mmol) in N,N-dimethylformamide (6.0 mL) at ambient temperature for 10 minutes. The reaction mixture was then poured into water (70 mL) and was sonicated and stirred for 20 minutes. A dark red solid was isolated by filtration, washed with small amounts of water, and dried to 1-(5-(4-fluoro-1H-pyrazol-1-yl)pyrazin-2-yl)ethan-1-one (919 mg, 95% yield). MS: M+1=207.

Step 2: (R)—N—((S)-1-(5-(4-fluoro-1H-pyrazol-1-yl)pyrazin-2-yl)ethyl)-2-methylpropane-2-sulfinamide To a stirred room temperature solution of 1-(5-(4-fluoro-1H-pyrazol-1-yl)pyrazin-2-yl)ethan-1-one (4.67 g, 22.7 mmol) in THF (45 mL) was added (R)-(−)-t-Butylsulfinamide (2.75 g, 22.7 mmol) followed by titanium (IV) ethoxide (10.3 g, 45.3 mmol). The solution was stirred at 75° C. on an oil bath for 20 hours. The reaction solution was cooled to room temperature and then to −78° C. before the next step. To the −78° C. solution was added dropwise over 50 minutes L-Selectride (50.1 mL of 1 N in THF, 50.1 mmol). During addition, some bubbling was observed. The reaction was then stirred after the addition was completed for 15 minutes at −78° C. before warming to room temperature. LC-MS of sample taken during removal from cold bath showed reaction was completed. The reaction was cooled to −60° C. and quenched slowly with methanol (1 mL), then poured into water (100 mL) and stirred. The mixture was filtered and the solids were washed further with ethyl acetate. The filtrate was diluted with ethyl acetate, the layers were separated, and the organic layer was dried over sodium sulfate. The dried solution was filtered, and the filtrate was concentrated. The residue was purified by flash-column chromatography (gradient elution, 0 to 100% ethyl acetate-dichloromethane) to give (R)—N—((S)-1-(5-(4-fluoro-1H-pyrazol-1-yl)pyrazin-2-yl)ethyl)-2-methylpropane-2-sulfinamide (1.04 g, 14%) as a brown solid. MS: M+1=312. $^1$H NMR (400 MHz, DMSO-d6) δ 9.12 (d, J=1.4 Hz, 1H), 8.73 (d, J=4.5 Hz, 1H), 8.59 (d, J=1.4 Hz, 1H), 8.03 (d, J=4.1 Hz, 1H), 5.69 (d, J=5.7 Hz, 1H), 4.62 (p, J=6.8 Hz, 3H), 1.57 (d, J=6.9 Hz, 3H), 1.12 (s, 9H).

Step 3: (S)-1-(5-(4-fluoro-1H-pyrazol-1-yl)pyrazin-2-yl)ethan-1-amine

A solution of (R)—N—((S)-1-(5-(4-fluoro-1H-pyrazol-1-yl)pyrazin-2-yl)ethyl)-2-methylpropane-2-sulfinamide (1.04 g, 3.34 mmol) in methanol (7.8 mL) and 4N HCl/dioxane (8.34 mL, 33.4 mmol) was stirred for 1.5 h at ambient temperature. The reaction mixture was poured into diethyl ether (100 mL). A light beige solid was isolated by filtration to afford (S)-1-(5-(4-fluoro-1H-pyrazol-1-yl)pyrazin-2-yl)ethan-1-amine (689 mg, 85% yield). MS: M+1=208.

C. Synthesis of (5-(4-fluoro-1H-pyrazol-1-yl)pyrazin-2-yl)methanamine

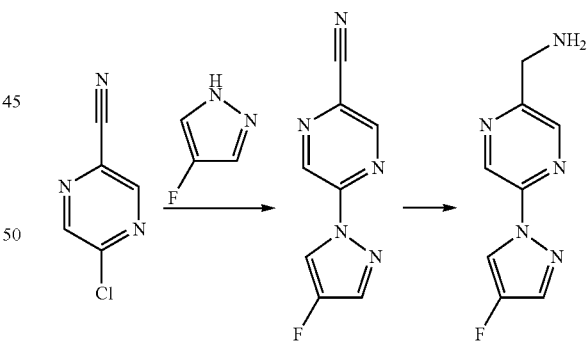

Step 1: 5-(4-fluoro-1H-pyrazol-1-yl)pyrazine-2-carbonitrile

To a solution of 5-chloropyrazine-2-carbonitrile (280 mg, 2.0 mmol) in DMF was added 4-fluoro-1H-pyrazole (170 mg, 2.0 mmol), and potassium acetate (395 mg, 4.0 mmol). The mixture was stirred at the 100° C. for 4 hours. The reaction mixture was cooled to 20° C., poured into brine (25 mL), and extracted with ethyl acetate. The organic layer was dried over sodium sulfate, concentrated and purified by column chromatography (hexane:ethyl acetate=5:1) to give 5-(4-fluoro-1H-pyrazol-1-yl)pyrazine-2-carbonitrile (310 mg, Yield 82%). The structure was confirmed by LC-MS.

Step 2: (5-(4-fluoro-1H-pyrazol-1-yl)pyrazin-2-yl)methanamine

A mixture of 5-(4-fluoro-1H-pyrazol-1-yl)pyrazine-2-carbonitrile (190 mg, 1.0 mmol) and NiCl$_2$ (12 mg, 0.1 mmol) in MeOH (5 mL) was added NaBH$_4$ (380 mg, 10 mmol) at 0° C. The mixture was stirred at 0° C. for 2 hours, quenched with aqueous NH$_4$Cl and purified by HPLC to give (5-(4-fluoro-1H-pyrazol-1-yl)pyrazin-2-yl)methanamine (160 mg, Yield 82%). The structure was confirmed by LC-MS.

D. Synthesis of (6-(3,5-dimethyl-1H-pyrazol-1-yl)pyridin-3-yl)methanamine

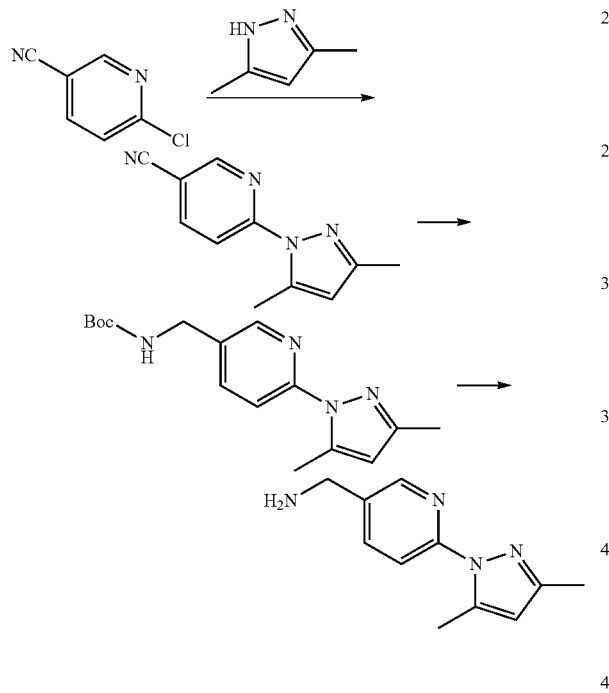

Step 1: 6-(3,5-Dimethyl-1H-pyrazol-1-yl)nicotinonitrile

To the solution of 6-chloronicotinonitrile (300 mg, 2.2 mmol) in DMF (10 mL), was added 3,5-dimethyl-1H-pyrazole (210 mg, 2.2 mmol) and Cs$_2$CO$_3$ (1.4 g, 4.4 mmol). The mixture was stirred at 90° C. for 16 h. Water (25 mL) was added to the reaction mixture, and the mixture was filtered. The solids were washed with water and dried under vacuum to give 6-(3,5-dimethyl-1H-pyrazol-1-yl)nicotinonitrile (320 mg, yield 74.6%).

Step 2: tert-Butyl ((6-(3, 5-dimethyl-1H-pyrazol-1-yl)pyridin-3-yl)methyl)carbamate To 6-(3,5-Dimethyl-1H-pyrazol-1-yl)nicotinonitrile (300 mg, 1.5 mmol) in MeOH (10 mL), was added NiCl$_2$ (19 mg, 0.15 mmol), (Boc)$_2$O (654 mg, 3.0 mmol) and NaBH$_4$ (142 mg, 3.8 mmol). The mixture was stirred at ambient temperature for 3 h. Saturated aqueous ammonium chloride solution was added and the MeOH was removed under vacuum. The aqueous suspension was then partitioned with ethyl acetate, and the layers were separated. The organic layer was washed with saturated sodium bicarbonate solution (2×50 mL). The organic layer was dried with anhydrous sodium sulfate, filtered, and concentrated under vacuum to give 450 mg target compound that was used in the next step without further purification.

Step 3: 6-(3,5-Dimethyl-1H-pyrazol-1-yl)nicotinonitrile

A solution of HCl in Dioxane (4.0 M, 10 mL) was added to compound tert-Butyl ((6-(3,5-dimethyl-1H-pyrazol-1-yl)pyridin-3-yl)methyl)carbamate (450 mg). The mixture was stirred for 2 h, then was dried under reduced pressure to give the title compound (350 mg) as a light brown solid that was used without further purification. $^1$H NMR (400 MHz, DMSO-d6) δ 8.51 (d, J=2.1 Hz, 1H), 8.34 (s, 3H), 8.03 (dd, J=8.5, 2.4 Hz, 1H), 7.87 (d, J=8.5 Hz, 1H), 6.14 (s, 1H), 4.12 (q, J=5.7 Hz, 2H), 2.59 (s, 3H), 2.21 (s, 3H).

E. Synthesis of (6-(4-chloro-1H-pyrazol-1-yl)pyridin-3-yl)methanamine

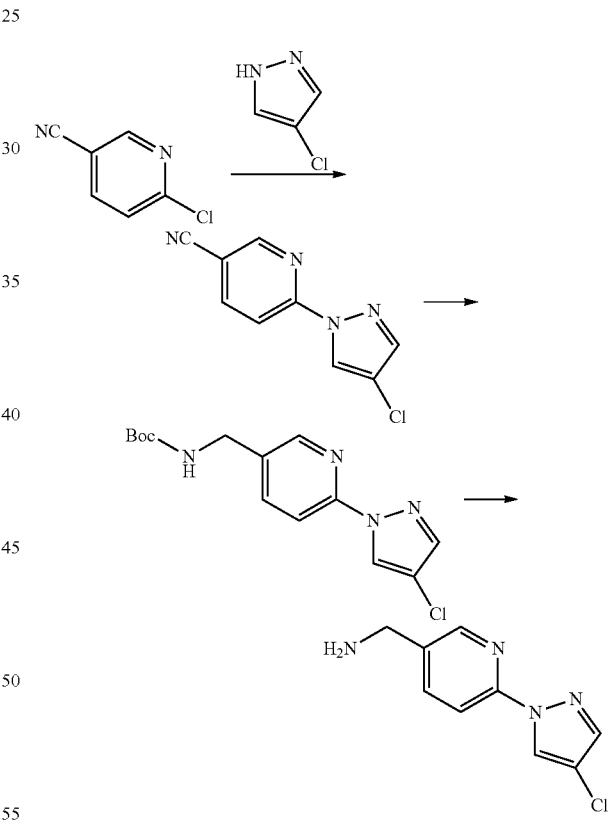

Step 1: 6-(4-Chloro-1H-pyrazol-1-yl)nicotinonitrile

To a solution of 6-chloronicotinonitrile (300 mg, 2.2 mmol) in DMF (10 mL), was added 4-chloro-1H-pyrazole (227 mg, 2.2 mmol) and Cs$_2$CO$_3$ (1.4 g, 4.4 mmol). The mixture was stirred at 90° C. for 16 h. Water (25 mL) was added to the mixture, and the mixture was filtered. The solids were washed with water and dried under vacuum to give 6-(4-Chloro-1H-pyrazol-1-yl)nicotinonitrile (380 mg, 84%).

Step 2: tert-Butyl ((6-(4-chloro-1H-pyrazol-1-yl)pyridin-3-yl)methyl)carbamate To 6-(4-chloro-1H-pyrazol-1-yl)nicotinonitrile (350 mg, 1.7 mmol) in MeOH (10 mL), was added NiCl$_2$ (19 mg, 0.17 mmol), (Boc)$_2$O (741 mg, 3.4 mmol) and NaBH$_4$ (163 mg, 4.3 mmol). The mixture was stirred at ambient temperature for 3 h. Saturated aqueous ammonium chloride solution was added and the MeOH was removed under vacuum. The aqueous suspension was then partitioned with ethyl acetate, and the layers were separated. The organic layer was washed with saturated sodium bicarbonate solution (2×50 mL). The organic layer was dried with anhydrous sodium sulfate, filtered, and concentrated under vacuum to give 480 mg target compound that was used in the next step without further purification.

Step 3: (6-(4-chloro-1H-pyrazol-1-yl)pyridin-3-yl)methanamine

A solution of HCl in Dioxane (4.0 M, 10 mL) was added to tert-Butyl ((6-(4-chloro-1H-pyrazol-1-yl)pyridin-3-yl)methyl)carbamate (450 mg, 1.5 mmol) at ambient temperature. The mixture was stirred for 2 h, then was dried under reduced pressure to give the title compound (290 mg) as a light brown solid that was used without further purification. MS: M+1=209.

F. Synthesis of (S)-1-(5-(4-fluoro-1H-pyrazol-1-yl)pyrazin-2-yl)ethan-1-amine

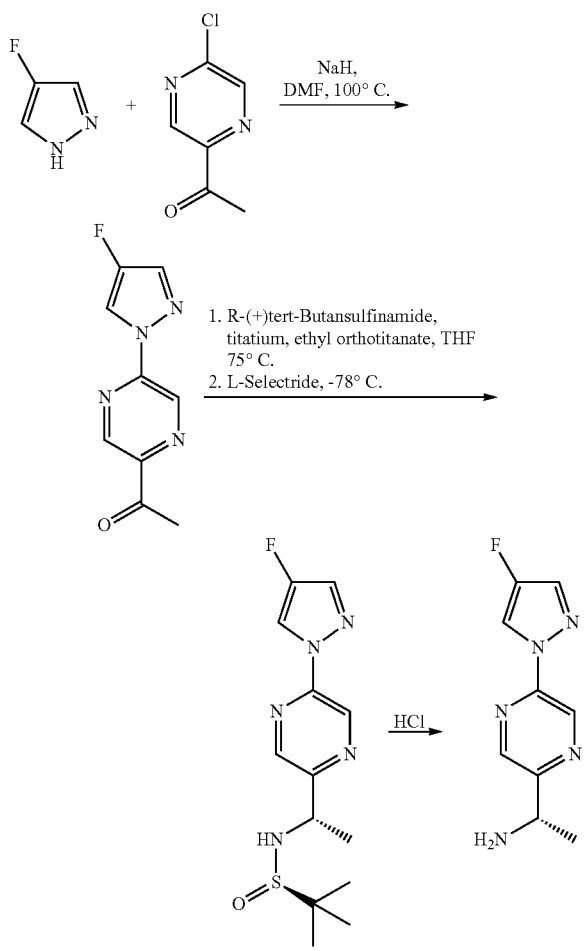

Step 1: 1-(5-(4-fluoro-1H-pyrazol-1-yl)pyrazin-2-yl)ethan-1-one

Sodium hydride (60 wt. %, 276 mg, 6.90 mmol) was added to a mixture of 1-(5-chloropyrazin-2-yl)ethanone (800 mg, 5.11 mmol) and 4-Fluoro-1H-pyrazole (484 mg, 5.62 mmol) in N,N-dimethylformamide (6.0 mL) at ambient temperature for 10 minutes. The reaction mixture was then poured into water (70 mL) and was sonicated and stirred for 20 minutes. A dark red solid was isolated by filtration, washed with small amounts of water, and dried to 1-(5-(4-fluoro-1H-pyrazol-1-yl)pyrazin-2-yl)ethan-1-one (919 mg, 95% yield). MS: M+1=207.

Step 2: (R)—N—((S)-1-(5-(4-fluoro-pyrazol-1-yl)pyrazin-2-yl)ethyl)-2-methylpropane-2-sulfinamide To a stirred room temperature solution of 1-(5-(4-fluoro-1H-pyrazol-1-yl)pyrazin-2-yl)ethan-1-one (4.67 g, 22.7 mmol) in THF (45 mL) was added (R)-(−)-t-Butylsulfinamide (2.75 g, 22.7 mmol) followed by titanium (IV) ethoxide (10.3 g, 45.3 mmol). The solution was stirred at 75° C. on an oil bath for 20 hours. The reaction solution was cooled to room temperature and then to −78° C. before the next step. To the −78° C. solution was added dropwise over 50 minutes L-Selectride (50.1 mL of 1 N in THF, 50.1 mmol). During addition, some bubbling was observed. The reaction was then stirred after the addition was completed for 15 minutes at −78° C. before warming to room temperature. LC-MS of sample taken during removal from cold bath showed reaction was completed. The reaction was cooled to −60° C. and quenched slowly with methanol (1 mL), then poured into water (100 mL) and stirred. The mixture was filtered and the solids were washed further with ethyl acetate. The filtrate was diluted with ethyl acetate, the layers were separated, and the organic layer was dried over sodium sulfate. The dried solution was filtered, and the filtrate was concentrated. The residue was purified by flash-column chromatography (gradient elution, 0 to 100% ethyl acetate-dichloromethane) to give (R)—N—((S)-1-(5-(4-fluoro-1H-pyrazol-1-yl)pyrazin-2-yl)ethyl)-2-methylpropane-2-sulfinamide (1.04 g, 14%) as a brown solid. MS: M+1=312. $^1$H NMR (400 MHz, DMSO-d6) δ 9.12 (d, J=1.4 Hz, 1H), 8.73 (d, J=4.5 Hz, 1H), 8.59 (d, J=1.4 Hz, 1H), 8.03 (d, J=4.1 Hz, 1H), 5.69 (d, J=5.7 Hz, 1H), 4.62 (p, J=6.8 Hz, 3H), 1.57 (d, J=6.9 Hz, 3H), 1.12 (s, 9H).

Step 3: (S)-1-(5-(4-fluoro-1H-pyrazol-1-yl)pyrazin-2-yl)ethan-1-amine

A solution of (R)—N—((S)-1-(5-(4-fluoro-1H-pyrazol-1-yl)pyrazin-2-yl)ethyl)-2-methylpropane-2-sulfinamide (1.04 g, 3.34 mmol) in methanol (7.8 mL) and 4N HCl/dioxane (8.34 mL, 33.4 mmol) was stirred for 1.5 h at ambient temperature. The reaction mixture was poured into diethyl ether (100 mL). A light beige solid was isolated by filtration to afford (S)-1-(5-(4-fluoro-1H-pyrazol-1-yl)pyrazin-2-yl)ethan-1-amine (689 mg, 85% yield). MS: M+1=208.

Example 7. Other Compounds

The specific synthetic protocols set forth previously were used to prepare other compounds of the disclosure as indicated in the table below. The NMR and LC MS data obtained for those compounds are also shown.

TABLE 5

| Compound Number | Synthetic Protocol | ¹H-NMR | MS (M + 1) |
|---|---|---|---|
| 100 | 1 | ¹H-NMR (400 MHz, DMSO-d6) δ 14.62 (s, 1H), 12.80 (s, 1H), 11.51 (s, 1H), 8.84 (t, J = 5.9 Hz, 1H), 7.35 (dd, J = 9.2, 5.5 Hz, 2H), 7.27 (d, J = 7.2 Hz, 4H), 7.14 (d, J = 4.9 Hz, 1H), 6.96 (s, 1H), 5.81 (s, 1H), 4.33 (d, J = 5.8 Hz, 2H), 3.17 (s, 1H), 2.44 (s, 3H), 2.33 (dd, J = 13.7, 9.8 Hz, 2H), 2.17 (dt, J = 23.1, 11.2 Hz, 4H), 2.07-1.90 (m, 4H), 1.03-0.95 (m, 2H), 0.82-0.74 (m, 2H). | 432 |
| 101 | 1 | ¹H-NMR (400 MHz, DMSO-d6) δ ppm 11.64 (s, 1H), 8.90 (br. s., 1H), 8.59 (dd, 1H, J = 2.8, 0.8 Hz), 8.48-8.45 (m, 1H), 8.34 (d, 1H, J = 1.2 Hz), 7.90-7.87 (m, 1H), 7.89-7.80 (m, 1H), 7.79 (s, 1H), 6.89 (br. s., 1H), 6.86 (s, 1H), 6.55 (dd, 1H, J = 2.4, 1.6 Hz), 6.17 (br. s, 1H), 5.03 (s, 1H), 4.35-4.33 (m, 2H), 3.13-3.03 (m, 1H), 2.45-2.32 (m, 1H), 2.30-2.22 (m, 1H), 2.21 (s, 3H), 2.15 (s, 3H), 2.10-2.00 (m, 1H), 1.96-1.90 (m, 2H), 1.76-1.67 (m, 1H). | 473 |
| 102 | 1 | ¹H-NMR (400 MHz, DMSO-d6) δ ppm 11.64 (s, 1H), 8.90 (br. s., 1H), 8.59 (dd, 1H, J = 2.8, 0.8 Hz), 8.47-8.45 (m, 1H), 8.34 (d, 1H, J = 1.2 Hz), 7.90-7.81 (m, 2H), 7.80 (s, 1H), 6.89 (br. s,, 1H), 6.86 (s, 1H), 6.55 (dd, 1H, J = 2.4, 1.6 Hz), 6.17 (br. s., 1H), 5.03 (s, 1H), 4.35-4.33 (m, 2H), 3.13-3.03 (m, 1H), 2.45-2.32 (m, 1H), 2.30-2.22 (m, 1H), 2.21 (s, 3H), 2.15 (s, 3H), 2.10-2.00 (m, 1H), 1.96-1.90 (m, 2H), 1.76-1.67 (m, 1H). | 473 |
| 103 | 1 | ¹H-NMR (400 MHz, DMSO-d6) δ ppm 11.67 (s, 1H), 8.81 (s, 1H), 8.60 (dd, 1H, J = 2.8, 0.4 Hz), 8.60-8.57 (m, 1H), 8.36 (d, 1H, J = 1.2 Hz), 7.91-7.85 (m, 2H), 7.80 (s, 1H), 6.88 (br. s, 1H), 6.83 (s, 1H), 6.56 (dd, 1H, J = 2.4, 1.2 Hz), 6.09 (br. s., 1H), 5.52 (s, 1H), 4.35 (d, 2H, J = 6.4 Hz), 3.03-2.96 (m, 1H), 2.55-2.35 (m, 2H), 2.20 (s, 3H), 2.17 (s, 3H), 2.15-2.10 (m, 1H), 2.07-2.00 (m, 2H), 1.96-1.90 (m, 1H), 1.80-1.75 (m, 1H). | 473 |
| 104 | 1 | ¹H-NMR (400 MHz, DMSO-d6) δ ppm 11.67 (s, 1H), 8.81 (s, 1H), 8.61-8.57 (m, 2H), 8.36 (d, 1H, J = 1.6 Hz), 7.90-7.87 (m, 2H), 7.80 (s, 1H), 6.88 (br. s, 1H), 6.83 (s, 1H), 6.57 (dd, 1H, J = 2.4, 1.6 Hz), 6.09 (br. s., 1H), 5.52 (s, 1H), 4.35 (d, 2H, J = 6.4 Hz), 3.03-2.96 (m, 1H), 2.55-2.35 (m, 2H), 2.20 (s, 3H), 2.17 (s, 3H), 2.15-2.10 (m, 1H), 2.07-2.00 (m, 2H), 1.96-1.90 (m, 1H), 1.80-1.75 (m, 1H). | 473 |
| 105 | 1 | ¹H-NMR (400 MHz, DMSO-d6) δ 14.80-14.51 (m, 1H), 12.96-12.69 (m, 1H), 11.64-11.35 (m, 1H), 8.77 (t, J = 5.7 Hz, 1H), 7.39-7.30 (m, 1H), 7.15 (dd, J = 20.7, 10.2 Hz, 3H), 6.93 (dd, J = 32.6, 11.3 Hz, 3H), 5.81 (s, 1H), 4.24 (d, J = 5.7 Hz, 2H), 4.00 (q, J = 7.0 Hz, 2H), 3.17 (s, 1H), 2.42 (d, J = 12.9 Hz, 3H), 2.36-1.90 (m, 8H), 1.31 (t, J = 7.0 Hz, 3H), 0.99 (td, J = 6.5, 4.2 Hz, 2H), 0.81-0.75 (m, 2H). | 476 |
| 110 | 2 | ¹H-NMR (400 MHz, DMSO-d6) δ 11.85 (s, 1H), 9.45 (s, 1H), 8.63 (t, J = 4.1 Hz, 1H), 8.37-8.28 (m, 2H), 7.91-7.79 (m, 3H), 6.79 (s, 1H), 6.08 (s, 1H), 4.95 (p, J = 7.2 Hz, 1H), 3.24-3.06 (m, 2H), 2.82 (p, J = 7.8 Hz, 1H), 2.19 (s, 3H), 2.14 (s, 3H), 2.12-1.70 (m, 5H), 1.35 (d, J = 7.0 Hz, 3H). | 490 |
| 111 | 1 | ND, mixture of isomers | 501 |
| 112 | 2 | ¹H-NMR (400 MHz, DMSO-d6) δ 11.87 (s, 1H), 9.49 (s, 1H), 8.64 (d, J = 4.5 Hz, 1H), 8.36 (d, J = 2.2 Hz, 1H), 7.97 (d, J = 7.8 Hz, 1H), 7.92-7.87 (m, 2H), 7.83 (d, J = 8.5 Hz, 1H), 6.84 (b.s., 1H), 6.12 (b.s., 1H), 5.03 (p, J = 7.1 Hz, 1H), 3.25 (dd, J = 17.9, 8.6 Hz, 1H), 2.27 (dd, J = 25.3, 12.6 Hz, 2H), 2.20 (s, 3H), 2.15 (s, 3H), 2.02 (dq, J = 13.6, 7.8 Hz, 1H), 1.91 (dq, J = 16.6, 8.7 Hz, 2H), 1.53 (dt, J = 14.3, 7.4 Hz, 1H), 1.43 (d, J = 7.1 Hz, 3H), 1.27 (s, 3H). | 504 |
| 113 | 2 | ¹H-NMR (400 MHz, DMSO-d6) δ 11.88 (s, 1H), 9.51 (s, 1H), 8.67 (d, J = 4.5 Hz, 1H), 8.38 (d, J = 2.3 Hz, 1H), 7.98 (d, J = 7.8 Hz, 1H), 7.95-7.89 (m, 2H), 7.86 (d, J = 8.5 Hz, 1H), 6.82 (b.s., 1H), 6.15 (b.s., 1H), 5.02 (p, J = 7.0 Hz, 1H), 3.25 (dd, J = 18.2, 8.9 Hz, 1H), 2.34-2.26 (m, 1H), 2.21 (s, 3H), 2.15 (s, 3H), 2.07-1.83 (m, 4H), 1.52 (dt, J = 13.9, 7.5 Hz, 1H), 1.41 (d, J = 7.1 Hz, 3H), 1.26 (s, 3H). | 504 |

TABLE 5-continued

| Compound Number | Synthetic Protocol | ¹H-NMR | MS (M + 1) |
|---|---|---|---|
| 114 | 2 | ¹H-NMR (400 MHz, DMSO-d6) δ 11.89 (s, 1H), 9.49 (s, 1H), 8.67 (d, J = 4.5 Hz, 1H), 8.39 (d, J = 2.2 Hz, 1H), 8.04 (d, J = 7.8 Hz, 1H), 7.96-7.89 (m, 2H), 7.87 (d, J = 8.5 Hz, 1H), 5.07-5.00 (m, 1H), 3.05 (dt, J = 18.3, 9.3 Hz, 1H), 2.26-2.14 (m, 7H), 1.98-1.86 (m, 3H), 1.79-1.71 (m, 1H), 1.64-1.55 (m, 1H), 1.44 (d, J = 7.1 Hz, 3H). | 504 |
| 115 | 2 | ¹H-NMR (400 MHz, DMSO-d6) δ 11.89 (s, 1H), 9.49 (s, 1H), 8.68 (d, J = 4.5 Hz, 1H), 8.39 (s, 1H), 8.06 (d, J = 7.8 Hz, 1H), 7.92 (td, J = 7.8, 7.1, 3.2 Hz, 2H), 7.87 (d, J = 8.5 Hz, 1H), 5.07-5.00 (m, 1H), 3.09 (dt, J = 17.4, 7.9 Hz, 1H), 2.26-2.11 (m, 7H), 1.97-1.83 (m, 3H), 1.80-1.71 (m, 1H), 1.63-1.53 (m, 1H), 1.44 (d, J = 7.1 Hz, 3H). | 504 |
| 118 | 1 | ¹H-NMR (400 MHz, DMSO-d6) δ ppm 11.67 (s, 1H), 8.79 (s, 1H), 8.68-8.65 (m, 1H), 8.54-8.52 (m, 1H), 8.40-8.39 (m, 1H), 7.94-7.85 (m, 3H), 6.87-6.80 (m, 2H), 6.09 (s, 1H), 5.51 (d, 1H, J = 10.4 Hz), 5.02-4.98 (m, 1H), 3.04-2.95 (m, 1H), 2.42-2.37 (m, 1H), 2.19-2.16 (m, 6H), 2.08-1.71 (m, 5H), 1.41 (d, 3H, J = 6.8 Hz). | 505 |
| 119 | 1 | ¹H-NMR (500 MHz, DMSO-d6) δ ppm 11.61 (s, 1H), 8.78 (s, 1H), 8.62 (d, 1H, J = 5.0 Hz), 8.42 (d, 1H, J = 7.5 Hz), 8.35 (s, 1H), 7.91-7.81 (m, 3H), 6.87 (s, 1H), 6.78 (s, 1H), 6.10 (s, 1H), 5.07 (s, 1H), 5.00 (quintet, 1H, J = 7.5 Hz), 3.12-3.06 (m, 1H), 2.28-2.20 (m, 2H), 2.19 (s, 3H), 2.09 (s, 3H), 2.07-2.03 (m, 1H), 1.97-1.90 (m, 1H), 1.88-1.81 (m, 1H), 1.75-1.67 (m, 1H), 1.40 (d, 3H, J = 6.5 Hz). | 505 |
| 120 | 1 | ¹H-NMR (500 MHz, DMSO-d6) δ ppm 11.65 (s, 1H), 8.83 (s, 1H), 8.66 (d, 1H, J = 4.0 Hz), 8.41 (d, 1H, J = 7.5 Hz), 8.39 (d, 1H, J = 2.0 Hz), 7.94-7.86 (m, 3H), 6.84 (s, 1H), 6.80 (s, 1H), 6.17 (s, 1H), 5.08 (s, 1H), 4.99 (quintet, 1H, J = 7.5 Hz), 3.09 (quintet, 1H, J = 7.5 Hz), 2.42-2.34 (m, 1H), 2.20 (s, 3H), 2.20-2.15 (m, 1H), 2.13 (s, 3H), 2.10-1.99 (m, 1H), 1.89-1.75 (m, 2H), 1.72-1.65 (m, 1H), 1.39 (d, 3H, J = 7.0 Hz). | 505 |
| 123 | 1 | ND, mixture of isomers | 506 |
| 124 | 1 | ¹H-NMR (400 MHz, DMSO-d6) δ 11.65 (s, 1H), 9.12 (d, J = 1.4 Hz, 1H), 8.78 (s, 1H), 8.71 (d, J = 4.5 Hz, 1H), 8.55 (d, J = 7.3 Hz, 1H), 8.48 (d, J = 1.4 Hz, 1H), 8.01 (d, J = 4.2 Hz, 1H), 6.87 (s, 1H), 6.80 (s, 1H), 6.08 (s, 1H), 5.46 (s, 1H), 5.07 (p, J = 7.1 Hz, 1H), 3.02 (tt, J = 11.5, 5.7 Hz, 1H), 2.44-2.34 (m, 1H), 2.19 (s, 3H), 2.17 (s, 3H), 2.08-1.98 (m, 2H), 1.88-1.71 (m, 3H), 1.45 (d, J = 7.0 Hz, 3H). | 506 |
| 125 | 1 | ¹H-NMR (400 MHz, DMSO-d6) δ 11.66 (s, 1H), 9.13 (d, J = 1.3 Hz, 1H), 8.78 (s, 1H), 8.73 (d, J = 4.5 Hz, 1H), 8.57 (d, J = 7.4 Hz, 1H), 8.48 (d, J = 1.4 Hz, 1H), 8.02 (d, J = 4.2 Hz, 1H), 6.88 (s, 1H), 6.81 (s, 1H), 6.08 (s, 1H), 5.48 (s, 1H), 5.07 (p, J = 6.9 Hz, 1H), 3.08-2.99 (m, 1H), 2.40 (t, J = 11.5 Hz, 1H), 2.19 (s, 3H), 2.18 (s, 3H), 2.13-2.01 (m, 2H), 1.97-1.85 (m, 2H), 1.73 (dd, J = 11.6, 7.5 Hz, 1H), 1.44 (d, J = 7.0 Hz, 3H). | 506 |
| 126 | 1 | ND, mixture of isomers | 507 |
| 127 | 1 | ¹H-NMR (400 MHz, DMSO-d6) δ 14.63 (s, 1H), 12.80 (s, 1H), 11.50 (s, 1H), 8.88 (t, J = 5.7 Hz, 1H), 8.69 (d, J = 3.9 Hz, 1H), 8.38 (s, 1H), 7.94 (d, J = 4.3 Hz, 1H), 7.92-7.87 (m, 2H), 7.13 (d, J = 5.8 Hz, 1H), 6.95 (s, 1H), 5.82 (s, 1H), 4.38 (d, J = 5.7 Hz, 2H), 3.15 (s, 1H), 2.44 (s, 3H), 2.36-2.30 (m, 1H), 2.22-1.91 (m, 7H), 1.02-0.96 (m, 2H), 0.81-0.75 (m, 2H). | 517 |
| 128 | 1 | ¹H-NMR (400 MHz, CDCl3): δ ppm 8.44 (d, J = 2.0 Hz, 1 H), 8.40 (d, J = 4.4 Hz, 1 H), 8.14 (s, 1 H), 7.91 (d, J = 8.4 Hz, 1 H), 7.81-7.85 (m, 1 H), 7.60 (d, J = 4.4 Hz, 1 H), 6.95 (s, 2 H), 6.72 (s, 1 H), 6.11 (s, 1 H), 5.92 (s, 1 H), 5.0.5-5.13 (m, 1 H), 2.36-2.43 (m, 2 H), 2.33 (d, J = 3.6 Hz, 6 H), 2.15-2.28 (m, 1 H), 1.96-2.08 (m, 2 H), 1.80-1.90 (m, 1 H), 1.53 (d, J = 6.8 Hz, 3 H), 1.39 (s, 3 H). | 519 |

TABLE 5-continued

| Compound Number | Synthetic Protocol | $^1$H-NMR | MS (M + 1) |
|---|---|---|---|
| 129 | 1 | $^1$H-NMR (400 MHz, CDCl3): δ ppm 8.35-8.44 (m, 1 H), 8.08 (s, 1 H), 7.91 (d, J = 8.8 Hz, 1 H), 7.81-7.85 (m, 1 H), 7.58 (d, J = 4.4 Hz, 1 H), 6.95 (s, 1 H), 6.78 (s, 1 H), 6.71 (s, 1 H), 6.04 (s, 1 H), 5.91 (s, 1 H), 5.12-5.15 (m, 1 H), 2.46-2.57 (m, 1 H), 2.33 (d, J = 3.6 Hz, 6 H), 2.16-2.30 (m, 1 H), 1.89-2.06 (m, 3 H), 1.56 (d, J = 6.8 Hz, 3 H), 1.40 (s, 3 H). | 519 |

Example 8: Measurement of Biochemical Activity of Compounds

In order to assess the activity of chemical compounds against the relevant kinase of interest, the Caliper Life-Sciences electrophoretic mobility shift technology platform was used. Fluorescently labeled substrate peptide is incubated in the presence of kinase and ATP so that a reflective proportion of the peptide was phosphorylated. At the end of the reaction, the mix of phosphorylated (product) and non-phosphorylated (substrate) peptides were passed through the microfluidic system of the Caliper EZ Reader 2, under an applied potential difference. The presence of the phosphate group on the product peptide provided a difference in mass and charge between those of the substrate peptide, resulting in a separation of the substrate and product pools in the sample. As the pools pass a LEDS within the instrument, these pools were detected and resolved as separate peaks. The ratio between these peaks therefore reflects the activity of the chemical matter at that concentration in that well, under those conditions.

A. RET Wild Type Assay at KM

In each well of a 384-well plate, 7.5 nM-10 nM of wild type RET (ProQinase 1090-0000-1) was incubated in a total of 12.5 µL of buffer (100 mM HEPES pH 7.5, 0.015% Brij 35, 10 mM MgCl$_2$, 1 mM DTT) with 1 µM CSKtide (FITC-AHA-KKKKD DIYFFFG-NH2) (SEQ ID NO: 5) and 25 µM ATP at 25° C. for 120 minutes in the presence or absence of a dosed concentration series of compound (1% DMSO final concentration). The reaction was stopped by the addition of 70 µL of Stop buffer (100 mM HEPES pH 7.5, 0.015% Brij 35, 35 mM EDTA and 0.2% of Coating Reagent 3 (Caliper Lifesciences)). The plate was then read on a Caliper EZReader 2 (protocol settings: −1.7 psi, upstream voltage −500, downstream voltage −3000, post sample sip 35 s). Data was normalized to 0% and 100% inhibition controls and the IC$_{50}$ calculated using a 4-parameter fit in the CORE LIMS.

B. RET V804L Gatekeeper Mutant Assay at KM

In each well of a 384-well plate, 7.5 nM-10 nM of mutant RET (ProQinase 1096-0000-1) was incubated in a total of 12.5 µL of buffer (100 mM HEPES pH 7.5, 0.015% Brij 35, 10 mM MgCl2, 1 mM DTT) with 1 µM CSKtide (FITC-AHA-KKKKDDIYFFFG-NH2) (SEQ ID NO: 5) and 10 µM ATP at 25° C. for 120 minutes in the presence or absence of a dosed concentration series of compound (1% DMSO final concentration). The reaction was stopped by the addition of 70 µL of Stop buffer (100 mM HEPES pH 7.5, 0.015% Brij 35, 35 mM EDTA and 0.2% of Coating Reagent 3 (Caliper Lifesciences)). The plate was then read on a Caliper EZReader 2 (protocol settings: −1.7 psi, upstream voltage −500, downstream voltage −3000, post sample sip 35 s). Data was normalized to 0% and 100% inhibition controls and the IC$_{50}$ calculated using a 4-parameter fit in the CORE LIMS.

In Table 6 below, the following designations are used: <10.00 nM=A; 10.01-100.0 nM=B; >100 nM=C; and ND=not determined.

TABLE 6

| Compound # | RET IC$_{50}$ | V804L IC$_{50}$ |
|---|---|---|
| 100 | B | A |
| 101 | B | A |
| 102 | B | B |
| 103 | A | A |
| 104 | B | A |
| 105 | A | A |
| 106 | A | A |
| 107 | B | B |
| 108 | B | B |
| 109 | A | A |
| 110 | A | A |
| 111 | A | A |
| 112 | C | B |
| 113 | B | B |
| 114 | A | A |
| 115 | A | ND |
| 116 | A | A |
| 117 | A | A |
| 118 | A | A |
| 119 | A | A |
| 120 | B | B |
| 121 | A | ND |
| 122 | A | A |
| 123 | A | A |
| 124 | A | A |
| 125 | B | A |
| 126 | A | A |
| 127 | A | A |
| 128 | A | A |
| 129 | A | A |

Example 9: Compounds Disclosed Herein are Potent Inhibitors of Wild-Type and Mutant RET In some embodiments, compounds according to structural Formula (I), (Ia), (Ib), (II), and (III) are potent and selective inhibitors of oncogenic RET mutant and fusion proteins. Currently, there are no approved inhibitors that selectively target these disease-driving RET alterations.

1. Additional In Vitro Assays

A compound described herein can be further tested in vitro for inhibition of other mutant RET kinases, including e.g., RET V804M, and RET M918T kinases, as well as CCDC6-RET and KIF5B-RET fusion kinases. The IC$_{50}$ can be calculated.

2. Additional Cellular Assays

In cellular systems, the activity of a compound of structural Formula (I), (Ia), (Ib), (II), or (III) can be measured by inhibition of RET mutant or RET fusion autophosphorylation, RET-dependent signaling, and by inhibition of RET dependent cell proliferation. More specifically, the compound can be assayed for activity in cancer cell lines endogenously expressing activated RET fusions or other mutants. Exemplary cells that can be used for these studies include patient xenografts and established cell lines. Exemplary patient xenografts include colorectal cancer patient derived xenograft, Lung adenocarcinoma patient derived xenograft, and NSCLC patient derived xenograft. Exemplary cell lines include Ba/F3-KIF5B-RET (a model for leukemia), LC2/ad cells (a model for lung cancer), MZ-CRC 1 (a model for thyroid cancer), and TT cells (a medullary thyroid cancer cell line). Exemplary RET mutations that can be used for these studies include fusions such as KIF5B-RET and CCDC6-RET; point mutations such as RET C634W, RET V804L, RET V804E, RET V804M, and RET M918T; and fusions containing point mutations such as KIF5B-RET (V804L) and KIF5B-RET (V804M). KIF5B-RET (V804L) refers to a mutant RET that comprises a fusion with KIF5B and further comprises a V804L mutation in RET (referring the amino acid numbering of wild-type RET). KIF5B-RET (V804M) refers to a mutant RET that comprises a fusion with KIF5B and further comprises a V804M mutation in RET.

2a. Autophosphorylation Assays

As an example of an autophosphorylation assay, in Ba/F3 models engineered to express KIF5B RET, the compound is tested for its ability to inhibit RET fusion protein signaling as measured by inhibition of RET autophosphorylation. $IC_{50}$ can be calculated. Wild-type RET inhibitors cabozantinib and vandetanib can be used as controls (less potent compounds than the test compound) in these cellular assays. In some embodiments, the compound of structural Formula (I), (Ia), (Ib), (II), or (III) potently and selectively inhibit RET autophosphorylation.

The compound can also be tested for ability to inhibit RET autophosphorylation in LC2/ad cells, a non-engineered NSCLC cell line that expressed a CCDC6-RET fusion (Suzuki et al, 2013 Cancer Sci. 104, 896-903). For instance, immunoblot is performed for LC2/ad cells expressing the CCDC6-RET fusion protein and treated with the test compound at different concentrations; Phosphorylated (phospho [Y1062]) and total protein levels of RET are measured.

2b. Proliferation Assays

In some embodiments, the compound of structural Formula (I), (Ia), (Ib), (II), or (III) inhibits proliferation.

In proliferation assays, the compound can be tested for ability to inhibit KIF5B-RET dependent Ba/F3 cell growth. The $IC_{50}$ can be calculated.

Inhibition of RET activity with the compound can also be tested for inhibition of proliferation of the CCDC6-RET expressing cell line. Similarly, the compound can also be tested for its ability to inhibit RET pathway signaling and RET dependent proliferation in the human MTC TT and MZ-CRC 1 cell lines, driven by RET C634W or RET M918T mutations, respectively. In some embodiments, in RET-driven cell lines, the test compound inhibits RET activity and RET-driven proliferation more potently than the multi-kinase inhibitors such as cabozantinib and vandetanib.

2c. Downstream Signalling Assays

In LC2/ad cells, a non-engineered NSCLC cell line that expressed a CCDC6-RET fusion (Suzuki et al, 2013 Cancer Sci. 104, 896-903), the compound can be tested for its ability to inhibit phosphorylation of the RET substrate Src homology domain (Shc) (Hayashi et al, 2000 Oncogene. 19, 4469-4475), and downstream signaling through extracellular signal regulated kinase (ERK)1/2, including downregulation of dual specificity phosphatase 6 (DUSP6) and sprouty receptor tyrosine kinase signaling antagonist 4 (SPRY4) (Lito et al, 2013 Nat. Med. 19, 1401-1409). For instance, immunoblot can be performed for LC2/ad cells expressing the CCDC6-RET fusion protein and treated with the test compound at different concentrations; phosphorylated and total levels of downstream biomarkers, e.g., phospho(Y239/Y240)-Shc and phospho(Y202/T204)-ERK1/2, are measured. In addition, to determine expression levels of downstream targets, LC2/ad cells can be treated with the compound, cabozantinib, or DMSO for 7 hours and RNA is harvested. Gene expression levels of DUSP6 and SPRY4 can be measured by qRT-PCR. In some embodiments, the compound induces a dose-dependent decrease in expression of the ERK1/2 target genes DUSP6 and SPRY4 but not the control gene glycogen synthase kinase 3 beta (GSK3B).

3. Animal Models

Antitumor efficacy of compounds of structural Formula (I), (Ia), (Ib), (II), or (III) can be demonstrated in several RET-driven in vivo models. The Ba/F3-KIF5B-RET allograft model uses KIF5B RET fusion-dependent Ba/F3 cells. The test compound can be administered orally with an appropriate dose. Tumor size can be measured e.g., twice weekly. In some embodiments, administration of the compound results in robust and dose-dependent growth inhibition of Ba/F3-KIF5B-RET allograft tumors, e.g., in complete TGI and Mouse body weight can be measured e.g., twice-weekly during the administration. In some embodiments, the compound is well tolerated with no significant changes in animal body weight observed.

Similar assays can be performed using other animal models, including a Ba/F3-KIF5B-RET (V804L) allograft tumor model which comprises a KIF5B RET V804L fusion protein, an KIF5B-RET NSCLC allograft tumor model, an MTC cell line xenograft driven by a RET C634W mutation, and a CCDC6-RET fusion positive colorectal cancer allograft tumor model. The RET V804L mutation has been observed in rare cases of MTC and is predicted to be insensitive to cabozantinib and vandetanib in vitro and in vivo (Carlomagno et al, 2004 Biochem. Biophys. Res. Commun. 207, 1022-1028; Bentzien et al, 2013 Thyroid. 23, 1569-1577). In some embodiments, the compound causes complete TGI and regressions in a cancer that is not responsive to cabozantinib or vandetanib.

Biochemical markers can also be assayed in the treated mice. To assess direct inhibition of KIF5B-RET (V804L) fusion kinase activity in Ba/F3 KIF5B-RET (V804L) tumors, the compound can be administered orally at an appropriate dose to tumor bearing mice for several days and plasma and tumors can be collected from individual mice at appropriate time points after the last dose. Test compound concentrations in plasma can be determined by liquid chromatograph/tandem mass spectrometry (LC/MS/MS). Inhibition of KIF5B-RET (V804L) signaling in the tumor tissue can be assessed by a phosphor RET enzyme linked immunosorbent assay (ELISA) and by immunoblotting, e.g., as described above. Quantitation of the phospho-RET signal by ELISA can measure the percent KIF5B-RET (V804L) inhibition in treated animals as compared to vehicle treated controls. Suppression of downstream RET pathway signaling can be demonstrated by inhibition of Shc phosphorylation. In some embodiments, a dose and time-dependent correlation is observed between the concentration of the test compound in mouse plasma and the level of phosphorylated KIF5B RET (V804L). In some embodiments, administration of the compound at an amount sufficient to reach at least 90% inhibition of RET in vivo leads to therapeutic efficacy, e.g., can lead to 100% tumor growth inhibition.

Example 10: Selectivity of Compounds of Structural Formulas (I), (Ia), (Ib), (II), and (III)

Efficacy Against Wild-Type and Mutant RET

In some embodiments, compounds according to structural Formula (I), (Ia), (Ib), (II), and (III) are potent inhibitors of wild-type and mutant RET. For instance the $IC_{50}$ of a compound can be tested in a cell line comprising wild-type RET and in a second cell line comprising mutant RET, e.g., a point mutation or fusion.

Selectivity for RET Over KDR

In some embodiments, compounds according to structural Formula (I), (Ia), (Ib), (II), and (III) are selective for RET over another kinase, such as KDR (also called Vascular endothelial growth factor receptor 2). KDR is a tyrosine-protein kinase that acts as a cell-surface receptor for VEGFA, VEGFC and VEGFD. Inhibition of KDR/VEGFR2 has been associated clinically with certain adverse effects, e.g., hypertension, arterial thrombosis, and hemorrhage, and therefore selectivity for RET over KDR is desirable.

To test selectivity, the test compound can be assayed for its ability to inhibit proliferation in parental Ba/F3 cells that do not express a RET mutation, e.g., does not express a KIF5B-RET fusion. A weak $IC_{50}$ in the parental cell line indicates that the test compound is selective for cell lines dependent on oncogenic RET.

The selectivity of a compound on RET versus other human kinases can be characterized by profiling binding across a panel of over 450 human kinases and disease-relevant kinase mutants. In some embodiments, the compound has a high degree of selectivity for RET and RET kinase mutants over other kinases tested. To define the binding affinity for the kinases bound by the compound in kinome screening and additional kinases of interest, the dissociation constant (Kd) can be determined.

To differentiate the compound from multi-kinase inhibitors with biochemical activity against RET, the activity of the compound against recombinant kinase insert domain receptor (KDR) (also known as vascular endothelial growth factor receptor 2 [VEGFR2]) and fibroblast growth factor receptor 1 (FGFR1) can be tested, as inhibition of these kinases is associated with dose-limiting toxicities in humans. Inhibition of KDR/VEGFR2 has been associated clinically with hypertension, arterial thrombosis, and hemorrhage, whereas inhibition of fibroblast growth factor receptors (FGFRs) is associated with hyperphosphatemia and tissue calcification (Abdel-Rahman and Fouad, 2014 Crit. Rev. Oncol. Hematol. 92, 194-207; Touat et al, 2015 Clin. Cancer Res. 21, 2684-2694). In some embodiments, the compound is a more potent inhibitor of WT RET than KDR/VEGFR2 and FGFR1, respectively. In contrast, in some embodiments a multi-kinase inhibitor exhibits approximately equal or increased potency on KDR versus WT RET.

Example 11: Selective Compounds Prevent RET Resistance Mutants

The compounds herein can be tested for the propensity of a cancer to develop one or more RET mutations associated with drug resistance. For example, RET-altered cancer cells (e.g., Ba/F3 KIF5B-RET cells) can be treated with a mutagen such as ENU, exposed to a compound herein or a control compound (e.g., for 2-3 weeks), and the cell number can be quantified. Cells with high proliferation can be subjected to DNA sequencing to detect RET mutations. In some embodiments, a compound of structural Formula (I), (Ia), (Ib), (II), or (III) leads to no or fewer RET mutations than a control compound such as a multi-kinase inhibitor such as cabozantinib.

INCORPORATION BY REFERENCE

All publications and patents mentioned herein are hereby incorporated by reference in their entirety as if each individual publication or patent was specifically and individually indicated to be incorporated by reference.

EQUIVALENTS

Those skilled in the art will recognize, or be able to ascertain using no more than routine experimentation, many equivalents to the specific embodiments of the disclosure described herein. Such equivalents are intended to be encompassed by the following claims.

---

The invention claimed is:

1. A compound having the structural formula (I):

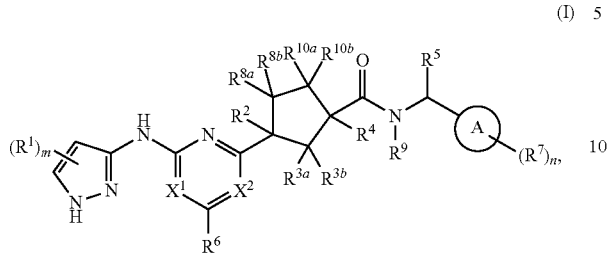

or a stereoisomer thereof, or a pharmaceutically acceptable salt of either of the foregoing, wherein:

ring A is an aryl or heteroaryl ring;

each of $X^1$ and $X^2$ is independently selected from N and $C(R^{6'})$;

each $R^1$ and each $R^7$ is independently selected from $C_1$-$C_6$ alkyl, $C_2$-$C_6$ alkenyl, $C_2$-$C_6$ alkynyl, $C_1$-$C_6$ alkoxy, halo, $C_1$-$C_6$ heteroalkyl, cycloalkyl, aryl, heteroaryl, aryloxy, aralkyl, heterocyclyl, heterocyclylalkyl, nitro, cyano, —C(O)$R^c$, —OC(O)$R^c$, —C(O)O$R^d$, —($C_1$-$C_6$ alkylene)-C(O)$R^c$, —S$R^d$, —S(O)$_2$$R^c$, —S(O)$_2$—N($R^d$)($R^d$), —($C_1$-$C_6$ alkylene)-S(O)$_2$$R^c$, —($C_1$-$C_6$ alkylene)-S(O)$_2$—N($R^d$)($R^d$), —N($R^d$)($R^d$), —C(O)—N($R^d$)($R^d$), —N($R^d$)—C(O)$R^c$, —N($R^d$)—C(O)O$R^c$, —($C_1$-$C_6$ alkylene)-N($R^d$)—C(O)$R^c$, —N($R^d$)S(O)$_2$$R^c$, and —P(O)($R^c$)($R^c$), wherein each of alkyl, alkenyl, alkynyl, alkoxy, heteroalkyl, cycloalkyl, aryl, heteroaryl, aryloxy, aralkyl, heterocyclyl, and heterocyclylalkyl is independently substituted with 0-5 occurrences of $R^a$, or two $R^1$ or two $R^7$ are taken together with the carbon atoms to which they are attached form a cycloalkyl or heterocyclyl ring independently substituted with 0-5 occurrences of $R^b$;

each of $R^2$, $R^{3a}$, $R^{3b}$, $R^4$, $R^{8a}$, $R^{8b}$, $R^{10a}$, and $R^{10b}$ is independently selected from hydrogen, $C_1$-$C_6$ alkyl, $C_1$-$C_6$ alkoxy, halo, hydroxyl, cyano, $C_1$-$C_6$ heteroalkyl, and —N($R^d$)($R^d$), wherein each of alkyl, alkoxy, and heteroalkyl is independently substituted with 0-5 occurrences of $R^a$;

each of $R^5$ and $R^9$ is independently selected from hydrogen, $C_1$-$C_6$ alkyl, and $C_1$-$C_6$ heteroalkyl, wherein each of alkyl and heteroalkyl is independently substituted with 0-5 occurrences of $R^a$;

$R^6$ and each $R^{6'}$ is independently selected from hydrogen, $C_1$-$C_6$ alkyl, $C_1$-$C_6$ alkoxy, halo, cyano, $C_1$-$C_6$ heteroalkyl, and —N($R^d$)($R^d$), wherein each alkyl, alkoxy, and heteroalkyl is independently substituted with 0-5 occurrences of $R^a$;

each $R^a$ and each $R^b$ is independently selected from $C_1$-$C_6$ alkyl, halo, hydroxyl, $C_1$-$C_6$ heteroalkyl, $C_1$-$C_6$ alkoxy, cycloalkyl, heterocyclyl, and cyano, wherein each of alkyl, heteroalkyl, alkoxy, cycloalkyl, and heterocyclyl is independently substituted with 0-5 occurrences of R';

each R' is independently selected from $C_1$-$C_6$ alkyl, $C_1$-$C_6$ heteroalkyl, halo, hydroxyl, cycloalkyl, and cyano, or two R' together with the atom(s) to which they are attached form a cycloalkyl or heterocyclyl ring;

each $R^c$ is independently selected from hydrogen, hydroxyl, halo, thiol, $C_1$-$C_6$ alkyl, $C_1$-$C_6$ thioalkyl, $C_1$-$C_6$ alkoxy, $C_1$-$C_6$ heteroalkyl, cycloalkyl, cycloalkylalkyl, heteroarylalkyl, heterocyclyl, and heterocyclylalkyl, wherein each of alkyl, thioalkyl, alkoxy, heteroalkyl, cycloalkyl, cycloalkylalkyl, heteroarylalkyl, heterocyclyl, and heterocyclylalkyl is independently substituted with 0-5 occurrences of $R^a$, or two $R^c$ together with the atom(s) to which they are attached form a cycloalkyl or heterocyclyl ring independently substituted with 0-5 occurrences of $R^b$;

each $R^d$ is independently selected from hydrogen, $C_1$-$C_6$ alkyl, $C_1$-$C_6$ heteroalkyl, cycloalkyl, cycloalkylalkyl, heteroarylalkyl, heterocyclyl, and heterocyclylalkyl, wherein each of alkyl, heteroalkyl, cycloalkyl, cycloalkylalkyl, heteroarylalkyl, heterocyclyl, and heterocyclylalkyl is independently substituted with 0-5 occurrences of $R^a$, or two $R^d$ together with the atom(s) to which they are attached form a cycloalkyl or heterocyclyl ring independently substituted with 0-5 occurrences of $R^b$;

m is 0, 1, or 2; and n is 0, 1, 2, or 3.

2. The compound of claim 1 having the structural formula (Ia):

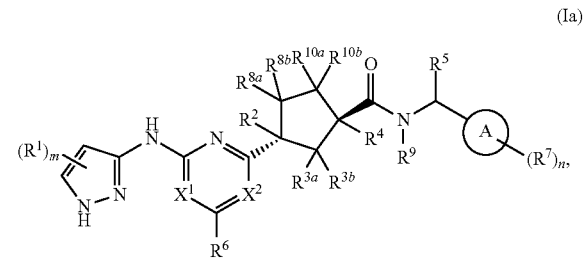

or structural formula (Ib):

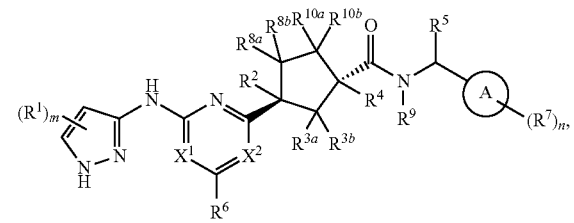

or a stereoisomer thereof, or a pharmaceutically acceptable salt of either of the foregoing, wherein ring A, $X^1$, $X^2$, $R^1$, $R^2$, $R^{3a}$, $R^{3b}$, $R^4$, $R^5$, $R^6$, $R^7$, $R^{8a}$, $R^{8b}$, $R^9$, $R^{10a}$, $R^{10b}$, m, and n are as defined in claim 1.

3. The compound of claim 1, or a stereoisomer thereof, or a pharmaceutically acceptable salt of either of the foregoing, wherein:

m is 1;

$R^1$ is located at the 5-position; and $R^1$ is $C_1$-$C_4$ alkyl or $C_3$-$C_6$ cycloalkyl, wherein $R^1$ is substituted with 0-3 occurrences of $R^a$.

4. The compound of claim 1, or a stereoisomer thereof, or a pharmaceutically acceptable salt of either of the foregoing, wherein:

$R^1$ is $CH_3$ or cyclopropyl;

$R^2$ is hydrogen or hydroxyl;

each of $R^{3a}$, $R^{3b}$, $R^{8a}$, $R^{8b}$, $R^{10a}$, and $R^{10b}$ is hydrogen;

$R^4$ is hydrogen or $C_1$-$C_4$ alkyl substituted with 0-3 occurrences of $R^a$;

R[5] is hydrogen or $C_1$-$C_4$ alkyl substituted with 0-3 occurrences of R[a]; or R[6] is $C_1$-$C_4$ alkyl substituted with 0-3 occurrences of R[a].

5. The compound of claim 1, or a stereoisomer thereof, or a pharmaceutically acceptable salt of either of the foregoing, wherein:
R[4] is hydrogen or $CH_3$;
R[5] is hydrogen or $CH_3$;
R[6] is $CH_3$;
each R[6'] is hydrogen; or
R[9] is hydrogen.

6. The compound of claim 1, or a stereoisomer thereof, or a pharmaceutically acceptable salt of either of the foregoing, wherein ring A is a 6-membered monocyclic heteroaryl comprising at least one nitrogen ring atom or phenyl.

7. The compound of claim 6, or a stereoisomer thereof, or a pharmaceutically acceptable salt of either of the foregoing, wherein ring A is selected from:

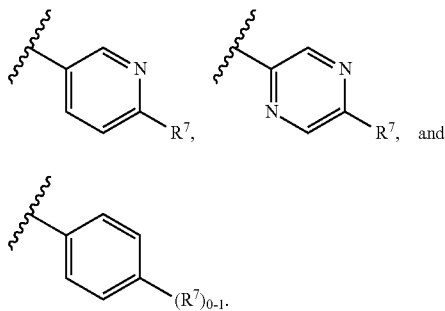

8. The compound of claim 1, or a stereoisomer thereof, or a pharmaceutically acceptable salt of either of the foregoing, wherein:
n is 0 or 1; and
R[7] is selected from pyrazol-1-yl substituted with 0-3 occurrences of R[a] and $C_1$-$C_4$ alkoxy substituted with 0-3 occurrences of R[a].

9. The compound of claim 8, or a stereoisomer thereof, or a pharmaceutically acceptable salt of either of the foregoing, wherein:
n is 0; or
n is 1 and R[7] is selected from 4-fluoropyrazol-1-yl, 4-chloropyrazol-1-yl, 3,5-dimethylpyrazol-1-yl, pyrazol-1-yl, and ethoxy.

10. The compound of claim 1, or a stereoisomer thereof, or a pharmaceutically acceptable salt of either of the foregoing, wherein:
X[1] is C(R[6']) and X[2] is N; or
X[1] is C(R[6']) and X[2] is C(R[6']).

11. A compound having the structural formula (II):

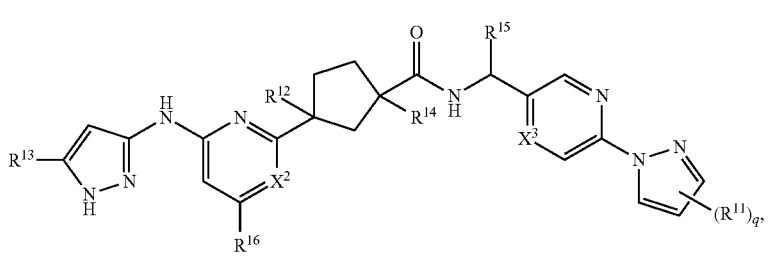

(II)

or a stereoisomer thereof, or a pharmaceutically acceptable salt of either of the foregoing, wherein:
X[2] is selected from N and CH;
X[3] is selected from N and CH;
each R[11] is independently selected from halo and $C_1$-$C_4$ alkyl substituted with 0-3 occurrences of R[a];
R[12] is hydrogen or hydroxyl;
R[13] is selected from $C_1$-$C_4$ alkyl and $C_3$-$C_6$ cycloalkyl, wherein R[13] is substituted with 0-3 occurrences of R[a];
R[14] is selected from hydrogen and $C_1$-$C_4$ alkyl substituted with 0-3 occurrences of R[a];
R[15] is selected from hydrogen and $C_1$-$C_4$ alkyl substituted with 0-3 occurrences of R[a];
R[16] is selected from hydrogen and $C_1$-$C_4$ alkyl substituted with 0-3 occurrences of R[a];
q is 0, 1, or 2;
each R[a] is independently selected from $C_1$-$C_6$ alkyl, halo, hydroxyl, $C_1$-$C_6$ heteroalkyl, $C_1$-$C_6$ alkoxy, cycloalkyl, heterocyclyl, and cyano, wherein each of alkyl, heteroalkyl, alkoxy, cycloalkyl, and heterocyclyl is independently substituted with 0-5 occurrences of R'; and
each R' is independently selected from $C_1$-$C_6$ alkyl, $C_1$-$C_6$ heteroalkyl, halo, hydroxyl, cycloalkyl, and cyano, or two R' together with the atom(s) to which they are attached form a cycloalkyl or heterocyclyl ring.

12. The compound of claim 11, or a stereoisomer thereof, or a pharmaceutically acceptable salt of either of the foregoing, wherein:
each R[11] is independently selected from fluoro and $CH_3$;
R[13] is selected from $CH_3$ and cyclopropyl;
R[14] is selected from hydrogen and $CH_3$;
R[15] is selected from hydrogen and $CH_3$; and
R[16] is $CH_3$.

13. A compound having the structural formula (III):

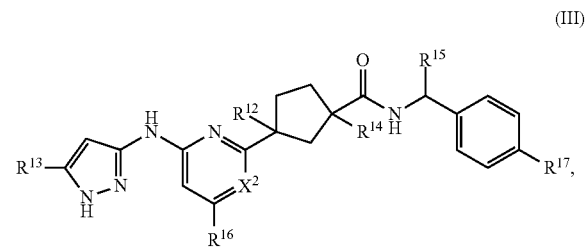

(III)

or a stereoisomer thereof, or a pharmaceutically acceptable salt of either of the foregoing, wherein:
X[2] is selected from N and CH;
R[12] is hydrogen or hydroxyl;

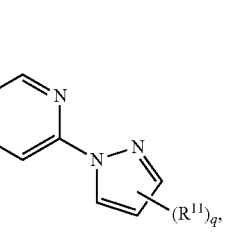

R¹³ is selected from $C_1$-$C_4$ alkyl or $C_3$-$C_6$ cycloalkyl, wherein R¹³ is substituted with 0-3 occurrences of $R^a$;

R¹⁴ is selected from hydrogen and $C_1$-$C_4$ alkyl substituted with 0-3 occurrences of $R^a$;

R¹⁵ is selected from hydrogen and $C_1$-$C_4$ alkyl substituted with 0-3 occurrences of $R^a$;

R¹⁶ is selected from hydrogen and $C_1$-$C_4$ alkyl substituted with 0-3 occurrences of $R^a$;

R¹⁷ is selected from hydrogen, $C_1$-$C_4$ alkyl substituted with 0-3 occurrences of $R^a$, and O—$C_1$-$C_4$ alkyl substituted with 0-3 occurrences of $R^a$;

each $R^a$ is independently selected from $C_1$-$C_6$ alkyl, halo, hydroxyl, $C_1$-$C_6$ heteroalkyl, $C_1$-$C_6$ alkoxy, cycloalkyl, heterocyclyl, and cyano, wherein each of alkyl, heteroalkyl, alkoxy, cycloalkyl, and heterocyclyl is independently substituted with 0-5 occurrences of R'; and each R' is independently selected from $C_1$-$C_6$ alkyl, $C_1$-$C_6$ heteroalkyl, halo, hydroxyl, cycloalkyl, and cyano, or two R' together with the atom(s) to which they are attached form a cycloalkyl or heterocyclyl ring.

14. The compound of claim 13, or a stereoisomer thereof, or a pharmaceutically acceptable salt of either of the foregoing, wherein:

R¹³ is selected from $CH_3$ and cyclopropyl;

R¹⁴ is selected from hydrogen and $CH_3$;

R¹⁵ is selected from hydrogen and $CH_3$;

R¹⁶ is $CH_3$; and

R¹⁷ is selected from hydrogen and $OCH_3$.

15. A pharmaceutical composition comprising:
a compound of claim 1, or a stereoisomer thereof, or a pharmaceutically acceptable salt of either of the foregoing; and
a pharmaceutically acceptable carrier.

16. A method for treating a subject suffering from non-small cell lung cancer, the method comprising administering to the subject a therapeutically effective amount of a compound of claim 1, or a stereoisomer thereof, or a pharmaceutically acceptable salt of either of the foregoing.

17. A method for treating a subject suffering from papillary thyroid cancer, the method comprising administering to the subject a therapeutically effective amount of a compound of claim 1, or a stereoisomer thereof, or a pharmaceutically acceptable salt of either of the foregoing.

18. A method for treating a subject suffering from medullary thyroid cancer, the method comprising administering to the subject a therapeutically effective amount of a compound of claim 1, or a stereoisomer thereof, or a pharmaceutically acceptable salt of either of the foregoing.

19. A method for treating a subject suffering from colorectal cancer, the method comprising administering to the subject a therapeutically effective amount of a compound of claim 1, or a stereoisomer thereof, or a pharmaceutically acceptable salt of either of the foregoing.

20. A method for treating a subject suffering from multiple endocrine neoplasia, the method comprising administering to the subject a therapeutically effective amount of a compound of claim 1, or a stereoisomer thereof, or a pharmaceutically acceptable salt of either of the foregoing.

21. A compound selected from:

| Compound # | Structure |
|---|---|
| 100 | 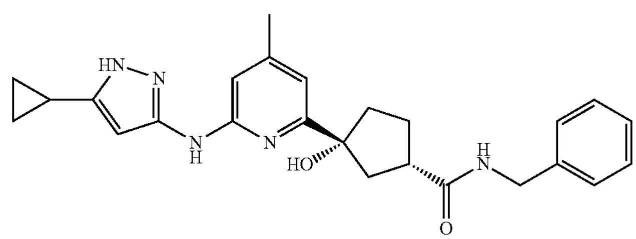 [SMILES: Cc1cc(Nc2cc(C3CC3)[nH]n2)nc([C@@]2(O)CC[C@H](C(=O)NCc3ccccc3)C2)c1] |
| 101 | 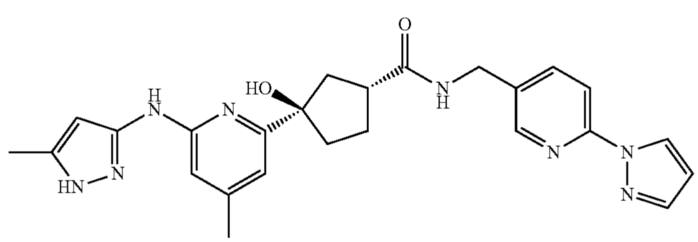 [SMILES: Cc1cc(Nc2cc(C)[nH]n2)nc([C@@]2(O)CC[C@@H](C(=O)NCc3ccc(-n4cccn4)nc3)C2)c1] |
| 102 | 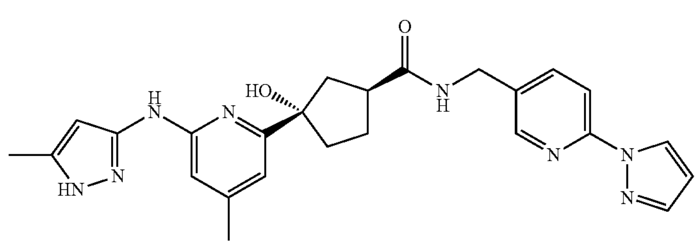 [SMILES: Cc1cc(Nc2cc(C)[nH]n2)nc([C@]2(O)CC[C@H](C(=O)NCc3ccc(-n4cccn4)nc3)C2)c1] |

-continued
| Compound # | Structure |
|---|---|
| 103 | 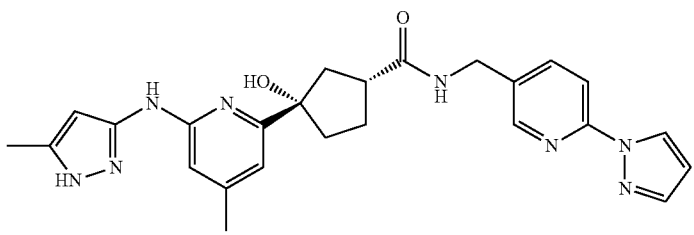 [SMILES: Cc1cc(Nc2cc(C)[nH]n2)nc([C@]2(O)CC[C@@H](C(=O)NCc3ccc(-n4cccn4)nc3)C2)c1] |
| 104 | 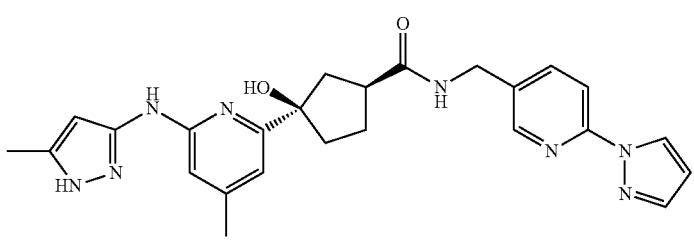 [SMILES: Cc1cc(Nc2cc(C)[nH]n2)nc([C@@]2(O)CC[C@H](C(=O)NCc3ccc(-n4cccn4)nc3)C2)c1] |
| 105 | 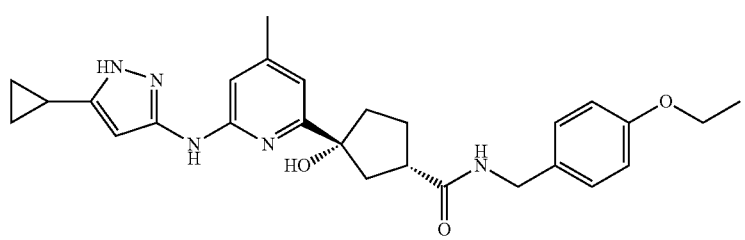 [SMILES: CCOc1ccc(CNC(=O)[C@H]2CC[C@](O)(c3cc(C)cc(Nc4cc(C5CC5)[nH]n4)n3)C2)cc1] |
| 106 | 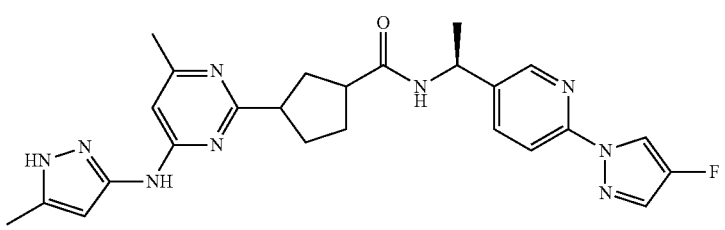 [SMILES: Cc1cc(Nc2cc(C)[nH]n2)nc(C2CCC(C(=O)N[C@@H](C)c3ccc(-n4cc(F)cn4)nc3)C2)n1] |
| 107 | 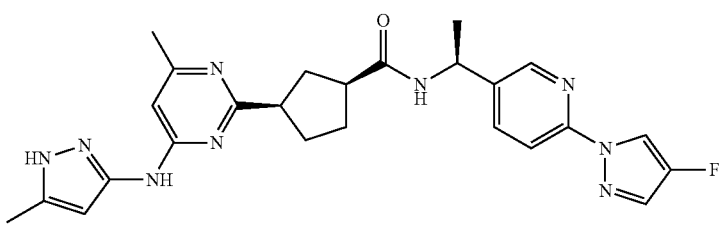 [SMILES: Cc1cc(Nc2cc(C)[nH]n2)nc([C@@H]2CC[C@H](C(=O)N[C@@H](C)c3ccc(-n4cc(F)cn4)nc3)C2)n1] |
| 108 | 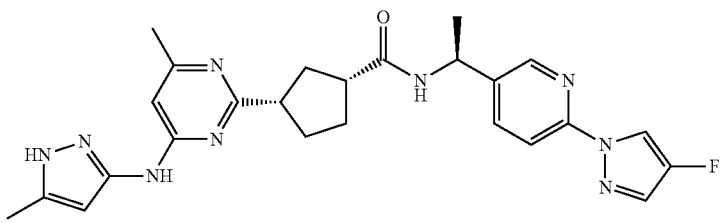 [SMILES: Cc1cc(Nc2cc(C)[nH]n2)nc([C@H]2CC[C@@H](C(=O)N[C@@H](C)c3ccc(-n4cc(F)cn4)nc3)C2)n1] |

-continued
| Compound # | Structure |
|---|---|
| 109 | 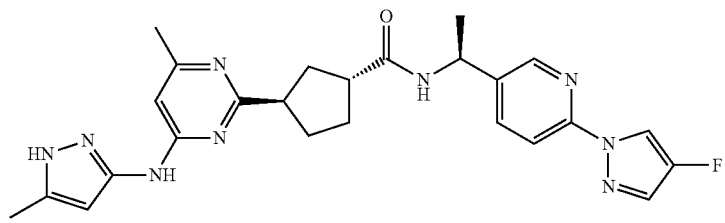 [SMILES: Cc1cc(Nc2cc(C)[nH]n2)nc([C@@H]2CC[C@@H](C(=O)N[C@@H](C)c3ccc(-n4cc(F)cn4)nc3)C2)n1] |
| 110 | 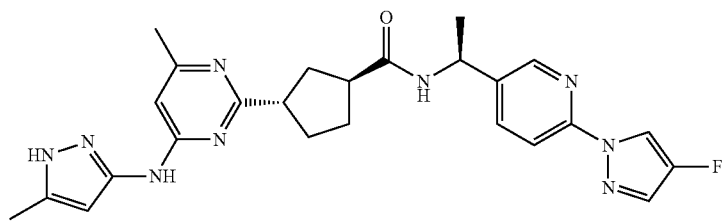 [SMILES: Cc1cc(Nc2cc(C)[nH]n2)nc([C@H]2CC[C@H](C(=O)N[C@@H](C)c3ccc(-n4cc(F)cn4)nc3)C2)n1] |
| 111 | 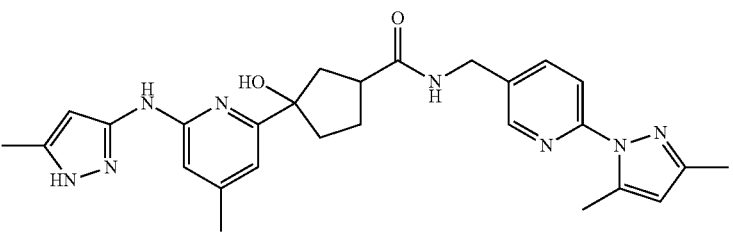 |
| 112 | 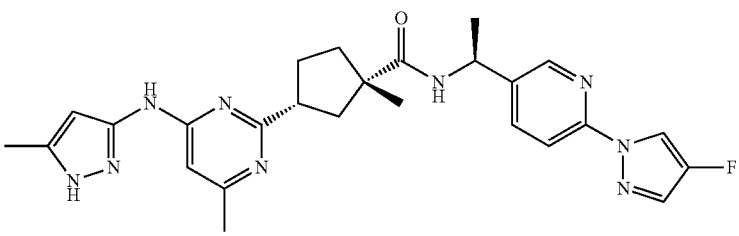 |
| 113 | 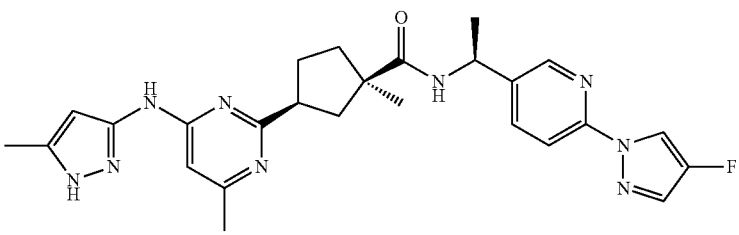 [SMILES: Cc1cc(Nc2cc(C)[nH]n2)nc([C@H]2CC[C@@](C)(C(=O)N[C@@H](C)c3ccc(-n4cc(F)cn4)nc3)C2)n1] |
| 114 | 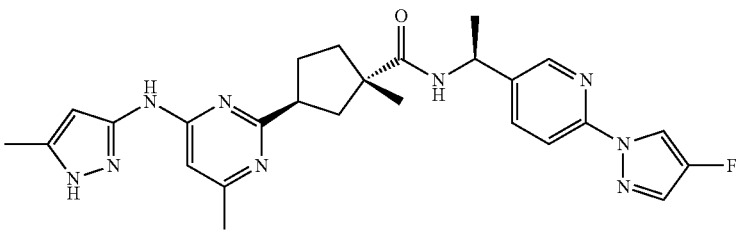 [SMILES: Cc1cc(Nc2cc(C)[nH]n2)nc([C@H]2CC[C@](C)(C(=O)N[C@@H](C)c3ccc(-n4cc(F)cn4)nc3)C2)n1] |

-continued

| Compound # | Structure |
|---|---|
| 115 | 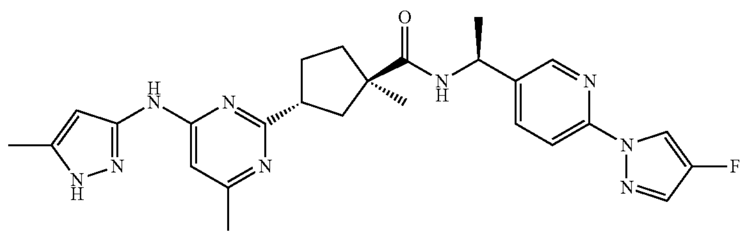 [SMILES: Cc1cc(Nc2cc(C)[nH]n2)nc([C@@H]2CC[C@@](C)(C(=O)N[C@@H](C)c3ccc(-n4cc(F)cn4)nc3)C2)n1] |
| 116 | 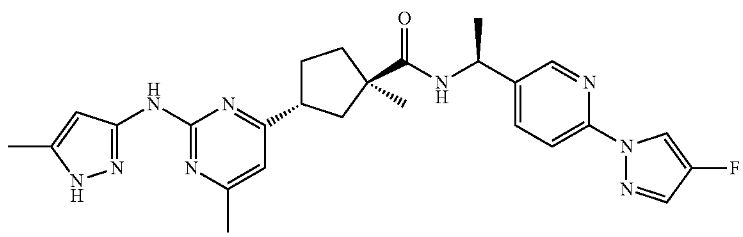 [SMILES: Cc1cc([C@@H]2CC[C@@](C)(C(=O)N[C@@H](C)c3ccc(-n4cc(F)cn4)nc3)C2)nc(Nc2cc(C)[nH]n2)n1] |
| 117 | 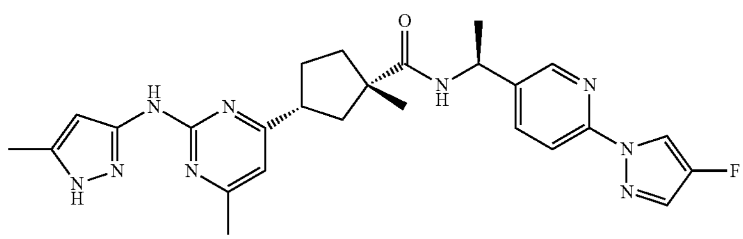 [SMILES: Cc1cc([C@@H]2CC[C@](C)(C(=O)N[C@@H](C)c3ccc(-n4cc(F)cn4)nc3)C2)nc(Nc2cc(C)[nH]n2)n1] |
| 118 | 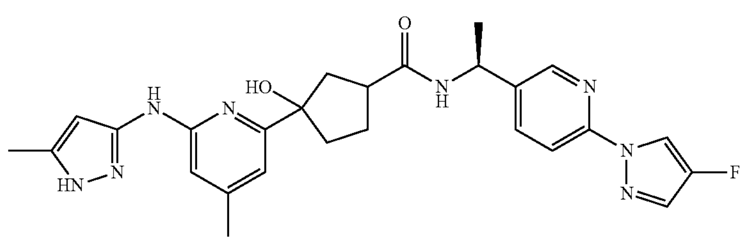 |
| 119 | 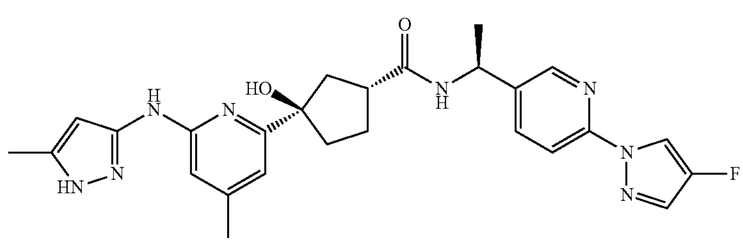 [SMILES: Cc1cc(Nc2cc(C)[nH]n2)nc([C@@]2(O)CC[C@@H](C(=O)N[C@@H](C)c3ccc(-n4cc(F)cn4)nc3)C2)c1] |
| 120 | 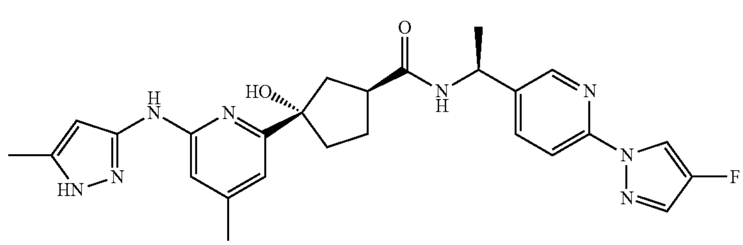 [SMILES: Cc1cc(Nc2cc(C)[nH]n2)nc([C@]2(O)CC[C@H](C(=O)N[C@@H](C)c3ccc(-n4cc(F)cn4)nc3)C2)c1] |

| Compound # | Structure |
|---|---|
| 121 | 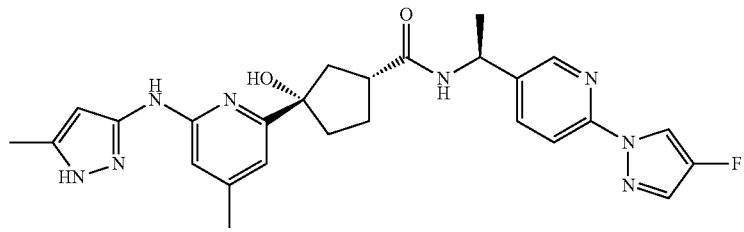 |
| 122 | 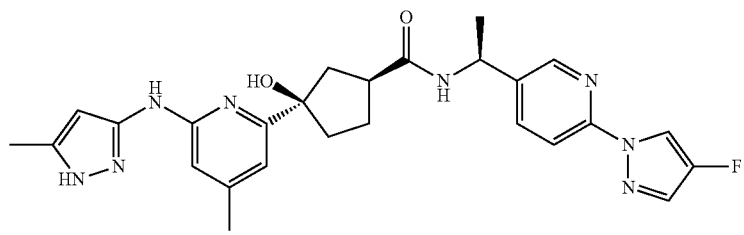 [SMILES: Cc1cc(Nc2cc(C)[nH]n2)nc([C@@]2(O)CC[C@H](C(=O)N[C@@H](C)c3ccc(-n4cc(F)cn4)nc3)C2)c1] |
| 123 | 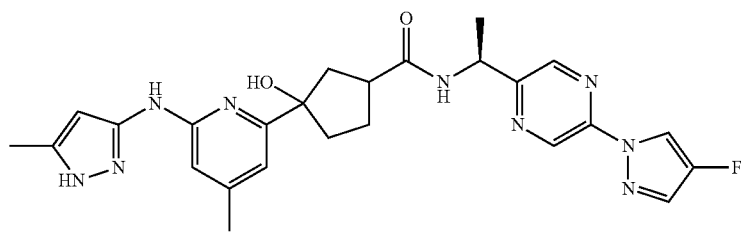 |
| 124 | 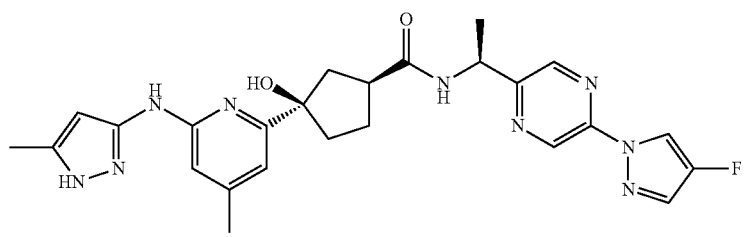 [SMILES: Cc1cc(Nc2cc(C)[nH]n2)nc([C@@]2(O)CC[C@H](C(=O)N[C@@H](C)c3cnc(-n4cc(F)cn4)cn3)C2)c1] |
| 125 | 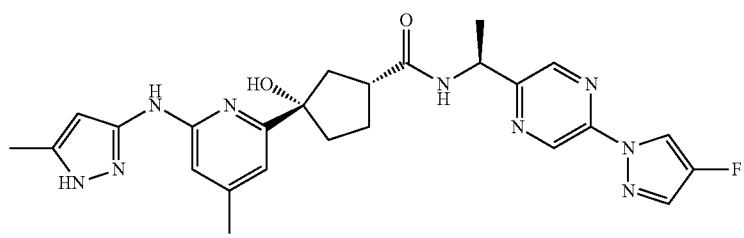 [SMILES: Cc1cc(Nc2cc(C)[nH]n2)nc([C@]2(O)CC[C@@H](C(=O)N[C@@H](C)c3cnc(-n4cc(F)cn4)cn3)C2)c1] |
| 126 | 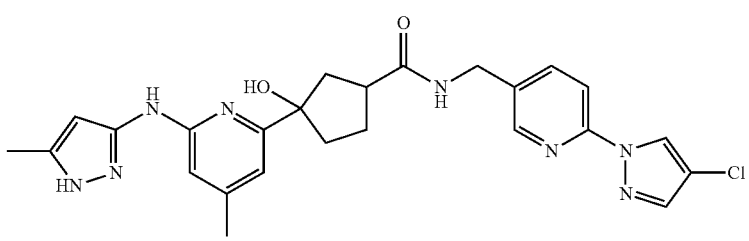 [SMILES: Cc1cc(Nc2cc(C)[nH]n2)nc(C2(O)CCC(C(=O)NCc3ccc(-n4cc(Cl)cn4)nc3)C2)c1] |

| Compound # | Structure |
|---|---|
| 127 | 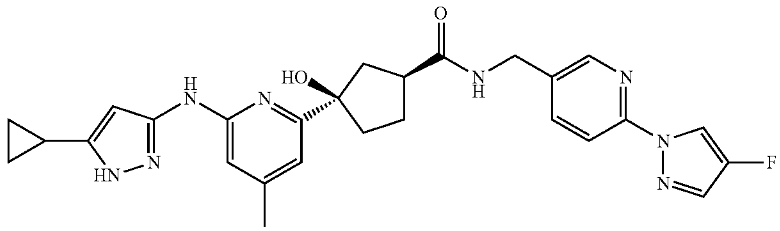 [SMILES: Cc1cc(Nc2cc(C3CC3)[nH]n2)nc([C@@]2(O)CC[C@H](C(=O)NCc3ccc(-n4cc(F)cn4)nc3)C2)c1] |
| 128 | 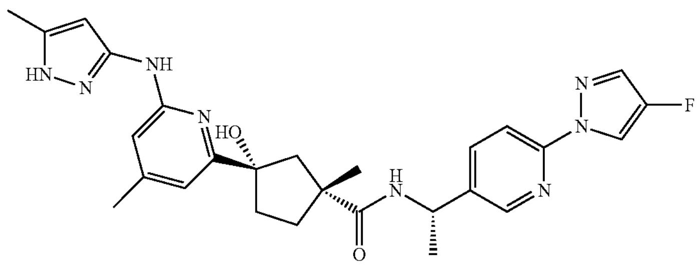 [SMILES: Cc1cc(Nc2cc(C)[nH]n2)nc([C@]2(O)CC[C@@](C)(C(=O)N[C@@H](C)c3ccc(-n4cc(F)cn4)nc3)C2)c1] |
| 129 | | and pharmaceutically acceptable salts thereof.

* * * * *

SEQUENCE LISTING

```
<160> NUMBER OF SEQ ID NOS: 5

<210> SEQ ID NO 1
<211> LENGTH: 1114
<212> TYPE: PRT
<213> ORGANISM: Homo sapiens

<400> SEQUENCE: 1

Met Ala Lys Ala Thr Ser Gly Ala Ala Gly Leu Arg Leu Leu Leu Leu
1               5                   10                  15

Leu Leu Leu Pro Leu Leu Gly Lys Val Ala Leu Gly Leu Tyr Phe Ser
                20                  25                  30

Arg Asp Ala Tyr Trp Glu Lys Leu Tyr Val Asp Gln Ala Ala Gly Thr
            35                  40                  45

Pro Leu Leu Tyr Val His Ala Leu Arg Asp Ala Pro Glu Glu Val Pro
        50                  55                  60

Ser Phe Arg Leu Gly Gln His Leu Tyr Gly Thr Tyr Arg Thr Arg Leu
```

-continued

```
             65                  70                  75                  80
His Glu Asn Asn Trp Ile Cys Ile Gln Glu Asp Thr Gly Leu Leu Tyr
                    85                  90                  95

Leu Asn Arg Ser Leu Asp His Ser Ser Trp Glu Lys Leu Ser Val Arg
                100                 105                 110

Asn Arg Gly Phe Pro Leu Leu Thr Val Tyr Leu Lys Val Phe Leu Ser
                115                 120                 125

Pro Thr Ser Leu Arg Glu Gly Glu Cys Gln Trp Pro Gly Cys Ala Arg
            130                 135                 140

Val Tyr Phe Ser Phe Phe Asn Thr Ser Phe Pro Ala Cys Ser Ser Leu
145                 150                 155                 160

Lys Pro Arg Glu Leu Cys Phe Pro Glu Thr Arg Pro Ser Phe Arg Ile
                165                 170                 175

Arg Glu Asn Arg Pro Pro Gly Thr Phe His Gln Phe Arg Leu Leu Pro
                180                 185                 190

Val Gln Phe Leu Cys Pro Asn Ile Ser Val Ala Tyr Arg Leu Leu Glu
                195                 200                 205

Gly Glu Gly Leu Pro Phe Arg Cys Ala Pro Asp Ser Leu Glu Val Ser
            210                 215                 220

Thr Arg Trp Ala Leu Asp Arg Glu Gln Arg Glu Lys Tyr Glu Leu Val
225                 230                 235                 240

Ala Val Cys Thr Val His Ala Gly Ala Arg Glu Glu Val Val Met Val
                245                 250                 255

Pro Phe Pro Val Thr Val Tyr Asp Glu Asp Asp Ser Ala Pro Thr Phe
                260                 265                 270

Pro Ala Gly Val Asp Thr Ala Ser Ala Val Val Glu Phe Lys Arg Lys
            275                 280                 285

Glu Asp Thr Val Val Ala Thr Leu Arg Val Phe Asp Ala Asp Val Val
            290                 295                 300

Pro Ala Ser Gly Glu Leu Val Arg Arg Tyr Thr Ser Thr Leu Leu Pro
305                 310                 315                 320

Gly Asp Thr Trp Ala Gln Gln Thr Phe Arg Val Glu His Trp Pro Asn
                325                 330                 335

Glu Thr Ser Val Gln Ala Asn Gly Ser Phe Val Arg Ala Thr Val His
                340                 345                 350

Asp Tyr Arg Leu Val Leu Asn Arg Asn Leu Ser Ile Ser Glu Asn Arg
            355                 360                 365

Thr Met Gln Leu Ala Val Leu Val Asn Asp Ser Asp Phe Gln Gly Pro
            370                 375                 380

Gly Ala Gly Val Leu Leu Leu His Phe Asn Val Ser Val Leu Pro Val
385                 390                 395                 400

Ser Leu His Leu Pro Ser Thr Tyr Ser Leu Ser Val Ser Arg Arg Ala
                405                 410                 415

Arg Arg Phe Ala Gln Ile Gly Lys Val Cys Val Glu Asn Cys Gln Ala
                420                 425                 430

Phe Ser Gly Ile Asn Val Gln Tyr Lys Leu His Ser Ser Gly Ala Asn
                435                 440                 445

Cys Ser Thr Leu Gly Val Val Thr Ser Ala Glu Asp Thr Ser Gly Ile
            450                 455                 460

Leu Phe Val Asn Asp Thr Lys Ala Leu Arg Arg Pro Lys Cys Ala Glu
465                 470                 475                 480

Leu His Tyr Met Val Val Ala Thr Asp Gln Gln Thr Ser Arg Gln Ala
                485                 490                 495
```

```
Gln Ala Gln Leu Leu Val Thr Val Glu Gly Ser Tyr Val Ala Glu
            500                 505                 510
Glu Ala Gly Cys Pro Leu Ser Cys Ala Val Ser Lys Arg Leu Glu
            515                 520                 525
Cys Glu Glu Cys Gly Gly Leu Gly Ser Pro Thr Gly Arg Cys Glu
            530                 535                 540
Trp Arg Gln Gly Asp Gly Lys Gly Ile Thr Arg Asn Phe Ser Thr
545                 550                 555                 560
Cys Ser Pro Ser Thr Lys Thr Cys Pro Asp Gly His Cys Asp Val
                        565                 570
Val Glu Thr Gln Asp Ile Asn Ile Cys Pro Gln Asp Cys Leu Arg
            575                 580                 585
Gly Ser Ile Val Gly Gly His Glu Pro Gly Glu Pro Arg Gly Ile
            590                     595                 600
Lys Ala Gly Tyr Gly Thr Cys Asn Cys Phe Pro Glu Glu Lys Cys
            605                 610                 615
Phe Cys Glu Pro Glu Asp Ile Gln Asp Pro Leu Cys Asp Glu Leu
            620                 625                 630
Cys Arg Thr Val Ile Ala Ala Ala Val Leu Phe Ser Phe Ile Val
            635                 640                 645
Ser Val Leu Ser Ala Phe Cys Ile His Cys Tyr His Lys Phe Ala
            650                 655                 660
His Lys Pro Pro Ile Ser Ser Ala Glu Met Thr Phe Arg Arg Pro
            665                 670                 675
Ala Gln Ala Phe Pro Val Ser Tyr Ser Ser Ser Gly Ala Arg Arg
            680                 685                 690
Pro Ser Leu Asp Ser Met Glu Asn Gln Val Ser Val Asp Ala Phe
                695                 700                 705
Lys Ile Leu Glu Asp Pro Lys Trp Glu Phe Pro Arg Lys Asn Leu
            710                 715                 720
Val Leu Gly Lys Thr Leu Gly Glu Gly Glu Phe Gly Lys Val Val
            725                 730                 735
Lys Ala Thr Ala Phe His Leu Lys Gly Arg Ala Gly Tyr Thr Thr
            740                 745                 750
Val Ala Val Lys Met Leu Lys Glu Asn Ala Ser Pro Ser Glu Leu
            755                 760                 765
Arg Asp Leu Leu Ser Glu Phe Asn Val Leu Lys Gln Val Asn His
            770                 775                 780
Pro His Val Ile Lys Leu Tyr Gly Ala Cys Ser Gln Asp Gly Pro
785                 790                 795                 800
Leu Leu Leu Ile Val Glu Tyr Ala Lys Tyr Gly Ser Leu Arg Gly
                            805                 810
Phe Leu Arg Glu Ser Arg Lys Val Gly Pro Gly Tyr Leu Gly Ser
            815                 820                 825
Gly Ser Arg Asn Ser Ser Ser Leu Asp His Pro Asp Glu Arg Ala
            830                 835                 840
Leu Thr Met Gly Asp Leu Ile Ser Phe Ala Trp Gln Ile Ser Gln
            845                 850                 855
Gly Met Gln Tyr Leu Ala Glu Met Lys Leu Val His Arg Asp Leu
            860                 865                 870
Ala Ala Arg Asn Ile Leu Val Ala Glu Gly Arg Lys Met Lys Ile
            875                 880                     885
Ser Asp Phe Gly Leu Ser Arg Asp Val Tyr Glu Glu Asp Ser Tyr
                890                 895                 900
Val Lys Arg Ser Gln Gly Arg
            905                 910
```

```
Ile Pro Val Lys Trp Met Ala Ile Glu Ser Leu Phe Asp His Ile Tyr
        915                 920                 925

Thr Thr Gln Ser Asp Val Trp Ser Phe Gly Val Leu Leu Trp Glu Ile
    930                 935                 940

Val Thr Leu Gly Gly Asn Pro Tyr Pro Gly Ile Pro Pro Glu Arg Leu
945                 950                 955                 960

Phe Asn Leu Leu Lys Thr Gly His Arg Met Glu Arg Pro Asp Asn Cys
            965                 970                 975

Ser Glu Glu Met Tyr Arg Leu Met Leu Gln Cys Trp Lys Gln Glu Pro
            980                 985                 990

Asp Lys Arg Pro Val Phe Ala Asp Ile Ser Lys Asp Leu Glu Lys Met
            995                 1000                1005

Met Val Lys Arg Arg Asp Tyr Leu Asp Leu Ala Ala Ser Thr Pro
    1010                1015                1020

Ser Asp Ser Leu Ile Tyr Asp Asp Gly Leu Ser Glu Glu Thr
    1025                1030                1035

Pro Leu Val Asp Cys Asn Asn Ala Pro Leu Pro Arg Ala Leu Pro
    1040                1045                1050

Ser Thr Trp Ile Glu Asn Lys Leu Tyr Gly Met Ser Asp Pro Asn
    1055                1060                1065

Trp Pro Gly Glu Ser Pro Val Pro Leu Thr Arg Ala Asp Gly Thr
    1070                1075                1080

Asn Thr Gly Phe Pro Arg Tyr Pro Asn Asp Ser Val Tyr Ala Asn
    1085                1090                1095

Trp Met Leu Ser Pro Ser Ala Ala Lys Leu Met Asp Thr Phe Asp
    1100                1105                1110

Ser

<210> SEQ ID NO 2
<211> LENGTH: 1072
<212> TYPE: PRT
<213> ORGANISM: Homo sapiens

<400> SEQUENCE: 2

Met Ala Lys Ala Thr Ser Gly Ala Ala Gly Leu Arg Leu Leu Leu Leu
1               5                   10                  15

Leu Leu Leu Pro Leu Leu Gly Lys Val Ala Leu Gly Leu Tyr Phe Ser
            20                  25                  30

Arg Asp Ala Tyr Trp Glu Lys Leu Tyr Val Asp Gln Ala Ala Gly Thr
        35                  40                  45

Pro Leu Leu Tyr Val His Ala Leu Arg Asp Ala Pro Glu Glu Val Pro
    50                  55                  60

Ser Phe Arg Leu Gly Gln His Leu Tyr Gly Thr Tyr Arg Thr Arg Leu
65                  70                  75                  80

His Glu Asn Asn Trp Ile Cys Ile Gln Glu Asp Thr Gly Leu Leu Tyr
                85                  90                  95

Leu Asn Arg Ser Leu Asp His Ser Ser Trp Glu Lys Leu Ser Val Arg
            100                 105                 110

Asn Arg Gly Phe Pro Leu Leu Thr Val Tyr Leu Lys Val Phe Leu Ser
        115                 120                 125

Pro Thr Ser Leu Arg Glu Gly Glu Cys Gln Trp Pro Gly Cys Ala Arg
    130                 135                 140

Val Tyr Phe Ser Phe Phe Asn Thr Ser Phe Pro Ala Cys Ser Ser Leu
145                 150                 155                 160
```

-continued

Lys Pro Arg Glu Leu Cys Phe Pro Glu Thr Arg Pro Ser Phe Arg Ile
            165                 170                 175
Arg Glu Asn Arg Pro Pro Gly Thr Phe His Gln Phe Arg Leu Leu Pro
        180                 185                 190
Val Gln Phe Leu Cys Pro Asn Ile Ser Val Ala Tyr Arg Leu Leu Glu
    195                 200                 205
Gly Glu Gly Leu Pro Phe Arg Cys Ala Pro Asp Ser Leu Glu Val Ser
210                 215                 220
Thr Arg Trp Ala Leu Asp Arg Glu Gln Arg Lys Tyr Glu Leu Val
225                 230                 235                 240
Ala Val Cys Thr Val His Ala Gly Ala Arg Glu Glu Val Val Met Val
                245                 250                 255
Pro Phe Pro Val Thr Val Tyr Asp Glu Asp Ser Ala Pro Thr Phe
            260                 265                 270
Pro Ala Gly Val Asp Thr Ala Ser Ala Val Val Glu Phe Lys Arg Lys
        275                 280                 285
Glu Asp Thr Val Val Ala Thr Leu Arg Val Phe Asp Ala Asp Val Val
    290                 295                 300
Pro Ala Ser Gly Glu Leu Val Arg Arg Tyr Thr Ser Thr Leu Leu Pro
305                 310                 315                 320
Gly Asp Thr Trp Ala Gln Gln Thr Phe Arg Val Glu His Trp Pro Asn
                325                 330                 335
Glu Thr Ser Val Gln Ala Asn Gly Ser Phe Val Arg Ala Thr Val His
            340                 345                 350
Asp Tyr Arg Leu Val Leu Asn Arg Asn Leu Ser Ile Ser Glu Asn Arg
        355                 360                 365
Thr Met Gln Leu Ala Val Leu Val Asn Asp Ser Asp Phe Gln Gly Pro
    370                 375                 380
Gly Ala Gly Val Leu Leu Leu His Phe Asn Val Ser Val Leu Pro Val
385                 390                 395                 400
Ser Leu His Leu Pro Ser Thr Tyr Ser Leu Ser Val Ser Arg Arg Ala
                405                 410                 415
Arg Arg Phe Ala Gln Ile Gly Lys Val Cys Val Glu Asn Cys Gln Ala
            420                 425                 430
Phe Ser Gly Ile Asn Val Gln Tyr Lys Leu His Ser Ser Gly Ala Asn
        435                 440                 445
Cys Ser Thr Leu Gly Val Val Thr Ser Ala Glu Asp Thr Ser Gly Ile
    450                 455                 460
Leu Phe Val Asn Asp Thr Lys Ala Leu Arg Arg Pro Lys Cys Ala Glu
465                 470                 475                 480
Leu His Tyr Met Val Val Ala Thr Asp Gln Gln Thr Ser Arg Gln Ala
                485                 490                 495
Gln Ala Gln Leu Leu Val Thr Val Glu Gly Ser Tyr Val Ala Glu Glu
            500                 505                 510
Ala Gly Cys Pro Leu Ser Cys Ala Val Ser Lys Arg Arg Leu Glu Cys
        515                 520                 525
Glu Glu Cys Gly Gly Leu Gly Ser Pro Thr Gly Arg Cys Glu Trp Arg
    530                 535                 540
Gln Gly Asp Gly Lys Gly Ile Thr Arg Asn Phe Ser Thr Cys Ser Pro
545                 550                 555                 560
Ser Thr Lys Thr Cys Pro Asp Gly His Cys Asp Val Val Glu Thr Gln
                565                 570                 575
Asp Ile Asn Ile Cys Pro Gln Asp Cys Leu Arg Gly Ser Ile Val Gly

-continued

```
            580                 585                 590
Gly His Glu Pro Gly Glu Pro Arg Gly Ile Lys Ala Gly Tyr Gly Thr
            595                 600                 605
Cys Asn Cys Phe Pro Glu Glu Lys Cys Phe Cys Glu Pro Glu Asp
            610                 615                 620
Ile Gln Asp Pro Leu Cys Asp Glu Leu Cys Arg Thr Val Ile Ala Ala
625                         630                 635                 640
Ala Val Leu Phe Ser Phe Ile Val Ser Val Leu Ser Ala Phe Cys
                        645                 650                 655
Ile His Cys Tyr His Lys Phe Ala His Lys Pro Pro Ile Ser Ser Ala
                        660                 665                 670
Glu Met Thr Phe Arg Arg Pro Ala Gln Ala Phe Pro Val Ser Tyr Ser
                        675                 680                 685
Ser Ser Gly Ala Arg Arg Pro Ser Leu Asp Ser Met Glu Asn Gln Val
                        690                 695                 700
Ser Val Asp Ala Phe Lys Ile Leu Glu Asp Pro Lys Trp Glu Phe Pro
705                         710                 715                 720
Arg Lys Asn Leu Val Leu Gly Lys Thr Leu Gly Glu Gly Glu Phe Gly
                        725                 730                 735
Lys Val Val Lys Ala Thr Ala Phe His Leu Lys Gly Arg Ala Gly Tyr
                        740                 745                 750
Thr Thr Val Ala Val Lys Met Leu Lys Glu Asn Ala Ser Pro Ser Glu
                        755                 760                 765
Leu Arg Asp Leu Leu Ser Glu Phe Asn Val Leu Lys Gln Val Asn His
                        770                 775                 780
Pro His Val Ile Lys Leu Tyr Gly Ala Cys Ser Gln Asp Gly Pro Leu
785                         790                 795                 800
Leu Leu Ile Val Glu Tyr Ala Lys Tyr Gly Ser Leu Arg Gly Phe Leu
                        805                 810                 815
Arg Glu Ser Arg Lys Val Gly Pro Gly Tyr Leu Gly Ser Gly Gly Ser
                        820                 825                 830
Arg Asn Ser Ser Ser Leu Asp His Pro Asp Glu Arg Ala Leu Thr Met
                        835                 840                 845
Gly Asp Leu Ile Ser Phe Ala Trp Gln Ile Ser Gln Gly Met Gln Tyr
                        850                 855                 860
Leu Ala Glu Met Lys Leu Val His Arg Asp Leu Ala Ala Arg Asn Ile
865                         870                 875                 880
Leu Val Ala Glu Gly Arg Lys Met Lys Ile Ser Asp Phe Gly Leu Ser
                        885                 890                 895
Arg Asp Val Tyr Glu Glu Asp Ser Tyr Val Lys Arg Ser Gln Gly Arg
                        900                 905                 910
Ile Pro Val Lys Trp Met Ala Ile Glu Ser Leu Phe Asp His Ile Tyr
                        915                 920                 925
Thr Thr Gln Ser Asp Val Trp Ser Phe Gly Val Leu Leu Trp Glu Ile
                        930                 935                 940
Val Thr Leu Gly Gly Asn Pro Tyr Pro Gly Ile Pro Pro Glu Arg Leu
945                         950                 955                 960
Phe Asn Leu Leu Lys Thr Gly His Arg Met Glu Arg Pro Asp Asn Cys
                        965                 970                 975
Ser Glu Glu Met Tyr Arg Leu Met Leu Gln Cys Trp Lys Gln Glu Pro
                        980                 985                 990
Asp Lys Arg Pro Val Phe Ala Asp Ile Ser Lys Asp Leu Glu Lys Met
                        995                 1000                1005
```

```
Met Val Lys Arg Arg Asp Tyr Leu Asp Leu Ala Ala Ser Thr Pro
    1010                1015                1020

Ser Asp Ser Leu Ile Tyr Asp Asp Gly Leu Ser Glu Glu Thr
    1025                1030                1035

Pro Leu Val Asp Cys Asn Asn Ala Pro Leu Pro Arg Ala Leu Pro
    1040                1045                1050

Ser Thr Trp Ile Glu Asn Lys Leu Tyr Gly Arg Ile Ser His Ala
    1055                1060                1065

Phe Thr Arg Phe
    1070

<210> SEQ ID NO 3
<211> LENGTH: 5629
<212> TYPE: DNA
<213> ORGANISM: Homo sapiens

<400> SEQUENCE: 3
```

| | | | | | |
|---|---|---|---|---|---|
| agtcccgcga | ccgaagcagg | gcgcgcagca | gcgctgagtg | ccccggaacg | tgcgtcgcgc | 60 |
| ccccagtgtc | cgtcgcgtcc | gccgcgcccc | gggcggggat | ggggcggcca | gactgagcgc | 120 |
| cgcacccgcc | atccagaccc | gccggcccta | gccgcagtcc | ctccagccgt | ggccccagcg | 180 |
| cgcacgggcg | atggcgaagg | cgacgtccgg | tgccgcgggg | ctgcgtctgc | tgttgctgct | 240 |
| gctgctgccg | ctgctaggca | aagtggcatt | gggcctctac | ttctcgaggg | atgcttactg | 300 |
| ggagaagctg | tatgtggacc | aggcggccgg | cacgcccttg | ctgtacgtcc | atgccctgcg | 360 |
| ggacgcccct | gaggaggtgc | ccagcttccg | cctgggccag | catctctacg | gcacgtaccg | 420 |
| cacacggctg | catgagaaca | actggatctg | catccaggag | gacaccggcc | tcctctacct | 480 |
| taaccggagc | ctggaccata | gctcctggga | gaagctcagt | gtccgcaacc | gcggctttcc | 540 |
| cctgctcacc | gtctacctca | aggtcttcct | gtcacccaca | tcccttcgtg | agggcgagtg | 600 |
| ccagtggcca | ggctgtgccc | gcgtatactt | ctccttcttc | aacacctcct | ttccagcctg | 660 |
| cagctcccctc | aagccccggg | agctctgctt | cccagagaca | aggccctcct | tccgcattcg | 720 |
| ggagaaccga | cccccaggca | ccttccacca | gttccgcctg | ctgcctgtgc | agttcttgtg | 780 |
| ccccaacatc | agcgtggcct | acaggctcct | ggagggtgag | ggtctgcccct | tccgctgcgc | 840 |
| cccggacagc | tggaggtga | gcacgcgctg | ggccctggac | cgcgagcagc | gggagaagta | 900 |
| cgagctggtg | gccgtgtgca | ccgtgcacgc | cggcgcgcgc | gaggaggtgg | tgatggtgcc | 960 |
| cttcccggtg | accgtgtacg | acgaggacga | ctcggcgccc | accttccccg | cgggcgtcga | 1020 |
| caccgccagc | gccgtggtgg | agttcaagcg | gaaggaggac | accgtggtgg | ccacgctgcg | 1080 |
| tgtcttcgat | gcagacgtgg | tacctgcatc | agggagctg | gtgaggcggt | acacaagcac | 1140 |
| gctgctcccc | ggggacacct | gggcccagca | gaccttccgg | gtggaacact | ggcccaacga | 1200 |
| gacctcggtc | caggccaacg | gcagcttcgt | gcgggcgacc | gtacatgact | ataggctggt | 1260 |
| tctcaaccgg | aacctctcca | tctcggagaa | ccgcaccatg | cagctggcgg | tgctggtcaa | 1320 |
| tgactcagac | ttccagggcc | caggagcggg | cgtcctcttg | ctccacttca | acgtgtcggt | 1380 |
| gctgccggtc | agcctgcacc | tgcccagtac | ctactccctc | tccgtgagca | ggagggctcg | 1440 |
| ccgatttgcc | cagatcggga | aagtctgtgt | ggaaaactgc | caggcattca | gtggcatcaa | 1500 |
| cgtccagtac | aagctgcatt | cctctggtgc | caactgcagc | acgctagggg | tggtcacctc | 1560 |
| agccgaggac | acctcgggga | tcctgtttgt | gaatgacacc | aaggcccctgc | ggcggcccaa | 1620 |
| gtgtgccgaa | cttcactaca | tggtggtggc | caccgaccag | cagacctcta | ggcaggccca | 1680 |

```
ggcccagctg cttgtaacag tggaggggtc atatgtggcc gaggaggcgg gctgcccct    1740 gtcctgtgca gtcagcaaga gacggctgga gtgtgaggag tgtggcggcc tgggctcccc    1800
aacaggcagg tgtgagtgga ggcaaggaga tggcaaaggg atcaccagga acttctccac    1860
ctgctctccc agcaccaaga cctgccccga cggccactgc gatgttgtgg agacccaaga    1920
catcaacatt tgccctcagg actgcctccg gggcagcatt gttggggac acgagcctgg     1980 ggagccccgg gggattaaag ctggctatgg cacctgcaac tgcttccctg aggaggagaa    2040
gtgcttctgc gagcccgaag acatccagga tccactgtgc gacgagctgt gccgcacggt    2100
gatcgcagcc gctgtcctct tctccttcat cgtctcggtg ctgctgtctg ccttctgcat    2160
ccactgctac cacaagtttg cccacaagcc acccatctcc tcagctgaga tgaccttccg    2220
gaggcccgcc caggccttcc cggtcagcta ctcctcttcc ggtgcccgcc ggccctcgct    2280
ggactccatg gagaaccagg tctccgtgga tgccttcaag atcctggagg atccaaagtg    2340
ggaattccct cggaagaact tggttcttgg aaaaactcta ggagaaggcg aatttggaaa    2400
agtggtcaag gcaacggcct tccatctgaa aggcagagca gggtacacca cggtggccgt    2460
gaagatgctg aaagaaacg cctccccgag tgagcttcga gacctgctgt cagagttcaa     2520
cgtcctgaag caggtcaacc acccacatgt catcaaattg tatggggcct gcagccagga    2580
tggcccgctc ctcctcatcg tggagtacgc caaatacggc tccctgcggg gcttcctccg    2640
cgagagccgc aaagtggggc ctggctacct gggcagtgga ggcagccgca actccagctc    2700
cctggaccac ccggatgagc gggccctcac catgggcgac ctcatctcat ttgcctggca    2760
gatctcacag gggatgcagt atctggccga gatgaagctc gttcatcggg acttggcagc    2820
cagaaacatc ctggtagctg aggggcgaa gatgaagatt tcggatttcg gcttgtcccg    2880
agatgtttat gaagaggatt cctacgtgaa gaggagccag ggtcggattc cagttaaatg    2940
gatggcaatt gaatcccttt ttgatcatat ctacaccacg caaagtgatg tatggtcttt    3000
tggtgtcctg ctgtgggaga tcgtgaccct aggggaaac ccctatcctg ggattcctcc     3060
tgagcggctc ttcaaccttc tgaagaccgg ccaccggatg gagaggccag acaactgcag    3120
cgaggagatg taccgcctga tgctgcaatg ctggaagcag gagccggaca aaaggccggt    3180
gtttgcggac atcagcaaag acctggaaaa gatgatggtt aagaggagag actacttgga    3240
ccttgcggcg tccactccat ctgactccct gatttatgac gacggcctct cagaggagga    3300
gacaccgctg gtggactgta taatgcccc cctccctcga gccctccctt ccacatggat     3360
tgaaaacaaa ctctatggca tgtcagaccc gaactggcct ggagagagtc ctgtaccact    3420
cacgagagct gatggcacta acactgggtt tccaagatat ccaaatgata gtgtatatgc    3480
taactggatg ctttcacccct cagcggcaaa attaatggac acgtttgata gttaacattt    3540
ctttgtgaaa ggtaatggac tcacaagggg aagaaacatg ctgagaatgg aaagtctacc    3600 ggcccttct ttgtgaacgt cacattggcc gagccgtgtt cagttcccag gtggcagact    3660 cgttttggt agtttgtttt aacttccaag gtggtttac ttctgatagc cggtgatttt      3720
ccctcctagc agacatgcca caccgggtaa gagctctgag tcttagtggt taagcattcc    3780
tttctcttca gtgcccagca gcacccgtg ttggtctgtg tccatcagtg accaccaaca     3840
ttctgtgttc acatgtgtgg gtccaacact tactacctgg tgtatgaaat tggacctgaa    3900
ctgttggatt tttctagttg ccgccaaaca aggcaaaaaa atttaaacat gaagcacaca    3960
cacaaaaaag gcagtaggaa aaatgctggc cctgatgacc tgtccttatt cagaatgaga    4020
```

```
gactgcgggg ggggcctggg ggtagtgtca atgcccctcc agggctggag gggaagaggg      4080
gccccgagga tgggcctggg ctcagcattc gagatcttga aatgattttt tttttaatca      4140
tgcaaccttt ccttaggaag acatttggtt ttcatcatga ttaagatgat tcctagattt      4200
agcacaatgg agagattcca tgccatcttt actatgtgga tggtggtatc agggaagagg      4260
gctcacaaga cacatttgtc ccccgggccc accacatcat cctcacgtgt tcggtactga      4320
gcagccacta cccctgatga aacagtatg aagaaagggg gctgttggag tcccagaatt       4380
gctgacagca gaggctttgc tgctgtgaat cccacctgcc accagcctgc agcacacccc      4440
acagccaagt agaggcgaaa gcagtggctc atcctacctg ttaggagcag gtagggcttg      4500
tactcacttt aatttgaatc ttatcaactt actcataaag ggacaggcta gctagctgtg      4560
ttagaagtag caatgacaat gaccaaggac tgctacacct ctgattacaa ttctgatgtg      4620
aaaaagatgg tgtttggctc ttatagagcc tgtgtgaaag gcccatggat cagctcttcc      4680
tgtgtttgta atttaatgct gctacaagat gtttctgttt cttagattct gaccatgact      4740
cataagcttc ttgtcattct tcattgcttg tttgtggtca cagatgcaca acactcctcc      4800
agtcttgtgg gggcagcttt tgggaagtct cagcagctct tctggctgtg ttgtcagcac      4860
tgtaacttcg cagaaaagag tcggattacc aaaacactgc ctgctcttca gacttaaagc      4920
actgatagga cttaaaatag tctcattcaa atactgtatt ttatataggc atttcacaaa      4980
aacagcaaaa ttgtggcatt ttgtgaggcc aaggcttgga tgcgtgtgta atagagcctt      5040
gtggtgtgtg cgcacacacc cagagggaga gtttgaaaaa tgcttattgg acacgtaacc      5100
tggctctaat ttgggctgtt tttcagatac actgtgataa gttctttttac aaatatctat      5160 agacatggta aacttttggt tttcagatat gcttaatgat agtcttacta aatgcagaaa      5220
taagaataaa ctttctcaaa ttattaaaaa tgcctacaca gtaagtgtga attgctgcaa      5280
caggtttgtt ctcaggaggg taagaactcc aggtctaaac agctgaccca gtgatgggga      5340
atttatcctt gaccaattta tccttgacca ataacctaat tgtctattcc tgagttataa      5400
aagtccccat ccttattagc tctactggaa ttttcataca cgtaaatgca gaagttacta      5460
agtattaagt attactgagt attaagtagt aatctgtcag ttattaaaat ttgtaaaatc      5520
tatttatgaa aggtcattaa accagatcat gttcctttt ttgtaatcaa ggtgactaag       5580
aaaatcagtt gtgtaaataa aatcatgtat cataaaaaaa aaaaaaaaa                  5629
```

<210> SEQ ID NO 4
<211> LENGTH: 4174
<212> TYPE: DNA
<213> ORGANISM: Homo sapiens

<400> SEQUENCE: 4

```
agtcccgcga ccgaagcagg gcgcgcagca gcgctgagtg ccccggaacg tgcgtcgcgc        60
ccccagtgtc cgtcgcgtcc gccgcgcccc gggcggggat ggggcggcca gactgagcgc      120
cgcacccgcc atccagaccc gccggcccta gccgcagtcc ctccagccgt ggccccagcg      180
cgcacgggcg atggcgaagg cgacgtccgg tgccgcgggg ctgcgtctgc tgttgctgct      240
gctgctgccg ctgctaggca aagtggcatt gggcctctac ttctcgaggg atgcttactg      300
ggagaagctg tatgtggacc aggcggccgg cacgcccttg ctgtacgtcc atgccctgcg      360
ggacgcccct gaggaggtgc ccagcttccg cctgggccag catctctacg gcacgtaccg      420 cacacgggctg catgagaaca actggatctg catccaggag gacaccggcc tcctctacct      480
taaccggagc ctggaccata gctcctggga gaagctcagt gtccgcaacc gcggctttcc      540
```

```
cctgctcacc gtctacctca aggtcttcct gtcacccaca tcccttcgtg agggcgagtg      600
ccagtggcca ggctgtgccc gcgtatactt ctccttcttc aacacctcct ttccagcctg      660
cagctccctc aagccccggg agctctgctt cccagagaca aggccctcct tccgcattcg      720
ggagaaccga cccccaggca ccttccacca gttccgcctg ctgcctgtgc agttcttgtg      780
ccccaacatc agcgtggcct acaggctcct ggagggtgag ggtctgccct tccgctgcgc      840
cccggacagc ctggaggtga gcacgcgctg ggccctggac cgcgagcagc gggagaagta      900
cgagctggtg gccgtgtgca ccgtgcacgc cggcgcgcgc gaggaggtgg tgatggtgcc      960
cttcccggtg accgtgtacg acgaggacga ctcggcgccc accttccccg cgggcgtcga     1020
caccgccagc gccgtggtgg agttcaagcg gaaggaggac accgtggtgg ccacgctgcg     1080
tgtcttcgat gcagacgtgg tacctgcatc aggggagctg gtgaggcggt acacaagcac     1140
gctgctcccc ggggacacct gggcccagca gaccttccgg gtggaacact ggcccaacga     1200
gacctcggtc caggccaacg gcagcttcgt gcgggcgacc gtacatgact ataggctggt     1260
tctcaaccgg aacctctcca tctcggagaa ccgcaccatg cagctggcgg tgctggtcaa     1320
tgactcagac ttccagggcc caggagcggg cgtcctcttg ctccacttca cgtgtcggt      1380 gctgccggtc agcctgcacc tgcccagtac ctactccctc tccgtgagca ggagggctcg     1440
ccgatttgcc cagatcggga aagtctgtgt ggaaaactgc caggcattca gtggcatcaa     1500
cgtccagtac aagctgcatt cctctggtgc caactgcagc acgctagggg tggtcacctc     1560
agccgaggac acctcgggga tcctgttttgt gaatgacacc aaggccctgc ggcggcccaa     1620
gtgtgccgaa cttcactaca tggtggtggc caccgaccag cagacctcta ggcaggccca     1680
ggcccagctg cttgtaacag tggaggggtc atatgtggcc gaggaggcgg gctgcccct      1740 gtcctgtgca gtcagcaaga cggctggag gtgtgaggag tgtggcggcc tgggctcccc     1800
aacaggcagg tgtgagtgga ggcaaggaga tggcaaaggg atcaccagga acttctccac     1860
ctgctctccc agcaccaaga cctgccccga cggccactgc gatgttgtgg agacccaaga     1920
catcaacatt tgccctcagg actgcctccg gggcagcatt gttggggac acgagcctgg     1980 ggagccccgg gggattaaag ctggctatgg cacctgcaac tgcttccctg aggaggagaa     2040
gtgcttctgc gagcccgaag acatccagga tccactgtgc gacgagctgt gccgcacggt     2100
gatcgcagcc gctgtcctct tctccttcat cgtctcggtg ctgctgtctg ccttctgcat     2160
ccactgctac cacaagtttg cccacaagcc acccatctcc tcagctgaga tgaccttccg     2220
gagccccgcc caggccttcc cggtcagcta tcctcttcc ggtgcccgcc ggccctcgct     2280
ggactccatg gagaaccagg tctccgtgga tgccttcaag atcctggagg atccaaagtg     2340
ggaattccct cggaagaact tggttcttgg aaaaactcta ggagaaggcg aatttggaaa     2400
agtggtcaag gcaacggcct tccatctgaa aggcagagca gggtacacca cggtggccgt     2460
gaagatgctg aaagagaacg cctccccgag tgagcttcga gacctgctgt cagagttcaa     2520
cgtcctgaag caggtcaacc acccacatgt catcaaattg tatgggccgct gcagccagga     2580 tggcccgctc ctcctcatcg tggagtacgc caaatacggc tccctgcggg gcttcctccg     2640
cgagagccgc aaagtggggc ctggctacct gggcagtgga ggcagccgca actccagctc     2700
cctggaccac ccggatgagc gggccctcac catgggcgac ctcatctcat tgcctggca      2760 gatctcacag gggatgcagt atctggccga gatgaagctc gttcatcggg acttggcagc     2820
cagaaacatc ctggtagctg aggggcggaa gatgaagatt tcggatttcg gcttgtcccg     2880
```

```
agatgtttat gaagaggatt cctacgtgaa gaggagccag ggtcggattc cagttaaatg    2940
gatggcaatt gaatccctt ttgatcatat ctacaccacg caaagtgatg tatggtcttt    3000
tggtgtcctg ctgtgggaga tcgtgaccct aggggaaac ccctatcctg ggattcctcc    3060
tgagcggctc ttcaaccttc tgaagaccgg ccaccggatg gagaggccag acaactgcag    3120
cgaggagatg taccgcctga tgctgcaatg ctggaagcag gagccggaca aaaggccggt    3180
gtttgcggac atcagcaaag acctggagaa gatgatggtt aagaggagag actacttgga    3240
ccttgcggcg tccactccat ctgactccct gatttatgac gacggcctct cagaggagga    3300
gacaccgctg gtggactgta ataatgcccc cctccctcga gccctccctt ccacatggat    3360
tgaaaacaaa ctctatggta gaatttccca tgcatttact agattctagc accgctgtcc    3420
cctctgcact atccttcctc tctgtgatgc tttttaaaaa tgtttctggt ctgaacaaaa    3480
ccaaagtctg ctctgaacct ttttatttgt aaatgtctga ctttgcatcc agtttacatt    3540
taggcattat tgcaactatg tttttctaaa aggaagtgaa aataagtgta attaccacat    3600
tgcccagcaa cttaggatgg tagaggaaaa aacagatcag ggcggaactc tcagggagga    3660
ccaagaacag gttgaataag gcgcttctgg ggtgggaatc aagtcatagt acttctactt    3720
taactaagtg gataaatata caaatctggg gaggtattca gttgagaaag gagccaccag    3780
caccactcag cctgcactgg gagcacagcc aggttccccc agacccctcc tgggcaggca    3840
ggtgcctctc agaggccacc cggcactggc gagcagccac tggccaagcc tcagcccag    3900 tcccagccac atgtcctcca tcaggggtag cgaggttgca ggagctggct ggccctggga    3960
ggacgcaccc ccactgctgt tttcacatcc tttcccttac ccaccttcag gacggttgtc    4020
acttatgaag tcagtgctaa agctggagca gttgcttttt gaaagaacat ggtctgtggt    4080
gctgtggtct tacaatggac agtaaatatg gttcttgcca aaactccttc ttttgtcttt    4140
gattaaatac tagaaattta aaaaaaaaaa aaaa                                4174
```

<210> SEQ ID NO 5  
<211> LENGTH: 13  
<212> TYPE: PRT  
<213> ORGANISM: Artificial Sequence  
<220> FEATURE:  
<223> OTHER INFORMATION: Description of Artificial Sequence: Synthetic peptide  
<220> FEATURE:  
<221> NAME/KEY: MOD_RES  
<222> LOCATION: (1)..(1)  
<223> OTHER INFORMATION: 6-aminohexanoic acid

<400> SEQUENCE: 5

```
Xaa Lys Lys Lys Lys Asp Asp Ile Tyr Phe Phe Phe Gly
1               5                   10
```